US008097445B2

(12) United States Patent
Bower et al.

(10) Patent No.: US 8,097,445 B2
(45) Date of Patent: Jan. 17, 2012

(54) EXO-ENDO CELLULASE FUSION PROTEIN

(75) Inventors: Benjamin S. Bower, Palo Alto, CA (US); Edmund A. Larenas, Palo Alto, CA (US); Colin Mitchinson, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 11/088,306

(22) Filed: Mar. 23, 2005

(65) Prior Publication Data

US 2006/0057672 A1    Mar. 16, 2006

Related U.S. Application Data

(60) Provisional application No. 60/556,598, filed on Mar. 25, 2004.

(51) Int. Cl.
| | |
|---|---|
| *C12N 9/42* | (2006.01) |
| *C12N 1/00* | (2006.01) |
| *C12N 15/74* | (2006.01) |
| *C12P 21/06* | (2006.01) |
| *C12P 19/34* | (2006.01) |
| *C12P 7/08* | (2006.01) |
| *C07H 21/04* | (2006.01) |
| *C07K 1/00* | (2006.01) |

(52) U.S. Cl. ... 435/209; 435/69.1; 435/91.1; 435/254.1; 435/254.11; 435/254.6; 435/471; 435/484; 435/163; 536/23.2; 536/23.4; 536/23.1; 530/350

(58) Field of Classification Search .................. 435/183, 435/254.11, 320.1, 209, 69.1, 91.1, 254.1, 435/254.6, 471, 484, 163; 530/402, 350; 536/23.4, 23.2, 23.1
See application file for complete search history.

(56) References Cited

U.S. PATENT DOCUMENTS

| | | | |
|---|---|---|---|
| 4,435,307 A | 3/1984 | Barbesgaard et al. | |
| 5,110,735 A | 5/1992 | Tucker et al. | |
| 5,202,247 A * | 4/1993 | Kilburn et al. ................ | 435/195 |
| 5,246,853 A | 9/1993 | Clarkson et al. | |
| 5,275,944 A | 1/1994 | Himmel et al. | |
| 5,475,101 A | 12/1995 | Ward et al. | |
| 5,536,655 A * | 7/1996 | Thomas et al. ................ | 435/209 |
| 5,648,263 A | 7/1997 | Schulein et al. | |
| 5,691,178 A | 11/1997 | Schulein et al. | |
| 5,712,142 A | 1/1998 | Adney et al. | |
| 5,776,757 A | 7/1998 | Schulein et al. | |
| 5,861,271 A | 1/1999 | Fowler et al. | |
| 5,874,276 A | 2/1999 | Fowler et al. | |
| 5,989,899 A * | 11/1999 | Bower et al. ................ | 435/263 |
| 6,255,115 B1 | 7/2001 | Beijersbergen et al. | |
| 2003/0219854 A1* | 11/2003 | Guarna et al. ................ | 435/68.1 |

FOREIGN PATENT DOCUMENTS

| | | |
|---|---|---|
| GB | 2094826 | 3/1982 |
| GB | 2095275 | 3/1982 |
| WO | WO 9105039 | 4/1991 |
| WO | WO 92/01797 | 2/1992 |
| WO | WO 92/06209 | 4/1992 |
| WO | WO 9315186 | 8/1993 |
| WO | WO 94/28117 | 12/1994 |
| WO | WO 94/29460 | 12/1994 |
| WO | WO 96/02551 | 2/1996 |
| WO | WO 9602551 | 2/1996 |
| WO | WO 97/27306 | 7/1997 |
| WO | WO 98/31821 | 7/1998 |
| WO | WO 0070031 | 11/2000 |
| WO | WO 2005/093050 | 10/2005 |

OTHER PUBLICATIONS

Shoemaker et al., Molecular cloning of exo-cellobiohydrolase I derived from *Trichoderma reesei* strain L27. Bio/Technology 1983, vol. 1: 691-696.*
Warren et al., A bifunctional exoglucanase-endoglucanase fusion protein. Gene 1987, vol. 61 : 421-427.*
Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacement of the active-site cysteine with glutamate. Biochemistry, 1999, vol. 38: 11643-11650.*
Seffernick et al., Melamine deaminase and atrazine chlorohydrolase: 98 percent identical but functionally different. J. Bacteriol., 2001, vol. 183 (8): 2405-2410.*
Shoemaker et al., Molecular cloning of exo-cellobiohydrolase I derived from *Trichoderma reesei* strain L27. Bio/Technology, 1983, vol. 1: 691-696.*
Shoemaker et al., Molecular cloning of exo-cellobiohydrolase I derived from *Trichoderma reesei* strain L27. Bio/Technology 1983, vol. 1: 691-696 in IDS.*
PCT International Search Report for PCT/US2005/010158, Sep. 19, 2005.
Baker, et al., A new thermostable endoglucanase, Acidothermus cellulolyticus E1. Synergism with *Trichoderma reesei* CBH1 and comparison to Thermomonospora fusca $E_5$, *Applied Biochemistry and Biotechnology*, V. 45/46, 1994, pp. 245-256.
Berquist, et al., "Expression of xylanase enzymes from thermophilic microorganisms in fungal hosts," *Extremophiles*, V. 6, N. 3, Jun. 2002, pp. 177-184.
DeFaria, et al., "Expression and processing of a major xylanase (xyn2) from the thermophilic fungus Humicola grisea var. thermoidea in *Trichoderma reesei*," *Letters in Applied Microbiology*, V. 34, N. 2, 2002, pp. 119-123.
Keranen et al., "Production of recombinant proteins in the filamentous fungus *Trichoderma reesei*," *Current Opinion in Biotechnology*, V. 5, N. 5, 1995, pp. 534-537.
Sandgren, et al, "The X-ray Crystal Structure of the *Trichoderma reesei* Family 12 Endoglucanase 3," *JMB 308*, 295-310, 2001.
Nyysoenen, et al., "Protein producti9on by 1-18 the filamentous fungus *Trichoderma reesei*: secretion of active antibody molecules," *Canadian J. of Botany*, V. 70, N. suppl 1, Jan. 1995, pp. S885-S890.
Nyyssonen, et al., "Multiple roles of the cellulose CBHI in enhancing production of fusion antibodies by the filamentous fungus *Trichoderma reesei*," *Current Genetics*, New York, NY, US, pp. 71-79.

(Continued)

*Primary Examiner* — Ganapathirama Raghu

(57) ABSTRACT

The present invention relates to a heterologous exo-endo cellulase fusion construct, which encodes a fusion protein having cellulolytic activity comprising a catalytic domain derived from a fungal exo-cellobiohydrolase and a catalytic domain derived from an endoglucanase. The invention also relates to vectors and fungal host cells comprising the heterologous exo-endo cellulase fusion construct as well as methods for producing a cellulase fusion protein and enzymatic cellulase compositions.

7 Claims, 23 Drawing Sheets

OTHER PUBLICATIONS

Shoemaker, et al., "Molecular cloning of exo-cellobiohydrolase I derived from *Trichoderma reesei* strain L27," *BIO/Technology*, V. 1, N. 8, 1983-10, pp. 691-696.

Warren et al., "A bifunctional exoglucanase-endoglucanase fusion protein," *GENE*, 1987, V.61, N.3, pp. 421-427.

Altschul, S. F., et al., J. Mol. Biol. 215:403-410, 1990. *Basic Local Alignment Search Tool.*

Altschul, S. F., et al., Nucleic Acids Res. 25:3389-3402, 1997. *Gapped BLAST and PSI-BLAST: a New Generation of Protein Database Search Programs.*

Aro, N. J Biol Chem. Jun. 29, 2001; 276(26):24309-14. (Epub Apr. 13, 2001.) *ACEII, a Novel Transcriptional Activator Involved in Regulation of Cellulase and Xylanase. . . .*

Aubert J.P. Academic Press pp. 71-86(1988). *Scale Up of Cellulase Production and Utilization.*

Baker et al., Appl. Biochem. And Biotechnol. 45/46:245-256, 1994.

Baker et al., Appl. Biochem. Biotechnol. 70-72:395-403 (1998) . *Hydrolysis of Cellulase Using Ternary Mixture of Purified Cellulases.*

Becker et al., Biochem J. (2001) 356:19-30. *Engineering of a Glycosidase Family 7 Cellobiohydrolase to More Alkaline pH Optimum. . . .*

Bennett, J.W. and Lasure, L.L. (eds.) More Gene Manipulations in Fungi. Academic Press, pp. 396-428, 1991.

Bhikhabhai, R. et al., J. Appl. Biochem. 6:336, 1984. *Isolation of Cellulolytic Enzymes From Trichoderma Reesei QM 9414.*

Boel et al. EMBO J 3:1581-1585 1984. *Two different types of intervening sequences in the glucoamylase gene from Aspergillus niger.*

Brigidi, DeRossi, Bertarini, Riccardi and Matteuzzi, (1990), FEMS Microbiol. Lett. 55: 135-138. *Genetic Transformation of Intact Cells of Bacillus Subtilis by Electroporation.*

Brumbauer, A. et al., Bioseparation 7:287-295, 1999. *Fractionation of Cellulase and B-glucosidase In A Trichoderma Reesei Culture Liquid By Use Of Two-Phase Partitioning.*

Campbell, et al., (1989) Curr. Genet. 16:53-56, 1989, *Improved Transformation Efficiency of Aspergillus Niger Using The Homologous.*

Collmer A. and D. B. Wilson, Bio/Technol. 1: 594-601, 1983. *Cloning And Expression of A Thermomonospora YX Endocellulase Gene in E. Coli.*

Deutscher, Methods in Enzymology, vol. 182, No. 57, pp. 779-780, 1990. *Rethinking Your Purfication Procedure.*

Ellouz, S. et al., J. Chromatography 396:307, 1987. *Analytical Separation of Trichoderma Reesei Cellulases by Ion-Exchange Fast Protein Liquid Chromatography.*

Filho, et al. Can. J. Microbiol. 42:1-5, 1996. *Purification and Characterization of a B-glucosidase From Solid-State Cultures of Humicola Grisea var. Thermoidea.*

Fliess et al., Eur. J. Appl. Microbiol. Biotechnol. 17:314-318, 1983. *Characterization of Cellulase by HPLC Separation.*

Foreman, P. J. Biol. Chem 278:31988-31997. *Transcriptional Regulation of Biomass-Degrading Enzymes in the Filamentous Fungus Trichoderma Reesei.*

Fusarium include Bajar, Podila and Kolattukudy, (1991) *Proc. Natl. Acad. Sci.* USA 88: 8202-8212.

Goedegebuur et al, (2002) Curr. Genet 41: 89-98. *Cloning and Relational Analysis of 15 Novel Fingal Endoglucanases From Family 12 Glycosyl Hydrolase.*

Goldman, G. Curr. Genet. 17:169-174, (1990), *Transformation of Trichoderma harzianum by high-voltage electric pulse.*

Goyal et al., Bioresource Technol. 36:37-50, 1991. *Characteristics of Fungal Cellulases.*

Hazell, B. W. et al., Lett. Appl. Microbiol. 30:282-286, 2000. *Rapid Transformation of High Cellulase-Producing Mutant Strains of Trichoderma Reesei by Microprojectile Bombardment.*

Henikoff & Henikoff, Proc. Natl. Acad. Sci. USA 89:10915 (1992). *Amino Acid Substitution Matrices From Protein Blocks.*

Herr et al., Appl. Microbiol. Biotechnol. 5:29-36, 1978. *Purification and Properties of an Extracellular B-Glucosidase from Lenzites trabea.*

Hu et al., Mol Cell Biol. vol. 11, No. 11, pp. 5792-5799, 1991. *Antibodies Specific for the Human Retinoblastoma Protein Identify a Family Related Polypeptides.*

Ilmen, M. et al., Appl. Environ. Microbiol. 63:1298-1306 (1997). *Regulation of Cellulase Gene Expression in the Filamentous Fungus Trichoderma reesei.*

Jeenes et al., Biotechnol. Genet. Eng. Rev. 9:327 -369, 1991. *Heterologous Protein Production by Filamentous Fungi.*

Kawaguchi, T et al., Gene 173(2):287-8, 1996. *Cloning and Sequencing of the cDNA Encoding B-Glucosidase 1 From Aspergillus Aculeatus.*

Kelley et al. EMBO J. 4 :475-479, 1985. *Transformation of Aspergillus Niger by the amdS Gene of Aspergillus Nidulans.*

Knowles, J. et al., TIBTECH 5, 255-261, 1987. *Cellulase Families and Their Genes.*

Krishna, S. et al., Bioresource Tech. 77:193-196, 2001. *Simultaneous Saccharification and Fermentation of Lignocellulosic Wastes to Ethanol Using a Thermotolerant Yeast.*

Kuhls K. et al., Proc. Natl. Acad. Sci. USA 93(15): 7755-7760, 1996. *Molecular Evidence That the Asexual Industrial Fungus Trichoderma reesei Is a Clonal Derivative of the Ascomycete. . . .*

Kumar, A., et al., Textile Chemist and Colorist 29:37-42, 1997. *Optimizing the Use of Cellulase Enzymes in Finishing Cellulosic Fabrics.*

Lorito, Hayes, DiPietro and Harman (1993) Curr. Genet. 24: 349-356; *Biolistic transformation of Trichoderma harizanum and Gliocladium virens using plasmid and genomic DNA.*

Medve, J. et al., J. Chromatography A 808:153, 1998. *Ion-Exchange Chromatographic Purification and Quantitative Analysis of Trichoderma reesei Cellulase Cellibiohydrolase. . . .*

Mitsuishi et al., FEBS (1990) 275:135-138. *Site Directed Mutagenesis of the Putative Catalytic Residues of Trichoderma reesei Cellobiohydrolase. . . .*

Mohagheghi, A. et al., Int. J. Syst. Bacteriol. 36:435-443, 1986. *Isolation and Characterization of Acidothermus cellulyticus gen. nov., sp.nov. A New Genus of Thermophilic, Acidophilic Cellulolytic Bacteria.*

Needleman & Wunsch, J. Mol. Biol. 48:443 (1970). *A General Method Applicable to the Search for Similarities in the Amino Acid Sequence of Two Proteins.*

Nidetzky and Claeyssens Biotech. Bioeng. (1994) 44:961-966. *Specific Quantification of Trichoderma reesei Cellulases in Reconstituted Mixtures and its Application to Cellulase-Cellulose Binding Studies.*

Nieves et al., Appl. Biochem. and Biotechnol. 51/52 211-223, 1995. *Quantitation of Acidothermus cellulyticus E1 Endoglucanase and Thermomonspora fusca E3 Exoglucanase Using Enzyme-Linked Immunosorbent Assay (ELISA).*

Nunberg et al. Mol. Cell Biol. 4:2306-2315 1984. *Molecular Cloning and Characterization of the Glucoamylase Gene of Aspergillus awamori.*

Ohmiya et al., Biotechnol. Gen. Engineer. Rev. 14:365-414, 1997. *Structure of Cellulase and Their Applications.*

Okada, M. et al., Appl. Environ. Microbiol., 64:555-563, 1998. *Molecular Characterization and Heterologous Expression of Gene Encoding A Low-Molecular-Mass Endoglucanase From Trichoderma reesei QM914.*

Ooi et al., Nucleic Acids Res. 18:5884, 1990. *Complete nucleotide sequence of a gene coding for Aspergillus aculeatus cellulase (FI-CMCase).*

Pearson & Lipman, Proc. Nat'l Acad. Sci. USA 85:2444 (1988). *Improved Tools for Biological Sequence Comparison.*

Penttila et al., Gene 45:253-263, 1986. *Homology between cellulase genes of Trichoderma reesei : complete nucleotide sequence of the endoglucanase I gene.*

Penttila et al., Gene 61: 155-164, 1987. *A Versatile Transformation System for the Cellulolytic Filamentous Fungus Trichoderma reesei.*

Penttila et al., Gene 63: 103-112, 1988. *Efficient Secretion of Two Fungal Cellobiohydrolases by Sccharomyces cerevisiae.*

Pere, J., et al., in Proc. Tappi Pulping Conf., Nashville, TN, 27-31, pp. 693-696, 1996.

Pourquie, J. et al., Biochemistry and Genetics of Cellulose Degradation, eds., 1988.

Saarilahti et al., Gene 90:9-14, 1990. *CeIS: a novel endoglucanase identified from Erwina carotovora subsp. Carotovora.*

Sakamoto et al., Curr. Genet. 27:435-439, 1995. *Cloning and sequencing of cellulase cDNA from Aspergillus kawachii and its expression in Saccharomyces cerevisiae.*

Saloheimo M, et al., Gene 63:11-22, 1988. *EGIII, a new endoglucanase from Trichoderma reesei : the characterization of both gene and enzyme.*

Saloheimo, A. et al., Molecular Microbiology, 13:219-228, 1994. *A Novel, Small Endoglucanase Gene, egl5 From Trichoderma reesei Isolated by Expression in Yeast.*

Saloheimo, M. et al., Eur. J. Biochem., 249:584-591, 1997. *cDNA Cloning of a Trichoderma reesei Cellulase and Demonstration of Endoglucanase Activity by Expression in Yeast.*

Schell, D. at al. J.Appl Biochem. Biotechnol. 105-69-86 (2003).

Schulein, Methods Enzymol., 160, 25, pp. 234 et seq, 1988. *Cellulases of Trichoderma Reesei.*

Scopes, Methods Enzymol. 90: 479-91, 1982. *Purification of All Glycolytic Enzymes From One Muscle Extract.*

Sheir-Neiss, et al., Appl. Microbiol. Biotechnol. 20:46-53 (1984). *Characterization of the secreted cellulases of Trichoderma reesei wild type and mutants during controlled fermentations.*

Shoemaker et al., Biochem. Biophys. Acat. 523:133-146 1978. *Enzymic Activities of Endo-1,4-B-D-Glucanases Purified From Trichoderma viride.*

Shoemaker, S. et al., Bio/Technology, 1:691-696, 1983. *Molecular Cloning of Exo-Cellobiohydrolase 1 Derived From Trichoderma reesei Strain 1.27.*

Smith, T. et al. Adv Appl. Math 2:482 (1981) *Comparision of Biosequences.*

Smith P. K. et al., Biochem. 150:76-85, 1985. *Measurement of Protein Using Bicinchonic Acid.*

Srisodsuk et al., J. Biotech. (1997) 57:49-57.

Srisodsuk, M. et al. J. Biol. Chem. 268(28): 20756-20761, 1993. *Role of the Interdomain Linker Peptide of Trichoderma reesei Cellobiohydrolase I in Its Interaction With Crystalline Cellulose.*

Strathern et al., eds. (1981) The Molecular Biology of the Yeast Saccharomyces, Cold Spring Harbor Press, Plainview. N.Y.

Suurnakki, A. et al., Cellulose 7:189-209, 2000. *Trichoderma reesei Cellulases and their core domanis in the Hydrolysis and modification of chemical pulp.*

Teeri, T. et al., Gene, 51:43-52, 1987. *Homologous Domains in Trichoderma reesei Cellulolytic Enzymes: Gene Sequence and Expression of Cellobiohydrolase II.*

Tomaz and Queiroz, J. Chromatography A 865:123-128, 1999. *Studies on the Chromatographic Fractionation of Trichoderma reesei Cellulase by Hydrophobic Interaction.*

Tomme, P. et al., Eur. J. Biochem. 170:575-581, 1988. *Studies of the Cellulolytic System of Trichoderma Reesei QM 9414.*

Van Tilbeurgh et al., FEBS Lett. 169:215, 1984. *Separation of endo- and exo-type cellulose using a new affinity chromatography method.*

Van Tilbeurgh, H. et al., FEBS Lett. 204:223-227, 1986. *Limited proteolysis of the cellobiohydrolase I from Trichoderma reesei.*

Ward, M, et al., (1993), Appl. Microbiol. Biotechnol. 39:738-743. *Use of Aspergillus overproducing mutants, cured for integrated plasmid, to overproduce heterologous proteins.*

Wood et al., Methods in Enzymology, 160, 25, p. 87 et seq, 1988.

Wood, Biochem. Soc. Trans., 13, pp. 407-410, 1985.

Yelton, Hamer and Timberlake (1984) Proc. Natl. Acad. Sci. USA 81: 1470-1474; *Transformation of Aspergillus Nidulans by Using a trpC plasmid.*

Zhang, S. et al., Biochem. 34:3386-3395, 1995. *Characterization of a Thermomonospora fusca Exocellulase.*

\* cited by examiner

CBH1-E1 Fusion Construct

*T.reesei cbh1 core, linker (no CBD)*

+

*Acidothermus cellulolyticus endoglucanase 1 core (E1)*

Figure 2

DNA sequence of *T. reesei cbh1* signal sequence+catalytic domain+linker (1570 bases)

<u>ATGTATCGGAAGTTGGCCGTCATCTCGGCCTTCTTGGCCACAGCTCGTGCTCA</u>
GTCGGCCTGCACTCTCCAATCGGAGACTCACCCGCCTCTGACATGGCAG
AAATGCTCGTCTGGTGGCACTTGCACTCAACAGACAGGCTCCGTGGTCA
TCGACGCCAACTGGCGCTGGACTCACGCTACGAACAGCAGCACGAACTG
CTACGATGGCAACACTTGGAGCTCGACCCTATGTCCTGACAACGAGACC
TGCGCGAAGAACTGCTGTCTGGACGGTGCCGCCTACGCGTCCACGTACG
GAGTTACCACGAGCGGTAACAGCCTCTCCATTGGCTTTGTCACCCAGTC
TGCGCAGAAGAACGTTGGCGCTCGCCTTTACCTTATGGCGAGCGACACG
ACCTACCAGGAATTCACCCTGCTTGGCAACGAGTTCTCTTTCGATGTTGA
TGTTTCGCAGCTGCCGTAAGTGACTTACCATGAACCCCTGACGTATCTTC
TTGTGGGCTCCCAGCTGACTGGCCAATTTAAGGTGCGGCTTGAACGGAG
CTCTCTACTTCGTGTCCATGGACGCGGATGGTGGCGTGAGCAAGTATCC
CACCAACACCGCTGGCGCCAAGTACGGCACGGGGTACTGTGACAGCCAG
TGTCCCCGCGATCTGAAGTTCATCAATGGCCAGGCCAACGTTGAGGGCT
GGGAGCCGTCATCCAACAACGCAAACACGGGCATTGGAGGACACGGAA
GCTGCTGCTCTGAGATGGATATCTGGGAGGCCAACTCCATCTCCGAGGC
TCTTACCCCCCACCCTTGCACGACTGTCGGCCAGGAGATCTGCGAGGGT
GATGGGTGCGGCGGAACTTACTCCGATAACAGATATGGCGGCACTTGCG
ATCCCGATGGCTGCGACTGGAACCCATACCGCCTGGGCAACACCAGCTT
CTACGGCCCTGGCTCAAGCTTTACCCTCGATACCACCAAGAAATTGACC
GTTGTCACCCAGTTCGAGACGTCGGGTGCCATCAACCGATACTATGTCC
AGAATGGCGTCACTTTCCAGCAGCCCAACGCCGAGCTTGGTAGTTACTC
TGGCAACGAGCTCAACGATGATTACTGCACAGCTGAGGAGGCAGAATTC
GGCGGATCCTCTTTCTCAGACAAGGGCGGCCTGACTCAGTTCAAGAAGG
CTACCTCTGGCGGCATGGTTCTGGTCATGAGTCTGTGGGATGATGTGAG
TTTGATGGACAAACATGCGCGTTGACAAAGAGTCAAGCAGCTGACTGAG
ATGTTACAGTACTACGCCAACATGCTGTGGCTGGACTCCACCTACCCGA
CAAACGAGACCTCCTCCACACCCGGTGCCGTGCGCGGAAGCTGCTCCAC
CAGCTCCGGTGTCCCTGCTCAGGTCGAATCTCAGTCTCCAACGCCAAG
GTCACCTTCTCCAACATCAAGTTCGGACCCATTGGCAGCACCGGCAACC
*CTAGCGGCGGCAACCCTCCCGGCGGAAACCCGCCTGGCACCACCACCACCCGCC*
*GCCCAGCCACTACCACTGGAAGCTCTCCCGGACCTACTAGT*

Figure 3

Amino acid sequence of *T. reesei cbh1* signal sequence + catalytic domain + linker (480 amino acids)

<u>MYRKLAVISAFLATARA</u>QSACTLQSETHPPLTWQKCSSGGTCTQQTGSVVID
ANWRWTHATNSSTNCYDGNTWSSTLCPDNETCAKNCCLDGAAYASTYGVT
TSGNSLSIGFVTQSAQKNVGARLYLMASDTTYQEFTLLGNEFSFDVDVSQLP
CGLNGALYFVSMDADGGVSKYPTNTAGAKYGTGYCDSQCPRDLKFINGQA
NVEGWEPSSNNANTGIGGHGSCCSEMDIWEANSISEALTPHPCTTVGQEICE
GDGCGGTYSDNRYGGTCDPDGCDWNPYRLGNTSFYGPGSSFTLDTTKKLT
VVTQFETSGAINRYYVQNGVTFQQPNAELGSYSGNELNDDYCTAEEAEFGG
SSFSDKGGLTQFKKATSGGMVLVMSLWDDYYANMLWLDSTYPTNETSSTP
GAVRGSCSTSSGVPAQVESQSPNAKVTFSNIKFGPIGSTGN*PSGGNPPGGNPPG*
*TTTTRRPATTTGSSPGPTS*

Figure 4

DNA sequence of *Acidothermus cellulolyticus* GH5A endoglucanase *1* catalytic domain
(1077 bases)

GCGGGCGGCGGCTATTGGCACACGAGCGGCCGGGAGATCCTGGACGCGAAC
AACGTGCCGGTACGGATCGCCGGCATCAACTGGTTTGGGTTCGAAACCTGCA
ATTACGTCGTGCACGGTCTCTGGTCACGCGACTACCGCAGCATGCTCGACCA
GATAAAGTCGCTCGGCTACAACACAATCCGGCTGCCGTACTCTGACGACATT
CTCAAGCCGGGCACCATGCCGAACAGCATCAATTTTTACCAGATGAATCAGG
ACCTGCAGGGTCTGACGTCCTTGCAGGTCATGGACAAAATCGTCGCGTACGC
CGGTCAGATCGGCCTGCGCATCATTCTTGACCGCCACCGACCGGATTGCAGC
GGGCAGTCGGCGCTGTGGTACACGAGCAGCGTCTCGGAGGCTACGTGGATTT
CCGACCTGCAAGCGCTGGCGCAGCGCTACAAGGGAAACCCGACGGTCGTCG
GCTTTGACTTGCACAACGAGCCGCATGACCCGGCCTGCTGGGGCTGCGGCGA
TCCGAGCATCGACTGGCGATTGGCCGCCGAGCGGGCCGGAAACGCCGTGCTC
TCGGTGAATCCGAACCTGCTCATTTTCGTCGAAGGTGTGCAGAGCTACAACG
GAGACTCCTACTGGTGGGGCGGCAACCTGCAAGGAGCCGGCCAGTACCCGGT
CGTGCTGAACGTGCCGAACCGCCTGGTGTACTCGGCGCACGACTACGCGACG
AGCGTCTACCCGCAGACGTGGTTCAGCGATCCGACCTTCCCCAACAACATGC
CCGGCATCTGGAACAAGAACTGGGGATACCTCTTCAATCAGAACATTGCACC
GGTATGGCTGGGCGAATTCGGTACGACACTGCAATCCACGACCGACCAGACG
TGGCTGAAGACGCTCGTCCAGTACCTACGGCCGACCGCGCAATACGGTGCGG
ACAGCTTCCAGTGGACCTTCTGGTCCTGGAACCCCGATTCCGGCGACACAGG
AGGAATTCTCAAGGATGACTGGCAGACGGTCGACACAGTAAAAGACGGCTAT
CTCGCGCCGATCAAGTCGTCGATTTTCGATCCTGTCGGC

Figure 5

Amino acid sequence of *Acidothermus cellulolyticus* GH5A endoglucanase 1 catalytic domain (359 amino acids)

AGGGYWHTSGREILDANNVPVRIAGINWFGFETCNYVVHGLWSRDYRSMLDQI
KSLGYNTIRLPYSDDILKPGTMPNSINFYQMNQDLQGLTSLQVMDKIVAYAGQIG
LRIILDRHRPDCSGQSALWYTSSVSEATWISDLQALAQRYKGNPTVVGFDLHNEP
HDPACWGCGDPSIDWRLAAERAGNAVLSVNPNLLIFVEGVQSYNGDSYWWGG
NLQGAGQYPVVLNVPNRLVYSAHDYATSVYPQTWFSDPTFPNNMPGIWNKNW
GYLFNQNIAPVWLGEFGTTLQSTTDQTWLKTLVQYLRPTAQYGADSFQWTFWS
WNPDSGDTGGILKDDWQTVDTVKDGYLAPIKSSIFDPVG

FIGURE 6A

DNA sequence of *Acidothermus cellulolyticus GH74* catalytic domain

GCGACGACTCAGCCGTACACCTGGAGCAACGTGGCGATCGGGGGCGGCGGC
TTTGTCGACGGGATCGTCTTCAATGAAGGTGCACCGGGAATTCTGTACGTGCG
GACGGACATCGGGGGGATGTATCGATGGGATGCCGCCAACGGGCGGTGGAT
CCCTCTTCTGGATTGGGTGGGATGGAACAATTGGGGGTACAACGGCGTCGTC
AGCATTGCGGCAGACCCGATCAATACTAACAAGGTATGGGCCGCCGTCGGAA
TGTACACCAACAGCTGGGACCCAAACGACGGAGCGATTCTCCGCTCGTCTGA
TCAGGGCGCAACGTGGCAAATAACGCCCTGCCGTTCAAGCTTGGCGGCAAC
ATGCCCGGGCGTGGAATGGGCGAGCGGCTTGCGGTGGATCCAAACAATGACA
ACATTCTGTATTTCGGCGCCCCGAGCGGCAAAGGGCTCTGGAGAAGCACAGA
TTCCGGCGCGACCTGGTCCCAGATGACGAACTTTCCGGACGTAGGCACGTAC
ATTGCAAATCCCACTGACACGACCGGCTATCAGAGCGATATTCAAGGCGTCG
TCTGGGTCGCTTTCGACAAGTCTTCGTCATCGCTCGGGCAAGCGAGTAAGACC
ATTTTTGTGGGCGTGGCGGATCCCAATAATCCGGTCTTCTGGAGCAGAGACG
GCGGCGCGACGTGGCAGGCGGTGCCGGGTGCGCCGACCGGCTTCATCCCGCA
CAAGGGCGTCTTTGACCCGGTCAACCACGTGCTCTATATTGCCACCAGCAAT
ACGGGTGGTCCGTATGACGGGAGCTCCGGCGACGTCTGGAAATTCTCGGTGA
CCTCCGGGACATGGACGCGAATCAGCCCGGTACCTTCGACGGACACGGCCAA
CGACTACTTTGGTTACAGCGGCCTCACTATCGACCGCCAGCACCCGAACACG
ATAATGGTGGCAACCCAGATATCGTGGTGGCCGGACACCATAATCTTTCGGA
GCACCGACGGCGGTGCGACGTGGACGCGGATCTGGGATTGGACGAGTTATCC
CAATCGAAGCTTGCGATATGTGCTTGACATTTCGGCGGAGCCTTGGCTGACCT
TCGGCGTACAGCCGAATCCTCCCGTACCGAGTCCGAAGCTCGGCTGGATGGA
TGAAGCGATGGCAATCGATCCGTTCAACTCTGATCGGATGCTCTACGGAACA
GGCGCGACGTTGTACGCAACAAATGATCTCACGAAGTGGGACTCCGGCGGCC
AGATTCATATCGCGCCGATGGTCAAAGGATTGGAGGAGACGGCGGTAAACG
ATCTCATCAGCCCGCCGTCTGGCGCCCCGCTCATCAGCGCTCTCGGAGACCTC
GGCGGCTTCACCCACGCCGACGTTACTGCCGTGCCATCGACGATCTTCACGTC

FIGURE 6B

ACCGGTGTTCACGACCGGCACCAGCGTCGACTATGCGGAATTGAATCCGTCG
ATCATCGTTCGCGCTGGAAGTTTCGATCCATCGAGCCAACCGAACGACAGGC
ACGTCGCGTTCTCGACAGACGGCGGCAAGAACTGGTTCCAAGGCAGCGAACC
TGGCGGGGTGACGACGGGCGGCACCGTCGCCGCATCGGCCGACGGCTCTCGT
TTCGTCTGGGCTCCCGGCGATCCCGGTCAGCCTGTGGTGTACGCAGTCGGATT
TGGCAACTCCTGGGCTGCTTCGCAAGGTGTTCCCGCCAATGCCCAGATCCGCT
CAGACCGGGTGAATCCAAAGACTTTCTATGCCCTATCCAATGGAACCTTCTAT
CGAAGCACGGACGGCGGCGTGACATTCCAACCGGTCGCGGCCGGTCTTCCGA
GCAGCGGTGCCGTCGGTGTCATGTTCCACGCGGTGCCTGGAAAAGAAGGCGA
TCTGTGGCTCGCTGCATCGAGCGGGCTTTACCACTCAACCAATGGCGGCAGC
AGTTGGTCTGCAATCACCGGCGTATCCTCCGCGGTGAACGTGGGATTTGGTA
AGTCTGCGCCCGGGTCGTCATACCCAGCCGTCTTTGTCGTCGGCACGATCGGA
GGCGTTACGGGGGCGTACCGCTCCGACGACGGTGGGACGACCTGGGTACGG
ATCAATGATGACCAGCACCAATACGGAAATTGGGGACAAGCAATCACCGGTG
ACCCGCGAATTTACGGGCGGGTGTACATAGGCACGAACGGCCGTGGAATTGT
CTACGGGGACATTGGTGGTGCGCCGTCCGGATCG

FIGURE 7

Amino acid sequence of *Acidothermus cellulolyticus* 74 catalytic domain (741 amino acids)

ATTQPYTWSNVAIGGGGFVDGIVFNEGAPGILYVRTDIGGMYRWDAANGRWIPL
LDWVGWNNWGYNGVVSIAADPINTNKVWAAVGMYTNSWDPNDGAILRSSDQ
GATWQITPLPFKLGGNMPGRGMGERLAVDPNNDNILYFGAPSGKGLWRSTDSG
ATWSQMTNFPDVGTYIANPTDTTGYQSDIQGVVWVAFDKSSSSLGQASKTIFVG
VADPNNPVFWSRDGGATWQAVPGAPTGFIPHKGVFDPVNHVLYIATSNTGGPY
DGSSGDVWKFSVTSGTWTRISPVPSTDTANDYFGYSGLTIDRQHPNTIMVATQIS
WWPDTIIFRSTDGGATWTRIWDWTSYPNRSLRYVLDISAEPWLTFGVQPNPPVPS
PKLGWMDEAMAIDPFNSDRMLYGTGATLYATNDLTKWDSGGQIHIAPMVKGLE
ETAVNDLISPPSGAPLISALGDLGGFTHADVTAVPSTIFTSPVFTTGTSVDYAELNP
SIIVRAGSFDPSSQPNDRHVAFSTDGGKNWFQGSEPGGVTTGGTVAASADGSRFV
WAPGDPGQPVVYAVGFGNSWAASQGVPANAQIRSDRVNPKTFYALSNGTFYRS
TDGGVTFQPVAAGLPSSGAVGVMFHAVPGKEGDLWLAASSGLYHSTNGGSSWS
AITGVSSAVNVGFGKSAPGSSYPAVFVVGTIGGVTGAYRSDDGGTTWVRINDDQ
HQYGNWGQAITGDPRIYGRVYIGTNGRGIVYGDIGGAPSGS

Figure 8

DNA sequence of *Thermobifida fusca* E5 (TfE5) endoglucanase including the cellulose binding domain - linker and catalytic domain but lacking a TfE5 signal sequence. (1293 bases)

```
GCCGGTCTCACCGCCACAGTCACCAAAGAATCCTCGTGGGACAACGGCTACT
CCGCGTCCGTCACCGTCCGCAACGACACCTCGAGCACCGTCTCCCAGTGGGA
GGTCGTCCTCACCCTGCCCGGCGGCACTACAGTGGCCCAGGTGTGGAACGCC
CAGCACACCAGCAGCGGCAACTCCCACACCTTCACCGGGGTTTCCTGGAACA
GCACCATCCCGCCCGGAGGCACCGCCTCTTCCGGCTTCATCGCTTCCGGCAGC
GGCGAACCCACCCACTGCACCATCAACGGCGCCCCTGCGACGAAGGCTCCG
AGCCGGGCGGCCCCGGCGGTCCCGGAACCCCCTCCCCCGACCCCGGCACGCA
GCCCGGCACCGGCACCCCGGTCGAGCGGTACGGCAAAGTCCAGGTCTGCGGC
ACCCAGCTCTGCGACGAGCACGGCAACCCGGTCCAACTGCGCGGCATGAGCA
CCCACGGCATCCAGTGGTTCGACCACTGCCTGACCGACAGCTCGCTGGACGC
CCTGGCCTACGACTGGAAGGCCGACATCATCCGCCTGTCCATGTACATCCAG
GAAGACGGCTACGAGACCAACCCGCGCGGCTTCACCGACCGGATGCACCAG
CTCATCGACATGGCCACGGCGCGCGGCCTGTACGTGATCGTGGACTGGCACA
TCCTCACCCCGGGCGATCCCCACTACAACCTGGACCGGGCCAAGACCTTCTTC
GCGGAAATCGCCCAGCGCCACGCCAGCAAGACCAACGTGCTCTACGAGATCG
CCAACGAACCCAACGGAGTGAGCTGGGCCTCCATCAAGAGCTACGCCGAAG
AGGTCATCCCGGTGATCCGCCAGCGCGACCCCGACTCGGTGATCATCGTGGG
CACCCGCGGCTGGTCGTCGCTCGGCGTCTCCGAAGGCTCCGGCCCCGCCGAG
ATCGCGGCCAACCCGGTCAACGCCTCCAACATCATGTACGCCTTCCACTTCTA
CGCGGCCTCGCACCGCGACAACTACCTCAACGCGCTGCGTGAGGCCTCCGAG
CTGTTCCCGGTCTTCGTCACCGAGTTCGGCACCGAGACCTACACCGGTGACG
GCGCCAACGACTTCCAGATGGCCGACCGCTACATCGACCTGATGGCGGAACG
GAAGATCGGGTGGACCAAGTGGAACTACTCGGACGACTTCCGTTCCGGCGCG
GTCTTCCAGCCGGGCACCTGCGCGTCCGGCGGCCCGTGGAGCGGTTCGTCGC
TGAAGGCGTCCGGACAGTGGGTGCGGAGCAAGCTCCAGTCCTGA
```

Figure 9

Amino acid sequence of the *Thermobifida fusca* E5 –cellulase including the cellulose binding domain - linker - catalytic domain but lacking a TfE5 signal sequence. (430 amino acids)

AGLTATVTKESSWDNGYSASVTVRNDTSSTVSQWEVVLTLPGGTTVAQVWNAQ
HTSSGNSHTFTGVSWNSTIPPGGTASSGFIASGSGEPTHCTINGAPCDEGSEPGGP
GGPGTPSPDPGTQPGTGTPVERYGKVQVCGTQLCDEHGNPVQLRGMSTHGIQW
FDHCLTDSSLDALAYDWKADIIRLSMYIQEDGYETNPRGFTDRMHQLIDMATAR
GLYVIVDWHILTPGDPHYNLDRAKTFFAEIAQRHASKTNVLYEIANEPNGVSWA
SIKSYAEEVIPVIRQRDPDSVIIVGTRGWSSLGVSEGSGPAEIAANPVNASNIMYAF
HFYAASHRDNYLNALREASELFPVFVTEFGTETYTGDGANDFQMADRYIDLMA
ERKIGWTKWNYSDDFRSGAVFQPGTCASGGPWSGSSLKASGQWVRSKLQS

Figure 10

DNA sequence of CBH1-E1 fusion (2656 bases)
*T.reesei cbh1* signal sequence+catalytic domain+linker+added amino acids
SKR+*Acidothermus cellulolyticus* GH5A catalytic domain ATGTATCGGAAGTTGGCCGTCATCTCGGCCTTCTTGGCCACAGCTCGTGCTCA
GTCGGCCTGCACTCTCCAATCGGAGACTCACCCGCCTCTGACATGGCAGAAA
TGCTCGTCTGGTGGCACTTGCACTCAACAGACAGGCTCCGTGGTCATCGACG
CCAACTGGCGCTGGACTCACGCTACGAACAGCAGCACGAACTGCTACGATGG
CAACACTTGGAGCTCGACCCTATGTCCTGACAACGAGACCTGCGCGAAGAAC
TGCTGTCTGGACGGTGCCGCCTACGCGTCCACGTACGGAGTTACCACGAGCG
GTAACAGCCTCTCCATTGGCTTTGTCACCCAGTCTGCGCAGAAGAACGTTGGC
GCTCGCCTTTACCTTATGGCGAGCGACACGACCTACCAGGAATTCACCCTGCT
TGGCAACGAGTTCTCTTTCGATGTTGATGTTTCGCAGCTGCCGTAAGTGACTT
ACCATGAACCCCTGACGTATCTTCTTGTGGGCTCCCAGCTGACTGGCCAATTT
AAGGTGCGGCTTGAACGGAGCTCTCTACTTCGTGTCCATGGACGCGGATGGT
GGCGTGAGCAAGTATCCCACCAACACCGCTGGCGCCAAGTACGGCACGGGGT
ACTGTGACAGCCAGTGTCCCCGCGATCTGAAGTTCATCAATGGCCAGGCCAA
CGTTGAGGGCTGGGAGCCGTCATCCAACAACGCAAACACGGGCATTGGAGG
ACACGGAAGCTGCTGCTCTGAGATGGATATCTGGGAGGCCAACTCCATCTCC
GAGGCTCTTACCCCCCACCCTTGCACGACTGTCGGCCAGGAGATCTGCGAGG
GTGATGGGTGCGGCGGAACTTACTCCGATAACAGATATGGCGGCACTTGCGA
TCCCGATGGCTGCGACTGGAACCCATACCGCCTGGGCAACACCAGCTTCTAC
GGCCCTGGCTCAAGCTTTACCCTCGATACCACCAAGAAATTGACCGTTGTCAC
CCAGTTCGAGACGTCGGGTGCCATCAACCGATACTATGTCCAGAATGGCGTC
ACTTTCCAGCAGCCCAACGCCGAGCTTGGTAGTTACTCTGGCAACGAGCTCA
ACGATGATTACTGCACAGCTGAGGAGGCAGAATTCGGCGGATCCTCTTTCTC
AGACAAGGGCGGCCTGACTCAGTTCAAGAAGGCTACCTCTGGCGGCATGGTT
CTGGTCATGAGTCTGTGGGATGATGTGAGTTTGATGGACAAACATGCGCGTT
GACAAAGAGTCAAGCAGCTGACTGAGATGTTACAGTACTACGCCAACATGCT
GTGGCTGGACTCCACCTACCCGACAAACGAGACCTCCTCCACACCCGGTGCC
GTGCGCGGAAGCTGCTCCACCAGCTCCGGTGTCCCTGCTCAGGTCGAATCTC
AGTCTCCCAACGCCAAGGTCACCTTCTCCAACATCAAGTTCGGACCCATTGGC
AGCACCGGCAACCCTAGCGGCGGCAACCCTCCCGGCGGAAACCCGCCTGGCA
CCACCACCACCCGCCGCCCAGCCACTACCACTGGAAGCTCTCCCGGACCTAC
TAGTAAGCGGGCGGGCGGCGGCTATTGGCACACGAGCGGCCGGGAGATCCT
GGACGCGAACAACGTGCCGGTACGGATCGCCGGCATCAACTGGTTTGGGTTC
GAAACCTGCAATTACGTCGTGCACGGTCTCTGGTCACGCGACTACCGCAGCA
TGCTCGACCAGATAAAGTCGCTCGGCTACAACACAATCCGGCTGCCGTACTC
TGACGACATTCTCAAGCCGGGCACCATGCCGAACAGCATCAATTTTTACCAG
ATGAATCAGGACCTGCAGGGTCTGACGTCCTTGCAGGTCATGGACAAAATCG
TCGCGTACGCCGGTCAGATCGGCCTGCGCATCATTCTTGACCGCCACCGACC
GGATTGCAGCGGGCAGTCGGCGCTGTGGTACACGAGCAGCGTCTCGGAGGCT
ACGTGGATTTCCGACCTGCAAGCGCTGGCGCAGCGCTACAAGGGAAACCCGA
CGGTCGTCGGCTTTGACTTGCACAACGAGCCGCATGACCCGGCCTGCTGGGG Figure 10 (Continued)

CTGCGGCGATCCGAGCATCGACTGGCGATTGGCCGCCGAGCGGGCCGGAAAC
GCCGTGCTCTCGGTGAATCCGAACCTGCTCATTTTCGTCGAAGGTGTGCAGAG
CTACAACGGAGACTCCTACTGGTGGGGCGGCAACCTGCAAGGAGCCGGCCA
GTACCCGGTCGTGCTGAACGTGCCGAACCGCCTGGTGTACTCGGCGCACGAC
TACGCGACGAGCGTCTACCCGCAGACGTGGTTCAGCGATCCGACCTTCCCCA
ACAACATGCCCGGCATCTGGAACAAGAACTGGGGATACCTCTTCAATCAGAA
CATTGCACCGGTATGGCTGGGCGAATTCGGTACGACACTGCAATCCACGACC
GACCAGACGTGGCTGAAGACGCTCGTCCAGTACCTACGGCCGACCGCGCAAT
ACGGTGCGGACAGCTTCCAGTGGACCTTCTGGTCCTGGAACCCCGATTCCGG
CGACACAGGAGGAATTCTCAAGGATGACTGGCAGACGGTCGACACAGTAAA
AGACGGCTATCTCGCGCCGATCAAGTCGTCGATTTTCGATCCTGTCGGCTAA

Figure 11

Amino acid sequence of CBH1-E1 fusion (841 amino acids)
*T.reesei cbh1* signal sequence+catalytic domain+linker+added amino acids
SKR+*Acidothermus cellulolyticus* GH5A catalytic domain MYRKLAVISAFLATARAQSACTLQSETHPPLTWQKCSSGGTCTQQTGSVVIDAN
WRWTHATNSSTNCYDGNTWSSTLCPDNETCAKNCCLDGAAYASTYGVTTSGNS
LSIGFVTQSAQKNVGARLYLMASDTTYQEFTLLGNEFSFDVDVSQLPCGLNGAL
YFVSMDADGGVSKYPTNTAGAKYGTGYCDSQCPRDLKFINGQANVEGWEPSSN
NANTGIGGHGSCCSEMDIWEANSISEALTPHPCTTVGQEICEGDGCGGTYSDNRY
GGTCDPDGCDWNPYRLGNTSFYGPGSSFTLDTTKKLTVVTQFETSGAINRYYVQ
NGVTFQQPNAELGSYSGNELNDDYCTAEEAEFGGSSFSDKGGLTQFKKATSGGM
VLVMSLWDDYYANMLWLDSTYPTNETSSTPGAVRGSCSTSSGVPAQVESQSPN
AKVTFSNIKFGPIGSTGNPSGGNPPGGNPPGTTTTRRPATTTGSSPGPTSKRAGGG
YWHTSGREILDANNVPVRIAGINWFGFETCNYVVHGLWSRDYRSMLDQIKSLGY
NTIRLPYSDDILKPGTMPNSINFYQMNQDLQGLTSLQVMDKIVAYAGQIGLRIILD
RHRPDCSGQSALWYTSSVSEATWISDLQALAQRYKGNPTVVGFDLHNEPHDPAC
WGCGDPSIDWRLAAERAGNAVLSVNPNLLIFVEGVQSYNGDSYWWGGNLQGA
GQYPVVLNVPNRLVYSAHDYATSVYPQTWFSDPTFPNNMPGIWNKNWGYLFN
QNIAPVWLGEFGTTLQSTTDQTWLKTLVQYLRPTAQYGADSFQWTFWSWNPDS
GDTGGILKDDWQTVDTVKDGYLAPIKSSIFDPVG

FIGURE 13A

DNA sequence of pTrex4 (10239 bases)

```
AAGCTTAACTAGTACTTCTCGAGCTCTGTACATGTCCGGTCGCGACGTACGCG
TATCGATGGCGCCAGCTGCAGGCGGCCGCCTGCAGCCACTTGCAGTCCCGTG
GAATTCTCACGGTGAATGTAGGCCTTTTGTAGGGTAGGAATTGTCACTCAAGC
ACCCCCAACCTCCATTACGCCTCCCCCATAGAGTTCCCAATCAGTGAGTCATG
GCACTGTTCTCAAATAGATTGGGGAGAAGTTGACTTCCGCCCAGAGCTGAAG
GTCGCACAACCGCATGATATAGGGTCGGCAACGGCAAAAAGCACGTGGCT
CACCGAAAAGCAAGATGTTTGCGATCTAACATCCAGGAACCTGGATACATCC
ATCATCACGCACGACCACTTTGATCTGCTGGTAAACTCGTATTCGCCCTAAAC
CGAAGTGACGTGGTAAATCTACACGTGGGCCCCTTTCGGTATACTGCGTGTGT
CTTCTCTAGGTGCCATTCTTTTCCCTTCCTCTAGTGTTGAATTGTTTGTGTTGG
AGTCCGAGCTGTAACTACCTCTGAATCTCTGGAGAATGGTGGACTAACGACT
ACCGTGCACCTGCATCATGTATATAATAGTGATCCTGAGAAGGGGGGTTTGG
AGCAATGTGGGACTTTGATGGTCATCAAACAAAGAACGAAGACGCCTCTTTT
GCAAAGTTTTGTTTCGGCTACGGTGAAGAACTGGATACTTGTTGTGTCTTCTG
TGTATTTTTGTGGCAACAAGAGGCCAGAGACAATCTATTCAAACACCAAGCT
TGCTCTTTTGAGCTACAAGAACCTGTGGGGTATATATCTAGAGTTGTGAAGTC
GGTAATCCCGCTGTATAGTAATACGAGTCGCATCTAAATACTCCGAAGCTGCT
GCGAACCCGGAGAATCGAGATGTGCTGGAAAGCTTCTAGCGAGCGGCTAAAT
TAGCATGAAAGGCTATGAGAAATTCTGGAGACGGCTTGTTGAATCATGGCGT
TCCATTCTTCGACAAGCAAAGCGTTCCGTCGCAGTAGCAGGCACTCATTCCCG
AAAAAACTCGGAGATTCCTAAGTAGCGATGGAACCGGAATAATATAATAGGC
AATACATTGAGTTGCCTCGACGGTTGCAATGCAGGGGTACTGAGCTTGGACA
TAACTGTTCCGTACCCCACCTCTTCTCAACCTTTGGCGTTTCCCTGATTCAGCG
TACCCGTACAAGTCGTAATCACTATTAACCCAGACTGACCGGACGTGTTTTGC
CCTTCATTTGGAGAAATAATGTCATTGCGATGTGTAATTTGCCTGCTTGACCG
ACTGGGGCTGTTCGAAGCCCGAATGTAGGATTGTTATCCGAACTCTGCTCGTA
GAGGCATGTTGTGAATCTGTGTCGGGCAGGACACGCCTCGAAGGTTCACGGC
AAGGGAAACCACCGATAGCAGTGTCTAGTAGCAACCTGTAAAGCCGCAATGC
AGCATCACTGGAAAATACAAACCAATGGCTAAAAGTACATAAGTTAATGCCT
AAAGAAGTCATATACCAGCGGCTAATAATTGTACAATCAAGTGGCTAAACGT
ACCGTAATTTGCCAACGGCTTGTGGGGTTGCAGAAGCAACGGCAAAGCCCCA
CTTCCCCACGTTTGTTTCTTCACTCAGTCCAATCTCAGCTGGTGATCCCCAAT
TGGGTCGCTTGTTTGTTCCGGTGAAGTGAAAGAAGACAGAGGTAAGAATGTC
TGACTCGGAGCGTTTTGCATACAACCAAGGGCAGTGATGGAAGACAGTGAAA
TGTTGACATTCAAGGAGTATTTAGCCAGGGATGCTTGAGTGTATCGTGTAAG
GAGGTTTGTCTGCCGATACGACGAATACTGTATAGTCACTTCTGATGAAGTGG
TCCATATTGAAATGTAAGTCGGCACTGAACAGGCAAAAGATTGAGTTGAAAC
TGCCTAAGATCTCGGGCCCTCGGGCCTTCGGCCTTTGGGTGTACATGTTTGTG
```

FIGURE 13B

CTCCGGGCAAATGCAAAGTGTGGTAGGATCGAACACACTGCTGCCTTTACCA
AGCAGCTGAGGGTATGTGATAGGCAAATGTTCAGGGGCCACTGCATGGTTTC
GAATAGAAAGAGAAGCTTAGCCAAGAACAATAGCCGATAAAGATAGCCTCA
TTAAACGGAATGAGCTAGTAGGCAAAGTCAGCGAATGTGTATATATAAAGGT
TCGAGGTCCGTGCCTCCCTCATGCTCTCCCATCTACTCATCAACTCAGATCC
TCCAGGAGACTTGTACACCATCTTTTGAGGCACAGAAACCCAATAGTCAACC
GCGGACTGCGCATCATGTATCGGAAGTTGGCCGTCATCTCGGCCTTCTTGGCC
ACAGCTCGTGCTCAGTCGGCCTGCACTCCAATCGGAGACTCACCCGCCTCT
GACATGGCAGAAATGCTCGTCTGGTGGCACTTGCACTCAACAGACAGGCTCC
GTGGTCATCGACGCCAACTGGCGCTGGACTCACGCTACGAACAGCAGCACGA
ACTGCTACGATGGCAACACTTGGAGCTCGACCCTATGTCCTGACAACGAGAC
CTGCGCGAAGAACTGCTGTCTGGACGGTGCCGCCTACGCGTCCACGTACGGA
GTTACCACGAGCGGTAACAGCCTCTCCATTGGCTTTGTCACCCAGTCTGCGCA
GAAGAACGTTGGCGCTCGCCTTTACCTTATGGCGAGCGACACGACCTACCAG
GAATTCACCCTGCTTGGCAACGAGTTCTCTTTCGATGTTGATGTTTCGCAGCT
GCCGTAAGTGACTTACCATGAACCCCTGACGTATCTTCTTGTGGGCTCCCAGC
TGACTGGCCAATTTAAGGTGCGGCTTGAACGGAGCTCTCTACTTCGTGTCCAT
GGACGCGGATGGTGGCGTGAGCAAGTATCCCACCAACACCGCTGGCGCCAA
GTACGGCACGGGGTACTGTGACAGCCAGTGTCCCCGCGATCTGAAGTTCATC
AATGGCCAGGCCAACGTTGAGGGCTGGGAGCCGTCATCCAACAACGCAAAC
ACGGGCATTGGAGGACACGGAAGCTGCTGCTCTGAGATGGATATCTGGGAGG
CCAACTCCATCTCCGAGGCTCTTACCCCCCACCCTTGCACGACTGTCGGCCAG
GAGATCTGCGAGGGTGATGGGTGCGGCGGAACTTACTCCGATAACAGATATG
GCGGCACTTGCGATCCCGATGGCTGCGACTGGAACCCATACCGCCTGGGCAA
CACCAGCTTCTACGGCCCTGGCTCAAGCTTTACCCTCGATACCACCAAGAAAT
TGACCGTTGTCACCCAGTTCGAGACGTCGGGTGCCATCAACCGATACTATGTC
CAGAATGGCGTCACTTTCCAGCAGCCCAACGCCGAGCTTGGTAGTTACTCTG
GCAACGAGCTCAACGATGATTACTGCACAGCTGAGGAGGCAGAATTCGGCGG
ATCCTCTTTCTCAGACAAGGGCGGCCTGACTCAGTTCAAGAAGGCTACCTCTG
GCGGCATGGTTCTGGTCATGAGTCTGTGGGATGATGTGAGTTTGATGGACAA
ACATGCGCGTTGACAAAGAGTCAAGCAGCTGACTGAGATGTTACAGTACTAC
GCCAACATGCTGTGGCTGGACTCCACCTACCCGACAAACGAGACCTCCTCCA
CACCCGGTGCCGTGCGCGGAAGCTGCTCCACCAGCTCCGGTGTCCCTGCTCA
GGTCGAATCTCAGTCTCCCAACGCCAAGGTCACCTTCTCCAACATCAAGTTCG
GACCCATTGGCAGCACCGGCAACCCTAGCGGCGGCAACCCTCCCGGCGGAAA
CCCGCCTGGCACCACCACCACCCGCCGCCCAGCCACTACCACTGGAAGCTCT
CCCGGACCTACTAGTAAGCGGATAAGGCGCGCCGCGCCAGCTCCGTGCGA
AAGCCTGACGCACCGGTAGATTCTTGGTGAGCCCGTATCATGACGGCGGCGG
GAGCTACATGGCCCCGGGTGATTTATTTTTTTGTATCTACTTCTGACCCTTTT
CAAATATACGGTCAACTCATCTTTCACTGGAGATGCGGCCTGCTTGGTATTGC
GATGTTGTCAGCTTGGCAAATTGTGGCTTTCGAAAACACAAAACGATTCCTTA

FIGURE 13C

```
GTAGCCATGCATTTTAAGATAACGGAATAGAAGAAAGAGGAAATTAAAAAA
AAAAAAAAAACAAACATCCCGTTCATAACCCGTAGAATCGCCGCTCTTCGTG
TATCCCAGTACCAGTTTATTTTGAATAGCTCGCCCGCTGGAGAGCATCCTGAA
TGCAAGTAACAACCGTAGAGGCTGACACGGCAGGTGTTGCTAGGGAGCGTCG
TGTTCTACAAGGCCAGACGTCTTCGCGGTTGATATATATGTATGTTTGACTGC
AGGCTGCTCAGCGACGACAGTCAAGTTCGCCCTCGCTGCTTGTGCAATAATC
GCAGTGGGGAAGCCACACCGTGACTCCCATCTTTCAGTAAAGCTCTGTTGGT
GTTTATCAGCAATACACGTAATTTAAACTCGTTAGCATGGGGCTGATAGCTTA
ATTACCGTTTACCAGTGCCGCGGTTCTGCAGCTTTCCTTGGCCCGTAAAATTC
GGCGAAGCCAGCCAATCACCAGCTAGGCACCAGCTAAACCCTATAATTAGTC
TCTTATCAACACCATCCGCTCCCCGGGATCAATGAGGAGAATGAGGGGGAT
GCGGGGCTAAAGAAGCCTACATAACCCTCATGCCAACTCCCAGTTTACACTC
GTCGAGCCAACATCCTGACTATAAGCTAACACAGAATGCCTCAATCCTGGGA
AGAACTGGCCGCTGATAAGCGCGCCCGCCTCGCAAAAACCATCCCTGATGAA
TGGAAAGTCCAGACGCTGCCTGCGGAAGACAGCGTTATTGATTTCCCAAAGA
AATCGGGGATCCTTTCAGAGGCCGAACTGAAGATCACAGAGGCCTCCGCTGC
AGATCTTGTGTCCAAGCTGGCGGCCGGAGAGTTGACCTCGGTGGAAGTTACG
CTAGCATTCTGTAAACGGGCAGCAATCGCCCAGCAGTTAGTAGGGTCCCCTC
TACCTCTCAGGGAGATGTAACAACGCCACCTTATGGGACTATCAAGCTGACG
CTGGCTTCTGTGCAGACAAACTGCGCCCACGAGTTCTTCCCTGACGCCGCTCT
CGCGCAGGCAAGGGAACTCGATGAATACTACGCAAAGCACAAGAGACCCGT
TGGTCCACTCCATGGCCTCCCCATCTCTCAAAGACCAGCTTCGAGTCAAGG
TACACCGTTGCCCCTAAGTCGTTAGATGTCCCTTTTGTCAGCTAACATATGC
CACCAGGGCTACGAAACATCAATGGGCTACATCTCATGGCTAAACAAGTACG
ACGAAGGGGACTCGGTTCTGACAACCATGCTCCGCAAAGCCGGTGCCGTCTT
CTACGTCAAGACCTCTGTCCCGCAGACCCTGATGGTCTGCGAGACAGTCAAC
AACATCATCGGGCGCACCGTCAACCCACGCAACAAGAACTGGTCGTGCGGCG
GCAGTTCTGGTGGTGAGGGTGCGATCGTTGGGATTCGTGGTGGCGTCATCGG
TGTAGGAACGGATATCGGTGGCTCGATTCGAGTGCCGGCCGCGTTCAACTTC
CTGTACGGTCTAAGGCCGAGTCATGGGCGGCTGCCGTATGCAAAGATGGCGA
ACAGCATGGAGGGTCAGGAGACGGTGCACAGCGTTGTCGGGCCGATTACGCA
CTCTGTTGAGGGTGAGTCCTTCGCCTCTTCCTTCTTTTCCTGCTCTATACCAGG
CCTCCACTGTCCTCCTTTCTTGCTTTTTATACTATATACGAGACCGGCAGTCAC
TGATGAAGTATGTTAGACCTCCGCCTCTTCACCAAATCCGTCCTCGGTCAGGA
GCCATGGAAATACGACTCCAAGGTCATCCCCATGCCCTGGCGCCAGTCCGAG
TCGGACATTATTGCCTCCAAGATCAAGAACGGCGGGCTCAATATCGGCTACT
ACAACTTCGACGGCAATGTCCTTCCACACCCTCCTATCCTGCGCGGCGTGGAA
ACCACCGTCGCCGCACTCGCCAAAGCCGGTCACACCGTGACCCCGTGGACGC
CATACAAGCACGATTTCGGCCACGATCTCATCTCCCATATCTACGCGGCTGAC
GGCAGCGCCGACGTAATGCGCGATATCAGTGCATCCGGCGAGCCGGCGATTC
CAAATATCAAAGACCTACTGAACCCGAACATCAAAGCTGTTAACATGAACGA
GCTCTGGGACACGCATCTCCAGAAGTGGAATTACCAGATGGAGTACCTTGAG
```

FIGURE 13D

AAATGGCGGGAGGCTGAAGAAAAGGCCGGGAAGGAACTGGACGCCATCATC
GCGCCGATTACGCCTACCGCTGCGGTACGGCATGACCAGTTCCGGTACTATG
GGTATGCCTCTGTGATCAACCTGCTGGATTTCACGAGCGTGGTTGTTCCGGTT
ACCTTTGCGGATAAGAACATCGATAAGAAGAATGAGAGTTTCAAGGCGGTTA
GTGAGCTTGATGCCCTCGTGCAGGAAGAGTATGATCCGGAGGCGTACCATGG
GGCACCGGTTGCAGTGCAGGTTATCGGACGGAGACTCAGTGAAGAGAGGAC
GTTGGCGATTGCAGAGGAAGTGGGGAAGTTGCTGGGAAATGTGGTGACTCCA
TAGCTAATAAGTGTCAGATAGCAATTTGCACAAGAAATCAATACCAGCAACT
GTAAATAAGCGCTGAAGTGACCATGCCATGCTACGAAAGAGCAGAAAAAAA
CCTGCCGTAGAACCGAAGAGATATGACACGCTTCCATCTCTCAAAGGAAGAA
TCCCTTCAGGGTTGCGTTTCCAGTCTAGACACGTATAACGGCACAAGTGTCTC
TCACCAAATGGGTTATATCTCAAATGTGATCTAAGGATGGAAAGCCCAGAAT
CTAGGCCTATTAATATTCCGGAGTATACGTAGCCGGCTAACGTTAACAACCG
GTACCTCTAGAACTATAGCTAGCATGCGCAAATTTAAAGCGCTGATATCGAT
CGCGCGCAGATCCATATATAGGGCCCGGGTTATAATTACCTCAGGTCGACGT
CCCATGGCCATTCGAATTCGTAATCATGGTCATAGCTGTTTCCTGTGTGAAAT
TGTTATCCGCTCACAATTCCACACAACATACGAGCCGGAAGCATAAAGTGTA
AAGCCTGGGGTGCCTAATGAGTGAGCTAACTCACATTAATTGCGTTGCGCTC
ACTGCCCGCTTTCCAGTCGGGAAACCTGTCGTGCCAGCTGCATTAATGAATCG
GCCAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATA
GCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCT
TGAAGTGGTGGCCTAACTACGGCTACACTAGAAGAACAGTATTTGGTATCTG
CGCTCTGCTGAAGCCAGTTACCTTCGGAAAAAGAGTTGGTAGCTCTTGATCCG
GCAAACAAACCACCGCTGGTAGCGGTGGTTTTTTGTTTGCAAGCAGCAGATT
ACGCGCAGAAAAAAGGATCTCAAGAAGATCCTTTGATCTTTTCTACGGGGT
CTGACGCTCAGTGGAACGAAAACTCACGTTAAGGGATTTTGGTCATGAGATT
ATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCC
AGTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTTT

FIGURE 13E

ATCCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAG
GCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCG
AGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACT
GATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATA
CTCATACTCTTCCTTTTTCAATATTATTGAAGCATTTATCAGGGTTATTGTCTC
ATGAGCGGATACATATTTGAATGTATTTAGAAAAATAAACAAATAGGGGTTC
CGCGCACATTTCCCCGAAAAGTGCCACCTGACGTCTAAGAAACCATTATTAT
CATGACATTAACCTATAAAAATAGGCGTATCACGAGGCCCTTTCGTCTCGCGC
GTTTCGGTGATGACGGTGAAAACCTCTGACACATGCAGCTCCCGGAGACGGT
CACAGCTTGTCTGTAAGCGGATGCCGGGAGCAGACAAGCCCGTCAGGGCGCG
TCAGCGGGTGTTGGCGGGTGTCGGGGCTGGCTTAACTATGCGGCATCAGAGC
AGATTGTACTGAGAGTGCACCATAAAATTGTAAACGTTAATATTTTGTTAAAA
TTCGCGTTAAATTTTGTTAAATCAGCTCATTTTTTAACCAATAGGCCGAAAT
CGGCAAAATCCCTTATAAATCAAAAGAATAGCCCGAGATAGGGTTGAGTGTT
GTTCCAGTTTGGAACAAGAGTCCACTATTAAAGAACGTGGACTCCAACGTCA
AAGGGCGAAAAACCGTCTATCAGGGCGATGGCCCACTACGTGAACCATCACC
CAAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCG
AGAAAGGAAGGGAAGAAAGCGAAAGGAGCGGGCGCTAGGGCGCTGGCAAG
TGTAGCGGTCACGCTGCGCGTAACCACCACACCCGCCGCGCTTAATGCGCCG
CTACAGGGCGCGTACTATGGTTGCTTTGACGTATGCGGTGTGAAATACCGCA
CAGATGCGTAAGGAGAAAATACCGCATCAGGCGCCATTCGCCATTCAGGCTG
CGCAACTGTTGGGAAGGGCGATCGGTGCGGGCCTCTTCGCTATTACGCCAGC
TGGCGAAAGGGGGATGTGCTGCAAGGCGATTAAGTTGGGTAACGCCAGGGTT
TTCCCAGTCACGACGTTGTAAAACGACGGCCAGTGCC

SDS-PAGE gel of supernate samples of shake flask grown *T.reesei* delete strain transformed with the fusion expression construct *cbh1-E1*

The fusion protein is indicated by the upper arrow, the cleaved E1 catalytic domain is indicated by the lower arrow SDS-PAGE gel of supernate samples of shake flask grown *T.reesei* delete strain transformed with the fusion expression construct *cbh1-GH74*

The fusion protein is indicated by the upper arrow, the cleaved GH74 catalytic domain is indicated by the lower arrow SDS-PAGE gel of supernate samples of shake flask grown *T. reesei* delete strain transformed with the fusion expression construct cbh1-E5

E5 is indicated by the lower arrows

SEQUENCE LISTING

```
<160> NUMBER OF SEQ ID NOS: 22

<210> SEQ ID NO 1
<211> LENGTH: 1570
<212> TYPE: DNA
<213> ORGANISM: Trichoderma reesei

<400> SEQUENCE: 1
atgtatcgga agttggccgt catctcggcc ttcttggcca cagctcgtgc tcagtcggcc      60
tgcactctcc aatcggagac tcacccgcct ctgacatggc agaaatgctc gtctggtggc     120
acttgcactc aacagacagg ctccgtggtc atcgacgcca actggcgctg gactcacgct     180
acgaacagca gcacgaactg ctacgatggc aacacttgga gctcgaccct atgtcctgac     240
aacgagacct gcgcgaagaa ctgctgtctg gacggtgccg cctacgcgtc cacgtacgga     300
gttaccacga gcggtaacag cctctccatt ggctttgtca cccagtctgc gcagaagaac     360
gttggcgctc gcctttacct tatggcgagc gacacgacct accaggaatt caccctgctt     420
ggcaacgagt tctctttcga tgttgatgtt tcgcagctgc cgtaagtgac ttaccatgaa     480
cccctgacgt atcttcttgt gggctcccag ctgactggcc aatttaaggt gcggcttgaa     540
cggagctctc tacttcgtgt ccatggacgc ggatggtggc gtgagcaagt atcccaccaa     600
caccgctggc gccaagtacg gcacggggta ctgtgacagc cagtgtcccc gcgatctgaa     660
gttcatcaat ggccaggcca acgttgaggg ctgggagccg tcatccaaca acgcaaacac     720
gggcattgga ggacacggaa gctgctgctc tgagatggat atctgggagg ccaactccat     780
ctccgaggct cttaccccccc acccttgcac gactgtcggc caggagatct gcgagggtga     840
tgggtgcggc ggaacttact ccgataacag atatggcggc acttgcgatc ccgatggctg     900
cgactggaac ccataccgcc tggcaacac cagcttctac ggccctggct caagctttac     960
cctcgatacc accaagaaat tgaccgttgt cacccagttc gagacgtcgg gtgccatcaa    1020
ccgatactat gtccagaatg gcgtcacttt ccagcagccc aacgccgagc ttggtagtta    1080
ctctggcaac gagctcaacg atgattactg cacagctgag gaggcagaat cggcggatc     1140 ctctttctca gacaagggcg gcctgactca gttcaagaag ctacctctg gcggcatggt     1200 tctggtcatg agtctgtggg atgatgtgag tttgatggac aaacatgcgc gttgacaaag    1260
agtcaagcag ctgactgaga tgttacagta ctacgccaac atgctgtggc tggactccac    1320
ctacccgaca aacgagacct cctccacacc cggtgccgtg cgcggaagct gctccaccag    1380
ctccggtgtc cctgctcagg tcgaatctca gtctcccaac gccaaggtca ccttctccaa    1440
catcaagttc ggacccattg gcagcaccgg caacccctagc ggcggcaacc ctcccggcgg    1500
aaacccgcct ggcaccacca ccaccgccg cccagccact accactggaa gctctcccgg    1560
acctactagt                                                            1570
```

<210> SEQ ID NO 2
<211> LENGTH: 51
<212> TYPE: DNA
<213> ORGANISM: Trichoderma reesei

<400> SEQUENCE: 2

```
atgtatcgga agttggccgt catctcggcc ttcttggcca cagctcgtgc t        51
```

<210> SEQ ID NO 3
<211> LENGTH: 1423
<212> TYPE: DNA
<213> ORGANISM: Trichoderma reesei

<400> SEQUENCE: 3

```
cagtcggcct gcactctcca atcggagact cacccgcctc tgacatggca gaaatgctcg    60
tctggtggca cttgcactca acagacaggc tccgtggtca tcgacgccaa ctggcgctgg   120
actcacgcta cgaacagcag cacgaactgc tacgatggca acacttggag ctcgacccta   180
tgtcctgaca acgagacctg cgcgaagaac tgctgtctgg acggtgccgc ctacgcgtcc   240
acgtacggag ttaccacgag cggtaacagc ctctccattg gctttgtcac ccagtctgcg   300
cagaagaacg ttggcgctcg cctttacctt atggcgagcg acacgaccta ccaggaattc   360
accctgcttg gcaacgagtt ctctttcgat gttgatgttt cgcagctgcc gtaagtgact   420
taccatgaac ccctgacgta tcttcttgtg ggctcccagc tgactggcca atttaaggtg   480
cggcttgaac ggagctctct acttcgtgtc catggacgcg gatggtggcg tgagcaagta   540
tcccaccaac accgctggcg ccaagtacgg cacgggtac tgtgacagcc agtgtccccg    600
cgatctgaag ttcatcaatg ccaggccaa cgttgagggc tgggagccgt catccaacaa   660
cgcaaacacg gcattggag acacggaag ctgctgctct gagatggata tctgggaggc    720
caactccatc tccgaggctc ttaccccca cccttgcacg actgtcggcc aggagatctg   780
cgagggtgat gggtgcggcg gaacttactc cgataacaga tatggcggca cttgcgatcc   840
cgatggctgc gactggaacc cataccgcct gggcaacacc agcttctacg ccctggctc   900
aagctttacc ctcgatacca ccaagaaatt gaccgttgtc acccagttcg agacgtcggg   960
tgccatcaac cgatactatg tccagaatgg cgtcactttc cagcagccca acgccgagct  1020
tggtagttac tctggcaacg agctcaacga tgattactgc acagctgagg aggcagaatt  1080
cggcggatcc tctttctcag acaagggcgg cctgactcag ttcaagaagg ctacctctgg  1140
cggcatggtt ctggtcatga gtctgtggga tgatgtgagt ttgatggaca acatgcgcg   1200
ttgacaaaga gtcaagcagc tgactgagat gttacagtac tacgccaaca tgctgtggct  1260
ggactccacc tacccgacaa acgagacctc ctccacaccc ggtgccgtgc gcggaagctg  1320
ctccaccagc tccggtgtcc ctgctcaggt cgaatctcag tctcccaacg ccaaggtcac  1380
cttctccaac atcaagttcg gacccattgg cagcaccggc aac                   1423
```

<210> SEQ ID NO 4
<211> LENGTH: 96
<212> TYPE: DNA
<213> ORGANISM: Trichoderma reesei

<400> SEQUENCE: 4

```
cctagcggcg gcaaccctcc cggcggaaac ccgcctggca ccaccaccac ccgccgccca    60
gccactacca ctggaagctc tcccggacct actagt                              96
```

<210> SEQ ID NO 5
<211> LENGTH: 480

```
<212> TYPE: PRT
<213> ORGANISM: Trichoderma reesei

<400> SEQUENCE: 5

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
            35                  40                  45

Val Val Ile Asp Ala Asn Trp Arg Trp Thr His Ala Thr Asn Ser Ser
        50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400
```

-continued

```
Asn Glu Thr Ser Ser Thr Pro Gly Ala Val Arg Gly Ser Cys Ser Thr
                405                 410                 415
Ser Ser Gly Val Pro Ala Gln Val Glu Ser Gln Ser Pro Asn Ala Lys
            420                 425                 430
Val Thr Phe Ser Asn Ile Lys Phe Gly Pro Ile Gly Ser Thr Gly Asn
        435                 440                 445
Pro Ser Gly Gly Asn Pro Pro Gly Gly Asn Pro Pro Gly Thr Thr Thr
    450                 455                 460
Thr Arg Arg Pro Ala Thr Thr Thr Gly Ser Ser Pro Gly Pro Thr Ser
465                 470                 475                 480

<210> SEQ ID NO 6
<211> LENGTH: 431
<212> TYPE: PRT
<213> ORGANISM: Trichoderma reesei

<400> SEQUENCE: 6

Gln Ser Ala Cys Thr Leu Gln Ser Glu Thr His Pro Pro Leu Thr Trp
1               5                   10                  15
Gln Lys Cys Ser Ser Gly Gly Thr Cys Thr Gln Gln Thr Gly Ser Val
            20                  25                  30
Val Ile Asp Ala Asn Trp Arg Trp Thr His Ala Thr Asn Ser Ser Thr
        35                  40                  45
Asn Cys Tyr Asp Gly Asn Thr Trp Ser Ser Thr Leu Cys Pro Asp Asn
    50                  55                  60
Glu Thr Cys Ala Lys Asn Cys Cys Leu Asp Gly Ala Ala Tyr Ala Ser
65                  70                  75                  80
Thr Tyr Gly Val Thr Thr Ser Gly Asn Ser Leu Ser Ile Gly Phe Val
                85                  90                  95
Thr Gln Ser Ala Gln Lys Asn Val Gly Ala Arg Leu Tyr Leu Met Ala
            100                 105                 110
Ser Asp Thr Thr Tyr Gln Glu Phe Thr Leu Leu Gly Asn Glu Phe Ser
        115                 120                 125
Phe Asp Val Asp Val Ser Gln Leu Pro Cys Gly Leu Asn Gly Ala Leu
    130                 135                 140
Tyr Phe Val Ser Met Asp Ala Asp Gly Gly Val Ser Lys Tyr Pro Thr
145                 150                 155                 160
Asn Thr Ala Gly Ala Lys Tyr Gly Thr Gly Tyr Cys Asp Ser Gln Cys
                165                 170                 175
Pro Arg Asp Leu Lys Phe Ile Asn Gly Gln Ala Asn Val Glu Gly Trp
            180                 185                 190
Glu Pro Ser Ser Asn Asn Ala Asn Thr Gly Ile Gly Gly His Gly Ser
        195                 200                 205
Cys Cys Ser Glu Met Asp Ile Trp Glu Ala Asn Ser Ile Ser Glu Ala
    210                 215                 220
Leu Thr Pro His Pro Cys Thr Thr Val Gly Gln Glu Ile Cys Glu Gly
225                 230                 235                 240
Asp Gly Cys Gly Gly Thr Tyr Ser Asp Asn Arg Tyr Gly Gly Thr Cys
                245                 250                 255
Asp Pro Asp Gly Cys Asp Trp Asn Pro Tyr Arg Leu Gly Asn Thr Ser
            260                 265                 270
Phe Tyr Gly Pro Gly Ser Ser Phe Thr Leu Asp Thr Thr Lys Lys Leu
        275                 280                 285
Thr Val Val Thr Gln Phe Glu Thr Ser Gly Ala Ile Asn Arg Tyr Tyr
    290                 295                 300
```

-continued

| | | | | | | | | | | | | | | |
|---|---|---|---|---|---|---|---|---|---|---|---|---|---|---|
|Val|Gln|Asn|Gly|Val|Thr|Phe|Gln|Pro|Asn|Ala|Glu|Leu|Gly|Ser|
|305| | | |310| | | |315| | | |320| | |

Tyr Ser Gly Asn Glu Leu Asn Asp Asp Tyr Cys Thr Ala Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn
        420                 425                 430

<210> SEQ ID NO 7
<211> LENGTH: 1077
<212> TYPE: DNA
<213> ORGANISM: Acidothermus cellulolyticus

<400> SEQUENCE: 7

```
gcgggcggcg gctattggca cacgagcggc cgggagatcc tggacgcgaa caacgtgccg      60
gtacggatcg ccggcatcaa ctggtttggg ttcgaaacct gcaattacgt cgtgcacggt     120
ctctggtcac gcgactaccg cagcatgctc gaccagataa agtcgctcgg ctacaacaca     180
atccggctgc cgtactctga cgacattctc aagcccggca ccatgccgaa cagcatcaat     240
ttttaccaga tgaatcagga cctgcagggt ctgacgtcct gcaggtcat ggacaaaatc      300
gtcgcgtacg ccggtcagat cggcctgcgc atcattcttg accgccaccg accggattgc     360
agcgggcagt cggcgctgtg gtacacgagc agcgtctcgg aggctacgtg gatttccgac     420
ctgcaagcgc tggcgcagcg ctacaaggga accccgacgg tcgtcggctt tgacttgcac     480
aacgagccgc atgacccggc ctgctggggc tgcggcgatc cgagcatcga ctggcgattg     540
gccgccgagc gggccggaaa cgccgtgctc tcggtgaatc cgaacctgct cattttcgtc     600
gaaggtgtgc agagctacaa cggagactcc tactggtggg gcggcaacct gcaaggagcc     660
ggccagtacc cggtcgtgct gaacgtgccg aaccgcctgg tgtactcggc gcacgactac     720
gcgacgagcg tctacccgca gacgtggttc agcgatccga ccttcccaa caacatgccc     780
ggcatctgga caagaactg gggataccct ttcaatcaga acattgcacc ggtatggctg     840
ggcgaattcg gtacgacact gcaatccacg accgaccaga cgtggctgaa gacgctcgtc     900
cagtacctac ggccgaccgc gcaatacggt gcggacagct ccagtggac cttctggtcc     960
tggaaccccg attccggcga cacaggagga attctcaagg atgactggca gacggtcgac    1020
acagtaaaag acggctatct cgcgccgatc aagtcgtcga ttttcgatcc tgtcggc      1077
```

<210> SEQ ID NO 8
<211> LENGTH: 359
<212> TYPE: PRT
<213> ORGANISM: Acidothermus cellulolyticus

<400> SEQUENCE: 8

Ala Gly Gly Gly Tyr Trp His Thr Ser Gly Arg Glu Ile Leu Asp Ala
1               5                   10                  15

Asn Asn Val Pro Val Arg Ile Ala Gly Ile Asn Trp Phe Gly Phe Glu

```
                    20                  25                  30
Thr Cys Asn Tyr Val Val His Gly Leu Trp Ser Arg Asp Tyr Arg Ser
            35                  40                  45

Met Leu Asp Gln Ile Lys Ser Leu Gly Tyr Asn Thr Ile Arg Leu Pro
 50                  55                  60

Tyr Ser Asp Asp Ile Leu Lys Pro Gly Thr Met Pro Asn Ser Ile Asn
 65                  70                  75                  80

Phe Tyr Gln Met Asn Gln Asp Leu Gln Gly Leu Thr Ser Leu Gln Val
                85                  90                  95

Met Asp Lys Ile Val Ala Tyr Ala Gly Gln Ile Gly Leu Arg Ile Ile
            100                 105                 110

Leu Asp Arg His Arg Pro Asp Cys Ser Gly Gln Ser Ala Leu Trp Tyr
        115                 120                 125

Thr Ser Ser Val Ser Glu Ala Thr Trp Ile Ser Asp Leu Gln Ala Leu
    130                 135                 140

Ala Gln Arg Tyr Lys Gly Asn Pro Thr Val Val Gly Phe Asp Leu His
145                 150                 155                 160

Asn Glu Pro His Asp Pro Ala Cys Trp Gly Cys Gly Asp Pro Ser Ile
                165                 170                 175

Asp Trp Arg Leu Ala Ala Glu Arg Ala Gly Asn Ala Val Leu Ser Val
            180                 185                 190

Asn Pro Asn Leu Leu Ile Phe Val Glu Gly Val Gln Ser Tyr Asn Gly
        195                 200                 205

Asp Ser Tyr Trp Trp Gly Gly Asn Leu Gln Gly Ala Gly Gln Tyr Pro
    210                 215                 220

Val Val Leu Asn Val Pro Asn Arg Leu Val Tyr Ser Ala His Asp Tyr
225                 230                 235                 240

Ala Thr Ser Val Tyr Pro Gln Thr Trp Phe Ser Asp Pro Thr Phe Pro
                245                 250                 255

Asn Asn Met Pro Gly Ile Trp Asn Lys Asn Trp Gly Tyr Leu Phe Asn
            260                 265                 270

Gln Asn Ile Ala Pro Val Trp Leu Gly Glu Phe Gly Thr Thr Leu Gln
        275                 280                 285

Ser Thr Thr Asp Gln Thr Trp Leu Lys Thr Leu Val Gln Tyr Leu Arg
    290                 295                 300

Pro Thr Ala Gln Tyr Gly Ala Asp Ser Phe Gln Trp Thr Phe Trp Ser
305                 310                 315                 320

Trp Asn Pro Asp Ser Gly Asp Thr Gly Gly Ile Leu Lys Asp Asp Trp
                325                 330                 335

Gln Thr Val Asp Thr Val Lys Asp Gly Tyr Leu Ala Pro Ile Lys Ser
            340                 345                 350

Ser Ile Phe Asp Pro Val Gly
        355

<210> SEQ ID NO 9
<211> LENGTH: 2223
<212> TYPE: DNA
<213> ORGANISM: Acidothermus cellulolyticus

<400> SEQUENCE: 9
gcgacgactc agccgtacac ctggagcaac gtggcgatcg ggggcggcgg ctttgtcgac      60
gggatcgtct tcaatgaagg tgcaccggga attctgtacg tgcggacgga catcgggggg     120
atgtatcgat gggatgccgc caacgggcgg tggatccctc ttctggattg ggtgggatgg     180
aacaattggg ggtacaacgg cgtcgtcagc attgcggcag acccgatcaa tactaacaag     240
```

```
gtatgggccg ccgtcggaat gtacaccaac agctgggacc caaacgacgg agcgattctc    300
cgctcgtctg atcagggcgc aacgtggcaa ataacgcccc tgccgttcaa gcttggcggc    360
aacatgcccg ggcgtggaat gggcgagcgg cttgcggtgg atccaaacaa tgacaacatt    420
ctgtatttcg gcgccccgag cggcaaaggg ctctggagaa gcacagattc cggcgcgacc    480
tggtcccaga tgacgaactt tccggacgta ggcacgtaca ttgcaaatcc cactgacacg    540
accggctatc agagcgatat tcaaggcgtc gtctgggtcg ctttcgacaa gtcttcgtca    600
tcgctcgggc aagcgagtaa gaccattttt gtgggcgtgg cggatcccaa taatccggtc    660
ttctggagca gagacggcgg cgcgacgtgg caggcggtgc cgggtgcgcc gaccggcttc    720
atcccgcaca agggcgtctt tgacccggtc aaccacgtgc tctatattgc caccagcaat    780
acgggtggtc cgtatgacgg gagctccggc gacgtctgga aattctcggt gacctccggg    840
acatggacgc gaatcagccc ggtaccttcg acggacacgg ccaacgacta ctttggttac    900
agcggcctca ctatcgaccg ccagcacccg aacacgataa tggtggcaac ccagatatcg    960
tggtggccgg acaccataat ctttcggagc accgacggcg gtgcgacgtg gacgcggatc   1020
tgggattgga cgagttatcc caatcgaagc ttgcgatatg tgcttgacat ttcggcggag   1080
ccttggctga ccttcggcgt acagccgaat cctcccgtac cgagtccgaa gctcggctgg   1140
atggatgaag cgatggcaat cgatccgttc aactctgatc ggatgctcta cggaacaggc   1200
gcgacgttgt acgcaacaaa tgatctcacg aagtgggact ccggcggcca gattcatatc   1260
gcgccgatgg tcaaaggatt ggaggagacg gcggtaaacg atctcatcag cccgccgtct   1320
ggcgccccgc tcatcagcgc tctcggagac ctcggcggct tcacccacgc cgacgttact   1380
gccgtgccat cgacgatctt cacgtcaccg gtgttcacga ccggcaccag cgtcgactat   1440
gcggaattga atccgtcgat catcgttcgc gctggaagtt tcgatccatc gagccaaccg   1500
aacgacaggc acgtcgcgtt ctcgacagac ggcggcaaga actggttcca aggcagcgaa   1560
cctggcgggg tgacgacggg cggcaccgtc gccgcatcgg ccgacggctc tcgtttcgtc   1620
tgggctcccg gcgatcccgg tcagcctgtg gtgtacgcag tcggatttgg caactcctgg   1680
gctgcttcgc aaggtgttcc cgccaatgcc cagatccgct cagaccgggt gaatccaaag   1740
actttctatg ccctatccaa tggaaccttc tatcgaagca cggacggcgg cgtgacattc   1800
caaccggtcg cggccggtct tccgagcagc ggtgccgtcg gtgtcatgtt ccacgcggtg   1860
cctggaaaag aaggcgatct gtggctcgct gcatcgagcg gctttaccac tcaaccaat   1920 ggcggcagca gttggtctgc aatcaccggc gtatcctccg cggtgaacgt gggatttggt   1980
aagtctgcgc ccgggtcgtc atacccagcc gtctttgtcg tcggcacgat cggaggcgtt   2040 acggggggcgt accgctccga cgacggtggg acgacctggg tacggatcaa tgatgaccag   2100
caccaatacg gaaattgggg acaagcaatc accggtgacc cgcgaattta cgggcgggtg   2160
tacataggca cgaacggccg tggaattgtc tacggggaca ttggtggtgc gccgtccgga   2220
tcg                                                                 2223
```

<210> SEQ ID NO 10
<211> LENGTH: 741
<212> TYPE: PRT
<213> ORGANISM: Acidothermus cellulolyticus

<400> SEQUENCE: 10

```
Ala Thr Thr Gln Pro Tyr Thr Trp Ser Asn Val Ala Ile Gly Gly Gly
1               5                   10                  15
```

```
Gly Phe Val Asp Gly Ile Val Phe Asn Glu Gly Ala Pro Gly Ile Leu
            20                  25                  30

Tyr Val Arg Thr Asp Ile Gly Gly Met Tyr Arg Trp Asp Ala Ala Asn
        35                  40                  45

Gly Arg Trp Ile Pro Leu Leu Asp Trp Val Gly Trp Asn Asn Trp Gly
50                  55                  60

Tyr Asn Gly Val Val Ser Ile Ala Ala Asp Pro Ile Asn Thr Asn Lys
65                  70                  75                  80

Val Trp Ala Ala Val Gly Met Tyr Thr Asn Ser Trp Asp Pro Asn Asp
                85                  90                  95

Gly Ala Ile Leu Arg Ser Ser Asp Gln Gly Ala Thr Trp Gln Ile Thr
            100                 105                 110

Pro Leu Pro Phe Lys Leu Gly Gly Asn Met Pro Gly Arg Gly Met Gly
        115                 120                 125

Glu Arg Leu Ala Val Asp Pro Asn Asn Asp Asn Ile Leu Tyr Phe Gly
130                 135                 140

Ala Pro Ser Gly Lys Gly Leu Trp Arg Ser Thr Asp Ser Gly Ala Thr
145                 150                 155                 160

Trp Ser Gln Met Thr Asn Phe Pro Asp Val Gly Thr Tyr Ile Ala Asn
                165                 170                 175

Pro Thr Asp Thr Thr Gly Tyr Gln Ser Asp Ile Gln Gly Val Val Trp
            180                 185                 190

Val Ala Phe Asp Lys Ser Ser Ser Leu Gly Gln Ala Ser Lys Thr
        195                 200                 205

Ile Phe Val Gly Val Ala Asp Pro Asn Asn Pro Val Phe Trp Ser Arg
210                 215                 220

Asp Gly Gly Ala Thr Trp Gln Ala Val Pro Gly Ala Pro Thr Gly Phe
225                 230                 235                 240

Ile Pro His Lys Gly Val Phe Asp Pro Val Asn His Val Leu Tyr Ile
                245                 250                 255

Ala Thr Ser Asn Thr Gly Gly Pro Tyr Asp Gly Ser Ser Gly Asp Val
            260                 265                 270

Trp Lys Phe Ser Val Thr Ser Gly Thr Trp Thr Arg Ile Ser Pro Val
        275                 280                 285

Pro Ser Thr Asp Thr Ala Asn Asp Tyr Phe Gly Tyr Ser Gly Leu Thr
290                 295                 300

Ile Asp Arg Gln His Pro Asn Thr Ile Met Val Ala Thr Gln Ile Ser
305                 310                 315                 320

Trp Trp Pro Asp Thr Ile Ile Phe Arg Ser Thr Asp Gly Gly Ala Thr
                325                 330                 335

Trp Thr Arg Ile Trp Asp Trp Ser Tyr Pro Asn Arg Ser Leu Arg
            340                 345                 350

Tyr Val Leu Asp Ile Ser Ala Glu Pro Trp Leu Thr Phe Gly Val Gln
        355                 360                 365

Pro Asn Pro Pro Val Pro Ser Pro Lys Leu Gly Trp Met Asp Glu Ala
370                 375                 380

Met Ala Ile Asp Pro Phe Asn Ser Asp Arg Met Leu Tyr Gly Thr Gly
385                 390                 395                 400

Ala Thr Leu Tyr Ala Thr Asn Asp Leu Thr Lys Trp Asp Ser Gly Gly
                405                 410                 415

Gln Ile His Ile Ala Pro Met Val Lys Gly Leu Glu Glu Thr Ala Val
            420                 425                 430

Asn Asp Leu Ile Ser Pro Pro Ser Gly Ala Pro Leu Ile Ser Ala Leu
        435                 440                 445
```

Gly Asp Leu Gly Gly Phe Thr His Ala Asp Val Thr Ala Val Pro Ser
        450                 455                 460

Thr Ile Phe Thr Ser Pro Val Phe Thr Thr Gly Thr Ser Val Asp Tyr
465                 470                 475                 480

Ala Glu Leu Asn Pro Ser Ile Ile Val Arg Ala Gly Ser Phe Asp Pro
                485                 490                 495

Ser Ser Gln Pro Asn Asp Arg His Val Ala Phe Ser Thr Asp Gly Gly
            500                 505                 510

Lys Asn Trp Phe Gln Gly Ser Glu Pro Gly Gly Val Thr Thr Gly Gly
        515                 520                 525

Thr Val Ala Ala Ser Ala Asp Gly Ser Arg Phe Val Trp Ala Pro Gly
        530                 535                 540

Asp Pro Gly Gln Pro Val Val Tyr Ala Val Gly Phe Gly Asn Ser Trp
545                 550                 555                 560

Ala Ala Ser Gln Gly Val Pro Ala Asn Ala Gln Ile Arg Ser Asp Arg
                565                 570                 575

Val Asn Pro Lys Thr Phe Tyr Ala Leu Ser Asn Gly Thr Phe Tyr Arg
            580                 585                 590

Ser Thr Asp Gly Gly Val Thr Phe Gln Pro Val Ala Ala Gly Leu Pro
        595                 600                 605

Ser Ser Gly Ala Val Gly Val Met Phe His Ala Val Pro Gly Lys Glu
        610                 615                 620

Gly Asp Leu Trp Leu Ala Ala Ser Ser Gly Leu Tyr His Ser Thr Asn
625                 630                 635                 640

Gly Gly Ser Ser Trp Ser Ala Ile Thr Gly Val Ser Ser Ala Val Asn
                645                 650                 655

Val Gly Phe Gly Lys Ser Ala Pro Gly Ser Ser Tyr Pro Ala Val Phe
            660                 665                 670

Val Val Gly Thr Ile Gly Gly Val Thr Gly Ala Tyr Arg Ser Asp Asp
        675                 680                 685

Gly Gly Thr Thr Trp Val Arg Ile Asn Asp Asp Gln His Gln Tyr Gly
        690                 695                 700

Asn Trp Gly Gln Ala Ile Thr Gly Asp Pro Arg Ile Tyr Gly Arg Val
705                 710                 715                 720

Tyr Ile Gly Thr Asn Gly Arg Gly Ile Val Tyr Gly Asp Ile Gly Gly
                725                 730                 735

Ala Pro Ser Gly Ser
        740

<210> SEQ ID NO 11
<211> LENGTH: 1293
<212> TYPE: DNA
<213> ORGANISM: Artificial Sequence
<220> FEATURE:
<223> OTHER INFORMATION: endoglucanase nucleotide derived from
      Thermobifida fusca

<400> SEQUENCE: 11
gccggtctca ccgccacagt caccaaagaa tcctcgtggg acaacggcta ctccgcgtcc      60
gtcaccgtcc gcaacgacac ctcgagcacc gtctcccagt gggaggtcgt cctcaccctg     120
cccggcggca ctacagtggc ccaggtgtgg aacgcccagc acaccagcag cggcaactcc     180
cacaccttca ccggggtttc ctggaacagc accatcccgc ccggaggcac cgcctcttcc     240
ggcttcatcg cttccggcag cggcgaaccc acccactgca ccatcaacgg cgcccccctgc    300 gacgaaggct ccgagccggg cggccccggc ggtcccggaa cccccctccc cgaccccggc     360

```
acgcagcccg gcaccggcac cccggtcgag cggtacggca aagtccaggt ctgcggcacc      420
cagctctgcg acgagcacgg caacccggtc caactgcgcg gcatgagcac ccacggcatc      480
cagtggttcg accactgcct gaccgacagc tcgctggacg ccctggccta cgactggaag      540
gccgacatca tccgcctgtc catgtacatc caggaagacg gctacgagac caacccgcgc      600
ggcttcaccg accggatgca ccagctcatc gacatggcca cggcgcgcgg cctgtacgtg      660
atcgtggact ggcacatcct caccccgggc gatccccact acaacctgga ccgggccaag      720
accttcttcg cggaaatcgc ccagcgccac gccagcaaga ccaacgtgct ctacgagatc      780
gccaacgaac ccaacggagt gagctgggcc tccatcaaga gctacgccga agaggtcatc      840
ccggtgatcc gccagcgcga ccccgactcg gtgatcatcg tgggcacccg cggctggtcg      900
tcgctcggcg tctccgaagg ctccggcccc gccgagatcc cggccaaccc ggtcaacgcc      960
tccaacatca tgtacgcctt ccacttctac gcggcctcgc accgcgacaa ctacctcaac     1020
gcgctgcgtg aggcctccga gctgttcccg gtcttcgtca ccgagttcgg caccgagacc     1080
tacaccggtg acggcgccaa cgacttccag atggccgacc gctacatcga cctgatggcg     1140
gaacggaaga tcgggtggac caagtggaac tactcggacg acttccgttc cggcgcggtc     1200
ttccagccgg gcacctgcgc gtccggcggc ccgtggagcg gttcgtcgct gaaggcgtcc     1260
ggacagtggg tgcggagcaa gctccagtcc tga                                  1293
```

<210> SEQ ID NO 12
<211> LENGTH: 430
<212> TYPE: PRT
<213> ORGANISM: Artificial Sequence
<220> FEATURE:
<223> OTHER INFORMATION: endoglucanase derived from Thermobifida fusca

<400> SEQUENCE: 12

```
Ala Gly Leu Thr Ala Thr Val Thr Lys Glu Ser Ser Trp Asp Asn Gly
1               5                   10                  15

Tyr Ser Ala Ser Val Thr Val Arg Asn Asp Thr Ser Ser Thr Val Ser
            20                  25                  30

Gln Trp Glu Val Val Leu Thr Leu Pro Gly Gly Thr Thr Val Ala Gln
        35                  40                  45

Val Trp Asn Ala Gln His Thr Ser Ser Gly Asn Ser His Thr Phe Thr
    50                  55                  60

Gly Val Ser Trp Asn Ser Thr Ile Pro Pro Gly Gly Thr Ala Ser Ser
65                  70                  75                  80

Gly Phe Ile Ala Ser Gly Ser Gly Glu Pro Thr His Cys Thr Ile Asn
                85                  90                  95

Gly Ala Pro Cys Asp Glu Gly Ser Glu Pro Gly Gly Pro Gly Gly Pro
            100                 105                 110

Gly Thr Pro Ser Pro Asp Pro Gly Thr Gln Pro Gly Thr Gly Thr Pro
        115                 120                 125

Val Glu Arg Tyr Gly Lys Val Gln Val Cys Gly Thr Gln Leu Cys Asp
    130                 135                 140

Glu His Gly Asn Pro Val Gln Leu Arg Gly Met Ser Thr His Gly Ile
145                 150                 155                 160

Gln Trp Phe Asp His Cys Leu Thr Asp Ser Ser Leu Asp Ala Leu Ala
                165                 170                 175

Tyr Asp Trp Lys Ala Asp Ile Ile Arg Leu Ser Met Tyr Ile Gln Glu
            180                 185                 190

Asp Gly Tyr Glu Thr Asn Pro Arg Gly Phe Thr Asp Arg Met His Gln
```

Leu Ile Asp Met Ala Thr Ala Arg Gly Leu Tyr Val Ile Val Asp Trp
    210                 215                 220
His Ile Leu Thr Pro Gly Asp Pro His Tyr Asn Leu Asp Arg Ala Lys
225                 230                 235                 240
Thr Phe Phe Ala Glu Ile Ala Gln Arg His Ala Ser Lys Thr Asn Val
                245                 250                 255
Leu Tyr Glu Ile Ala Asn Glu Pro Asn Gly Val Ser Trp Ala Ser Ile
            260                 265                 270
Lys Ser Tyr Ala Glu Glu Val Ile Pro Val Ile Arg Gln Arg Asp Pro
        275                 280                 285
Asp Ser Val Ile Ile Val Gly Thr Arg Gly Trp Ser Ser Leu Gly Val
    290                 295                 300
Ser Glu Gly Ser Gly Pro Ala Glu Ile Ala Ala Asn Pro Val Asn Ala
305                 310                 315                 320
Ser Asn Ile Met Tyr Ala Phe His Phe Tyr Ala Ser His Arg Asp
                325                 330                 335
Asn Tyr Leu Asn Ala Leu Arg Glu Ala Ser Glu Leu Phe Pro Val Phe
            340                 345                 350
Val Thr Glu Phe Gly Thr Glu Thr Tyr Thr Gly Asp Gly Ala Asn Asp
        355                 360                 365
Phe Gln Met Ala Asp Arg Tyr Ile Asp Leu Met Ala Glu Arg Lys Ile
    370                 375                 380
Gly Trp Thr Lys Trp Asn Tyr Ser Asp Asp Phe Arg Ser Gly Ala Val
385                 390                 395                 400
Phe Gln Pro Gly Thr Cys Ala Ser Gly Gly Pro Trp Ser Gly Ser Ser
                405                 410                 415
Leu Lys Ala Ser Gly Gln Trp Val Arg Ser Lys Leu Gln Ser
            420                 425                 430

<210> SEQ ID NO 13
<211> LENGTH: 2656
<212> TYPE: DNA
<213> ORGANISM: Artificial Sequence
<220> FEATURE:
<223> OTHER INFORMATION: fusion construct

<400> SEQUENCE: 13
atgtatcgga agttggccgt catctcggcc ttcttggcca cagctcgtgc tcagtcggcc    60
tgcactctcc aatcggagac tcacccgcct ctgacatggc agaaatgctc gtctggtggc   120
acttgcactc aacagacagg ctccgtggtc atcgacgcca actggcgctg gactcacgct   180
acgaacagca gcacgaactg ctacgatggc aacacttgga gctcgaccct atgtcctgac   240
aacgagacct gcgcgaagaa ctgctgtctg acggtgccg cctacgcgtc cacgtacgga   300
gttaccacga gcggtaacag cctctccatt ggctttgtca cccagtctgc gcagaagaac   360
gttggcgctc gcctttacct tatggcgagc gacacgacct accaggaatt caccctgctt   420
ggcaacgagt tctctttcga tgttgatgtt tcgcagctgc cgtaagtgac ttaccatgaa   480 ccccctgacgt atcttcttgt gggctcccag ctgactggcc aatttaaggt gcggcttgaa   540
cggagctctc tacttcgtgt ccatggacgc ggatggtggc gtgagcaagt atcccaccaa   600
caccgctggc gccaagtacg gcacggggta ctgtgacagc cagtgtcccc gcgatctgaa   660
gttcatcaat ggccaggcca acgttgaggg ctggagccg tcatccaaca acgcaaacac   720
gggcattgga ggacacggaa gctgctgctc tgagatggat atctgggagg ccaactccat   780

```
ctccgaggct cttacccccc acccttgcac gactgtcggc caggagatct gcgagggtga    840
tgggtgcggc ggaacttact ccgataacag atatggcggc acttgcgatc ccgatggctg    900
cgactggaac ccataccgcc tgggcaacac cagcttctac ggccctggct caagctttac    960
cctcgatacc accaagaaat tgaccgttgt cacccagttc gagacgtcgg gtgccatcaa   1020
ccgatactat gtccagaatg gcgtcacttt ccagcagccc aacgccgagc ttggtagtta   1080
ctctggcaac gagctcaacg atgattactg cacagctgag gaggcagaat cggcggatc   1140
ctctttctca gacaagggcg gcctgactca gttcaagaag ctacctctg gcggcatggt   1200
tctggtcatg agtctgtggg atgatgtgag tttgatggca aaacatgcgc gttgacaaag   1260
agtcaagcag ctgactgaga tgttacagta ctacgccaac atgctgtggc tggactccac   1320
ctacccgaca aacgagacct cctccacacc cggtgccgtg cgcggaagct gctccaccag   1380
ctccggtgtc cctgctcagg tcgaatctca gtctcccaac gccaaggtca ccttctccaa   1440
catcaagttc ggacccattg gcagcaccgg caacccctagc ggcggcaacc ctcccggcgg   1500
aaaccgcct ggcaccacca ccacccgccg cccagccact accactggaa gctctcccgg   1560
acctactagt aagcgggcgg gcggcggcta ttggcacacg agcggccggg agatcctgga   1620
cgcgaacaac gtgccggtac ggatcgccgg catcaactgg tttgggttcg aaacctgcaa   1680
ttacgtcgtg cacggtctct ggtcacgcga ctaccgcagc atgctcgacc agataaagtc   1740
gctcggctac aacacaatcc ggctgccgta ctctgacgac attctcaagc cgggcaccat   1800
gccgaacagc atcaattttt accagatgaa tcaggacctg cagggtctga cgtccttgca   1860
ggtcatggac aaaatcgtcg cgtacgccgg tcagatcggc ctgcgcatca ttcttgaccg   1920
ccaccgaccg gattgcagcg ggcagtcggc gctgtggtac acgagcagcg tctcggaggc   1980
tacgtggatt tccgacctgc aagcgctggc gcagcgctac aagggaaacc cgacggtcgt   2040
cggcttgac ttgcacaacg agccgcatga cccggcctgc tggggctgcg gcgatccgag   2100
catcgactgg cgattggccg ccgagcgggc cggaaacgcc gtgctctcgg tgaatccgaa   2160
cctgctcatt ttcgtcgaag gtgtgcagag ctacaacgga gactcctact ggtggggcgg   2220
caacctgcaa ggagccggcc agtacccggt cgtgctgaac gtgccgaacc gcctggtgta   2280
ctcggcgcac gactacgcga cgagcgtcta cccgcagacg tggttcagcg atccgacctt   2340
ccccaacaac atgcccggca tctggaacaa gaactgggga tacctcttca atcagaacat   2400
tgcaccggta tggctgggcg aattcggtac gacactgcaa tccacgaccg accagacgtg   2460
gctgaagacg ctcgtccagt acctacgccc gaccgcgcaa tacggtgcgg acagcttcca   2520
gtggacctc tggtcctgga accccgattc cggcgacaca ggaggaattc tcaaggatga   2580
ctggcagacg tcgacacag taaaagacgg ctatctcgcg ccgatcaagt cgtcgatttt   2640
cgatcctgtc ggctaa                                                   2656
```

<210> SEQ ID NO 14
<211> LENGTH: 839
<212> TYPE: PRT
<213> ORGANISM: Artificial Sequence
<220> FEATURE:
<223> OTHER INFORMATION: fusion construct

<400> SEQUENCE: 14

Met Tyr Arg Lys Leu Ala Val Ile Ser Ala Pro Leu Ala Thr Ala Arg
1               5                   10                  15

Ala Gln Ser Ala Cys Thr Leu Gln Ser Glu Thr His Pro Pro Leu Thr
            20                  25                  30

-continued

```
Trp Gln Lys Cys Ser Ser Gly Gly Thr Cys Thr Gln Thr Gly Ser
     35                  40                  45
Val Val Ile Asp Ala Asn Trp Arg Trp Thr His Ala Thr Asn Ser Ser
 50                  55                  60
Thr Asn Cys Tyr Asp Gly Asn Thr Trp Ser Ser Thr Leu Cys Pro Asp
 65                  70                  75                  80
Asn Glu Thr Cys Ala Lys Asn Cys Cys Leu Asp Gly Ala Ala Tyr Ala
                 85                  90                  95
Ser Thr Tyr Gly Val Thr Thr Ser Gly Asn Ser Leu Ser Ile Gly Phe
                100                 105                 110
Val Thr Gln Ser Ala Gln Lys Asn Val Gly Ala Arg Leu Tyr Leu Met
                115                 120                 125
Ala Ser Asp Thr Thr Tyr Gln Glu Phe Thr Leu Leu Gly Asn Glu Phe
            130                 135                 140
Ser Phe Asp Val Asp Val Ser Gln Leu Pro Cys Gly Leu Asn Gly Ala
145                 150                 155                 160
Leu Tyr Phe Val Ser Met Asp Ala Asp Gly Val Ser Lys Tyr Pro
                165                 170                 175
Thr Asn Thr Ala Gly Ala Lys Tyr Gly Thr Gly Tyr Cys Asp Ser Gln
            180                 185                 190
Cys Pro Arg Asp Leu Lys Phe Ile Asn Gly Gln Ala Asn Val Glu Gly
            195                 200                 205
Trp Glu Pro Ser Ser Asn Asn Ala Asn Thr Gly Ile Gly Gly His Gly
        210                 215                 220
Ser Cys Cys Ser Glu Met Asp Ile Trp Glu Ala Asn Ser Ile Ser Glu
225                 230                 235                 240
Ala Leu Thr Pro His Pro Cys Thr Thr Val Gly Gln Glu Ile Cys Glu
                245                 250                 255
Gly Asp Gly Cys Gly Gly Thr Tyr Ser Asp Asn Arg Tyr Gly Gly Thr
            260                 265                 270
Cys Asp Pro Asp Gly Cys Asp Trp Asn Pro Tyr Arg Leu Gly Asn Thr
        275                 280                 285
Ser Phe Tyr Gly Pro Gly Ser Ser Phe Thr Leu Asp Thr Thr Lys Lys
    290                 295                 300
Leu Thr Val Val Thr Gln Phe Glu Thr Ser Gly Ala Ile Asn Arg Tyr
305                 310                 315                 320
Tyr Val Gln Asn Gly Val Thr Phe Gln Gln Pro Asn Ala Glu Leu Gly
                325                 330                 335
Ser Tyr Ser Gly Asn Glu Leu Asn Asp Asp Tyr Cys Thr Ala Glu Glu
            340                 345                 350
Ala Glu Phe Gly Gly Ser Ser Phe Ser Asp Lys Gly Gly Leu Thr Gln
        355                 360                 365
Phe Lys Lys Ala Thr Ser Gly Gly Met Val Leu Val Met Ser Leu Trp
    370                 375                 380
Asp Asp Tyr Tyr Ala Asn Met Leu Trp Leu Asp Ser Thr Tyr Pro Thr
385                 390                 395                 400
Asn Glu Thr Ser Ser Thr Pro Gly Ala Val Arg Gly Ser Cys Ser Thr
                405                 410                 415
Ser Ser Gly Val Pro Ala Gln Val Glu Ser Gln Ser Pro Asn Ala Lys
            420                 425                 430
Val Thr Phe Ser Asn Ile Lys Phe Gly Pro Ile Gly Ser Thr Gly Asn
        435                 440                 445
Pro Ser Gly Gly Asn Pro Pro Gly Gly Asn Pro Pro Gly Thr Met Arg
    450                 455                 460
```

Arg Pro Ala Thr Thr Thr Gly Ser Ser Pro Gly Pro Thr Ser Lys Arg
465                 470                 475                 480

Ala Gly Gly Gly Tyr Trp His Thr Ser Gly Arg Glu Ile Leu Asp Ala
            485                 490                 495

Asn Asn Val Pro Val Arg Ile Ala Gly Ile Asn Trp Phe Gly Phe Glu
        500                 505                 510

Thr Cys Asn Tyr Val Val His Gly Leu Trp Ser Arg Asp Tyr Arg Ser
    515                 520                 525

Met Leu Asp Gln Ile Lys Ser Leu Gly Tyr Asn Thr Ile Arg Leu Pro
530                 535                 540

Tyr Ser Asp Asp Ile Leu Lys Pro Gly Thr Met Pro Asn Ser Ile Asn
545                 550                 555                 560

Phe Tyr Gln Met Asn Gln Asp Leu Gln Gly Leu Thr Ser Leu Gln Val
                565                 570                 575

Met Asp Lys Ile Val Ala Tyr Ala Gly Gln Ile Gly Leu Arg Ile Ile
            580                 585                 590

Leu Asp Arg His Arg Pro Asp Cys Ser Gly Gln Ser Ala Leu Trp Tyr
        595                 600                 605

Thr Ser Ser Val Ser Glu Ala Thr Trp Ile Ser Asp Leu Gln Ala Leu
    610                 615                 620

Ala Gln Arg Tyr Lys Gly Asn Pro Thr Val Val Gly Phe Asp Leu His
625                 630                 635                 640

Asn Glu Pro His Asp Pro Ala Cys Trp Gly Cys Gly Asp Pro Ser Ile
                645                 650                 655

Asp Trp Arg Leu Ala Ala Glu Arg Ala Gly Asn Ala Val Leu Ser Val
            660                 665                 670

Asn Pro Asn Leu Leu Ile Phe Val Glu Gly Val Gln Ser Tyr Asn Gly
        675                 680                 685

Asp Ser Tyr Trp Trp Gly Gly Asn Leu Gln Gly Ala Gly Gln Tyr Pro
    690                 695                 700

Val Val Leu Asn Val Pro Asn Arg Leu Val Tyr Ser Ala His Asp Tyr
705                 710                 715                 720

Ala Thr Ser Val Tyr Pro Gln Thr Trp Phe Ser Asp Pro Thr Phe Pro
                725                 730                 735

Asn Asn Trp Gly Ile Trp Asn Lys Asn Trp Gly Tyr Leu Ile Phe Asn
            740                 745                 750

Gln Asn Ile Ala Pro Val Trp Leu Gly Glu Phe Gly Thr Thr Leu Gln
        755                 760                 765

Ser Thr Thr Asp Gln Thr Trp Leu Lys Thr Leu Val Gln Tyr Leu Arg
    770                 775                 780

Pro Thr Ala Gln Tyr Gly Ala Asp Ser Phe Gln Trp Thr Phe Trp Ser
785                 790                 795                 800

Trp Asn Pro Asp Ser Gly Asp Thr Gly Gly Ile Leu Lys Asp Asp Trp
                805                 810                 815

Gln Thr Val Asp Thr Val Lys Asp Gly Tyr Leu Ala Pro Ile Lys Ser
            820                 825                 830

Ser Ile Phe Asp Pro Val Gly
        835

<210> SEQ ID NO 15
<211> LENGTH: 10244
<212> TYPE: DNA
<213> ORGANISM: Artificial Sequence
<220> FEATURE:
<223> OTHER INFORMATION: pTrex4 plasmid construct

```
<400> SEQUENCE: 15
aagcttaact agtacttctc gagctctgta catgtccggt cgcgacgtac gcgtatcgat      60
ggcgccagct gcaggcggcc gcctgcagcc acttgcagtc ccgtggaatt ctcacggtga     120
atgtaggcct tttgtagggt aggaattgtc actcaagcac ccccaacctc cattacgcct     180
cccccataga gttcccaatc agtgagtcat ggcactgttc tcaaatagat tggggagaag     240
ttgacttccg cccagagctg aaggtcgcac aaccgcatga tatagggtcg gcaacggcaa     300
aaaagcacgt ggctcaccga aaagcaagat gtttgcgatc taacatccag gaacctggat     360
acatccatca tcacgcacga ccactttgat ctgctggtaa actcgtattc gccctaaacc     420
gaagtgacgt ggtaaatcta cacgtgggcc ccttttcggta tactgcgtgt gtcttctcta     480
ggtgccattc ttttcccttc ctctagtgtt gaattgtttg tgttggagtc cgagctgtaa     540
ctacctctga atctctggag aatggtggac taacgactac cgtgcacctg catcatgtat     600
ataatagtga tcctgagaag gggggtttgg agcaatgtgg gactttgatg gtcatcaaac     660
aaagaacgaa gacgcctctt ttgcaaagtt ttgtttcggc tacggtgaag aactggatac     720
ttgttgtgtc ttctgtgtat ttttgtctgc aacaagaggc cagagacaat ctattcaaac     780
accaagcttg ctcttttgag ctacaagaac ctgtggggta tatatctaga gttgtgaagt     840
cggtaatccc gctgtatagt aatacgagtc gcatctaaat actccgaagc tgctgcgaac     900
ccggagaatc gagatgtgct ggaaagcttc tagcgagcgg ctaaattagc atgaaaggct     960
atgagaaatt ctggagacgg cttgttgaat catggcgttc cattcttcga caagcaaagc    1020
gttccgtcgc agtagcaggc actcattccc gaaaaaactc ggagattcct aagtagcgat    1080
ggaaccggaa taatataata ggcaatacat tgagttgcct cgacggttgc aatgcagggg    1140
tactgagctt ggacataact gttccgtacc ccacctcttc tcaacctttg ggcgtttccc    1200
tgattcagcg tacccgtaca agtcgtaatc actattaacc cagactgacc ggacgtgttt    1260
tgcccttcat ttggagaaat aatgtcattg cgatgtgtaa tttgcctgct tgaccgactg    1320
gggctgttcg aagcccgaat gtaggattgt tatccgaact ctgctcgtag aggcatgttg    1380
tgaatctgtg tcgggcagga cacgcctcga aggttcacgg caagggaaac caccgatagc    1440
agtgtctagt agcaacctgt aaagccgcaa tgcagcatca ctggaaaata caaaccaatc    1500
tgctaaaagt acataagtta atgcctaaag aagtcatata ccagcggcta ataattgtac    1560
aatcaagtgg ctaaacgtac cgtaatttgc caacggcttg tggggttgca gaagcaacgg    1620
caaagcccca cttccccacg tttgtttctt cactcagtcc aatctcagct ggtgatcccc    1680
caattgggtc gcttgtttgt tccggtgaag tgaaagaaga cagaggtaag aatgtctgac    1740
tcggagcgtt ttgcatacaa ccaagggcag tgatggaaga cagtgaaatg ttgacattca    1800
aggagtattt agccagggat gcttgagtgt atcgtgtaag gaggtttgtc tgccgatacg    1860
acgaatactg tatagtcact tctgatgaag tggtccatat tgaaatgtaa gtcggcactg    1920
aacaggcaaa agattgagtt gaaactgcct aagatctcgg gccctcgggc cttcggcctt    1980
tgggtgtaca tgtttgtgct ccgggcaaat gcaaagtgtg gtaggatcga acacactgct    2040
gcctttacca agcagctgag ggtatgtgat aggcaaatgt tcagggcca ctgcatggtt    2100 tcgaatagaa agagaagctt agccaagaac aatagccgat aaagatagcc tcattaaacg    2160
gaatgagcta gtaggcaaag tcagcgaatg tgtatatata aggttcgag  gtccgtgcct    2220 ccctcatgct ctccccatct actcatcaac tcagatcctc caggagactt gtacaccatc    2280
ttttgaggca cagaaaccca atagtcaacc gcggactgcg catcatgtat cggaagttgg    2340
```

```
ccgtcatctc ggccttcttg gccacagctc gtgctcagtc ggcctgcact ctccaatcgg   2400
agactcaccc gcctctgaca tggcagaaat gctcgtctgg tggcacttgc actcaacaga   2460
caggctccgt ggtcatcgac gccaactggc gctggactca cgctacgaac agcagcacga   2520
actgctacga tggcaacact tggagctcga ccctatgtcc tgacaacgag acctgcgcga   2580
agaactgctg tctggacggt gccgcctacg cgtccacgta cggagttacc acgagcggta   2640
acagcctctc cattggcttt gtcacccagt ctgcgcagaa aacgttggc gctcgccttt   2700 accttatggc gagcgacacg acctaccagg aattcaccct gcttggcaac gagttctctt   2760
tcgatgttga tgtttcgcag ctgccgtaag tgacttacca tcaaccctg acgtatcttc   2820 ttgtgggctc ccagctgact ggccaattta aggtgcggct gaacggagc tctctacttc   2880 gtgtccatgg acgcggatgg tggcgtgagc aagtatccca ccaacaccgc tggcgccaag   2940
tacggcacgg ggtactgtga cagccagtgt ccccgcgatc tgaagttcat caatggccag   3000
gccaacgttg agggctggga gccgtcatcc aacaacgcaa acacgggcat ggaggacac    3060 ggaagctgct gctctgagat ggatatctgg gaggccaact ccatctccga ggctcttacc   3120 cccccacccttt gcacgactgt cggccaggag atctgcgagg gtgatgggtg cggcggaact  3180
tactccgata acagatatgg cggcacttgc gatcccgatg gctgcgactg aacccatac    3240 cgcctgggca acaccagctt ctacggccct ggctcaagct ttaccctcga taccaccaag   3300
aaattgaccg ttgtcaccca gttcgagacg tcgggtgcca tcaaccgata ctatgtccag   3360
aatggcgtca ctttccagca gcccaacgcc gagcttggta gttactctgg caacgagctc   3420
aacgatgatt actgcacagc tgaggaggca gaattcggcg gatcctcttt ctcagacaag   3480
ggcggcctga ctcagttcaa gaaggctacc tctggcggca tggttctggt catgagtctg   3540
tgggatgatg tgagtttgat ggacaaacat gcgcgttgac aaagagtcaa gcagctgact   3600
gagatgttac agtactacgc caacatgctg tggctggact ccacctaccc gacaaacgag   3660
acctcctcca cacccggtgc cgtgcgcgga agctgctcca ccagctccgg tgtccctgct   3720
caggtcgaat ctcagtctcc caacgccaag gtcaccttct ccaacatcaa gttcggaccc   3780
attggcagca ccggcaaccc tagcggcggc aaccctcccg gcggaaaccc gcctggcacc   3840
accaccaccc gccgcccagc cactaccact ggaagctctc ccggacctac tagtaagcgg   3900
ataaggcgcg ccgcgcgcca gctccgtgcg aaagcctgac gcaccggtag attcttggtg   3960
agcccgtatc atgacggcgg cgggagctac atggccccgg gtgatttatt ttttttgtat   4020
ctacttctga cccttttcaa atatacggtc aactcatctt tcactggaga tgcggcctgc   4080
ttggtattgc gatgttgtca gcttggcaaa ttgtggcttt cgaaaacaca aaacgattcc   4140
ttagtagcca tgcattttaa gataacggaa tagaagaaag aggaaattaa aaaaaaaaa    4200 aaaacaaaca tcccgttcat aaccgtagta atcgccgctc ttcgtgtatc ccagtaccag   4260
tttattttga atagctcgcc cgctggagag catcctgaat gcaagtaaca accgtagagg   4320
ctgacacggc aggtgttgct agggagcgtc gtgttctaca aggccagacg tcttcgcggt   4380
tgatatatat gtatgtttga ctgcaggctg ctcagcgacg acagtcaagt tcgccctcgc   4440
tgcttgtgca ataatcgcag tggggaagcc acaccgtgac tcccatcttt cagtaaagct   4500
ctgttggtgt ttatcagcaa tacacgtaat ttaaactcgt tagcatgggg ctgatagctt   4560
aattaccgtt taccagtgcc gcggttctgc agctttcctt ggcccgtaaa attcggcgaa   4620
gccagccaat caccagctag gcaccagcta aaccctataa ttagtctctt atcaaccaca   4680
tccgctcccc cgggatcaat gaggagaatg aggggggatgc ggggctaaac aagcctacat   4740
```

```
aaccctcatg ccaactccca gtttacactc gtcgagccaa catcctgact ataagctaac    4800
acagaatgcc tcaatcctgg gaagaactgg ccgctgataa gcgcgcccgc ctcgcaaaaa    4860
ccatccctga tgaatggaaa gtccagacgc tgcctgcgga agacagcgtt attgatttcc    4920
caaagaaatc ggggatcctt tcagaggccg aactgaagat cacagaggcc tccgctgcag    4980
atcttgtgtc caagctggcg gccggagagt tgacctcggt ggaagttacg ctagcattct    5040
gtaaacgggc agcaatcgcc cagcagttag tagggtcccc tctacctctc agggagatgt    5100
aacaacgcca ccttatggga ctatcaagct gacgctggct tctgtgcaga caaactgcgc    5160
ccacgagttc ttccctgacg ccgctctcgc gcaggcaagg gaactcgatg aatactacgc    5220
aaagcacaag agacccgttg gtccactcca tggcctcccc atctctctca aagaccagct    5280
tcgagtcaag gtacaccgtt gcccctaagt cgttagatgt cccttttgt cagctaacat     5340
atgccaccag ggctacgaaa catcaatggg ctacatctca tggctaaaca agtacgacga    5400
aggggactcg gttctgacaa ccatgctccg caaagccggt gccgtcttct acgtcaagac    5460
ctctgtcccg cagaccctga tggtctgcga gacagtcaac aacatcatcg ggcgcaccgt    5520
caacccacgc aacaagaact ggtcgtgcgg cggcagttct ggtggtgagg gtgcgatcgt    5580
tgggattcgt ggtggcgtca tcggtgtagg aacggatatc ggtggctcga ttcgagtgcc    5640
ggccgcgttc aacttcctgt acggtctaag gccgagtcat gggcggctgc cgtatgcaaa    5700
gatggcgaac agcatggagg gtcaggagac ggtgcacagc gttgtcgggc cgattacgca    5760
ctctgttgag ggtgagtcct tcgcctcttc cttcttttcc tgctctatac caggcctcca    5820
ctgtcctcct ttcttgcttt ttatactata tacgagaccg gcagtcactg atgaagtatg    5880
ttagacctcc gcctcttcac caaatccgtc tcggtcagg agccatggaa atacgactcc      5940
aaggtcatcc ccatgccctg gcgccagtcc gagtcggaca ttattgcctc caagatcaag    6000
aacgcgggc tcaatatcgg ctactacaac ttcgacggca atgtccttcc acaccctcct     6060
atcctgcgcg gcgtggaaac caccgtcgcc gcactcgcca aagccggtca caccgtgacc    6120
ccgtggacgc catacaagca cgatttcggc cacgatctca tctcccatat ctacgcggct    6180
gacggcagcg ccgacgtaat gcgcgatatc agtgcatccg gcgagccggc gattccaaat    6240
atcaaagacc tactgaaccc gaacatcaaa gctgttaaca tgaacgagct ctgggacacg    6300
catctccaga agtggaatta ccagatggag taccttgaga aatggcggga ggctgaagaa    6360
aaggccggga aggaactgga cgccatcatc gcgccgatta cgcctaccgc tgcggtacgg    6420
catgaccagt tccggtacta tgggtatgcc tctgtgatca acctgctgga tttcacgagc    6480
gtggttgttc cggttacctt tgcggataag aacatcgata agaagaatga gagtttcaag    6540
gcggttagtg agcttgatgc cctcgtgcag gaagagtatg atccggaggc gtaccatggg    6600
gcaccggttg cagtgcaggt tatcggacgg agactcagtg aagagaggac gttggcgatt    6660
gcagaggaag tggggaagtt gctgggaaat gtggtgactc catagctaat aagtgtcaga    6720
tagcaatttg cacaagaaat caataccagc aactgtaaat aagcgctgaa gtgaccatgc    6780
catgctacga aagagcagaa aaaacctgcc gtagaaccg aagagatatg acacgcttcc      6840
atctctcaaa ggaagaatcc cttcagggtt gcgtttccag tctagacacg tataacggca    6900
caagtgtctc tcaccaaatg ggttatatct caaatgtgat ctaaggatgg aaagcccaga    6960
atctaggcct attaatattc cggagtatac gtagccggct aacgttaaca accggtacct    7020
ctagaactat agctagcatg cgcaaattta aagcgctgat atcgatcgcg cgcagatcca    7080
tatatagggc ccgggttata attacctcag gtcgacgtcc catggccatt cgaattcgta    7140
```

```
atcatggtca tagctgtttc ctgtgtgaaa ttgttatccg ctcacaattc cacacaacat    7200
acgagccgga agcataaagt gtaaagcctg gggtgcctaa tgagtgagct aactcacatt    7260
aattgcgttg cgctcactgc ccgctttcca gtcgggaaac ctgtcgtgcc agctgcatta    7320
atgaatcggc caacgcgcgg ggagaggcgg tttgcgtatt gggcgctctt ccgcttcctc    7380
gctcactgac tcgctgcgct cggtcgttcg gctgcggcga gcggtatcag ctcactcaaa    7440
ggcggtaata cggttatcca cagaatcagg ggataacgca ggaaagaaca tgtgagcaaa    7500
aggccagcaa aaggccagga accgtaaaaa ggccgcgttg ctggcgtttt tccataggct    7560
ccgcccccct gacgagcatc acaaaaatcg acgctcaagt cagaggtggc gaaacccgac    7620
aggactataa agataccagg cgtttccccc tggaagctcc ctcgtgcgct ctcctgttcc    7680
gaccctgccg cttaccggat acctgtccgc ctttctccct tcgggaagcg tggcgctttc    7740
tcatagctca cgctgtaggt atctcagttc ggtgtaggtc gttcgctcca agctgggctg    7800
tgtgcacgaa ccccccgttc agcccgaccg ctgcgcctta ccggtaact atcgtcttga    7860 gtccaacccg gtaagacacg acttatcgcc actggcagca gccactggta acaggattag    7920
cagagcgagg tatgtaggcg gtgctacaga gttcttgaag tggtggccta actacggcta    7980
cactagaaga acagtatttg gtatctgcgc tctgctgaag ccagttacct tcggaaaaag    8040
agttggtagc tcttgatccg gcaaacaaac caccgctggt agcggtggtt tttttgtttg    8100
caagcagcag attacgcgca gaaaaaaagg atctcaagaa gatcctttga tcttttctac    8160
ggggtctgac gctcagtgga acgaaaactc acgttaaggg attttggtca tgagattatc    8220
aaaaaggatc ttcacctaga tccttttaaa ttaaaaatga agttttaaat caatctaaag    8280
tatatatgag taaacttggt ctgacagtta ccaatgctta atcagtgagg cacctatctc    8340
agcgatctgt ctatttcgtt catccatagt tgcctgactc cccgtcgtgt agataactac    8400
gatacgggag ggcttaccat ctggccccag tgctgcaatg ataccgcgag acccacgctc    8460
accggctcca gatttatcag caataaacca gccagccgga agggccgagc gcagaagtgg    8520
tcctgcaact ttatccgcct ccatccagtc tattaattgt tgccctggaa gctagagtaa    8580
gtagttcgcc agttaatagt ttgcgcaacg ttgttgccat tgctacaggc atcgtggtgt    8640
cacgctcgtc gtttggtatg gcttcattca gctccggttc ccaacgatca aggcgagtta    8700
catgatcccc catgttgtgc aaaaaagcgg ttagctcctt cggtcctccg atcgttgtca    8760
gaagtaagtt ggccgcagtg ttatcactca tggttatggc agcactgcat aattctctta    8820
ctgtcatgcc atccgtaaga tgcttttctg tgactggtga gtactcaacc aagtcattct    8880
gagaatagtg tatgcggcga ccgagttgct cttgcccggc gtcaatacgg gataataccg    8940
cgccacatag cagaacttta aaagtgctca tcattggaaa acgttcttcg gggcgaaaac    9000
tctcaaggat cttaccgctg ttgagatcca gttcgatgta acccactcgt gcacccaact    9060
gatcttcagc atcttttact ttcaccagcg tttctgggtg agcaaaaaca ggaaggcaaa    9120
atgccgcaaa aaagggaata agggcgacac ggaaatgttg aatactcata ctcttccttt    9180
ttcaatatta ttgaagcatt tatcagggtt attgtctcat gagcggatac atatttgaat    9240
gtatttagaa aaataaacaa ataggggttc cgcgcacatt tccccgaaaa gtgccacctg    9300
acgtctaaga aaccattatt atcatgacat taacctataa aaataggcgt atcacgaggc    9360
cctttcgtct cgcgcgtttc ggtgatgacg gtgaaaacct ctgacacatg cagctcccgg    9420
agacggtcac agcttgtctg taagcggatg ccggagcag acaagcccgt cagggcgcgt    9480
cagcgggtgt tggcgggtgt cggggctgg cttaactatg cggcatcaga gcagattgta    9540
```

-continued

```
ctgagagtgc accataaaat tgtaaacgtt aatattttgt taaaattcgc gttaaatttt    9600
tgttaaatca gctcattttt taaccaatag gccgaaatcg gcaaaatccc ttataaatca    9660
aaagaatagc ccgagatagg gttgagtgtt gttccagttt ggaacaagag tccactatta    9720
aagaacgtgg actccaacgt caaagggcga aaaccgtct atcagggcga tggcccacta     9780
cgtgaaccat cacccaaatc aagttttttg gggtcgaggt gccgtaaagc actaaatcgg    9840
aaccctaaag ggagcccccg atttagagct tgacgggaa agccggcgaa cgtggcgaga     9900
aaggaaggga agaaagcgaa aggagcgggc gctagggcgc tggcaagtgt agcggtcacg    9960
ctgcgcgtaa ccaccacacc cgccgcgctt aatgcgccgc tacagggcgc gtactatggt    10020
tgctttgacg tatgcggtgt gaaataccgc acagatgcgt aaggagaaaa taccgcatca    10080
ggcgccattc gccattcagg ctgcgcaact gttgggaagg gcgatcggtg cgggcctctt    10140
cgctattacg ccagctggcg aaaggggat gtgctgcaag gcgattaagt tgggtaacgc     10200
cagggttttc ccagtcacga cgttgtaaaa cgacggccag tgcc                    10244
```

<210> SEQ ID NO 16
<211> LENGTH: 12
<212> TYPE: DNA
<213> ORGANISM: Artificial Sequence
<220> FEATURE:
<223> OTHER INFORMATION: synthetic

<400> SEQUENCE: 16
actagtaagc gg                                                       12

<210> SEQ ID NO 17
<211> LENGTH: 41
<212> TYPE: DNA
<213> ORGANISM: Artificial Sequence
<220> FEATURE:
<223> OTHER INFORMATION: primer

<400> SEQUENCE: 17
gcttatacta gtaagcgcgc gggcggcggc tattggcaca c                       41

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
gcttatggcg cgccttagac aggatcgaaa atcgacgac                          39

<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
ctaagagagc gacgactcag ccgtacacct ggagcaacgt ggc                     43

<210> SEQ ID NO 20
<211> LENGTH: 38
<212> TYPE: DNA
<213> ORGANISM: Artificial Sequence
<220> FEATURE:
<223> OTHER INFORMATION: primer

```
<400> SEQUENCE: 20
ttacgatccg gacggcgcac caccaatgtc cccgtata                                  38

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21
gcttatacta gtaagcgcgc cggtgtcacc gccacagtca cc                             42

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
gcttatggcg cgcctcagga ctggagcttg ctccgc                                    36
```

EXO-ENDO CELLULASE FUSION PROTEIN

RELATED APPLICATIONS

The present application claims priority to U.S. Provisional Patent Application Ser. No. 60/556,598, entitled "Exo-Endo Cellulase Fusion Protein" and filed on Mar. 25, 2004.

SPONSORED RESEARCH AND DEVELOPMENT

Portions of this work were funded by Subcontract No. ZC0-0-30017-01 with the National Renewable Energy Laboratory under Prime Contract No. DE-AC36-99GO10337 with the United States Department of Energy. Accordingly, the United States Government may have certain rights in the invention.

FIELD OF THE INVENTION

The present invention relates to a heterologous exo-endo cellulase fusion construct, which encodes a fusion protein having cellulolytic activity comprising a catalytic domain derived from a fungal exo-cellobiohydrolase and a catalytic domain derived from an endoglucanase. The invention also relates to vectors and fungal host cells comprising the heterologous exo-endo cellulase fusion construct as well as methods for producing a cellulase fusion protein and enzymatic cellulase compositions.

BACKGROUND OF THE INVENTION

Cellulose and hemicellulose are the most abundant plant materials produced by photosynthesis. They can be degraded and used as an energy source by numerous microorganisms, including bacteria, yeast and fungi, which produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG") (Knowles et al., 1987 and Schulein, 1988). Endoglucanases act mainly on the amorphous parts of the cellulose fiber, whereas cellobiohydrolases are also able to degrade crystalline cellulose.

Cellulases are known to be produced by a large number of bacteria, yeast and fungi. Certain fungi produce a complete cellulase system capable of degrading crystalline forms of cellulose, such that the cellulases are readily produced in large quantities via fermentation.

In order to efficiently convert crystalline cellulose to glucose the complete cellulase system comprising components from each of the CBH, EG and BG classifications is required, with isolated components less effective in hydrolyzing crystalline cellulose (Filho et al., 1996). In particular, the combination of EG-type cellulases and CBH-type cellulases interact to more efficiently degrade cellulose than either enzyme used alone (Wood, 1985; Baker et al., 1994; and Nieves et al., 1995).

Additionally, cellulases are known in the art to be useful in the treatment of textiles for the purposes of enhancing the cleaning ability of detergent compositions, for use as a softening agent, for improving the feel and appearance of cotton fabrics, and the like (Kumar et al., 1997). Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757, and GB App. No. 1,358,599), have been described in the literature.

Hence, cellulases produced in fungi and bacteria have received significant attention. In particular, fermentation of Trichoderma spp. (e.g., Trichoderma longibrachiatum or Trichoderma reesei) has been shown to produce a complete cellulase system capable of degrading crystalline forms of cellulose. Over the years, Trichoderma cellulase production has been improved by classical mutagenesis, screening, selection and development of highly refined, large scale inexpensive fermentation conditions. While the multi-component cellulase system of Trichoderma spp. is able to hydrolyze cellulose to glucose, there are cellulases from other microorganisms, particularly bacterial strains, with different properties for efficient cellulose hydrolysis, and it would be advantageous to express these proteins in a filamentous fungus for industrial scale cellulase production. However, the results of many studies demonstrate that the yield of bacterial enzymes from filamentous fungi is low (Jeeves et al., 1991).

In this invention, a heterologous exo-endo cellulase fusion construct, which includes the coding region of a fungal exo-cellobiohydrolase (CBH) catalytic domain and a coding region of an endoglucanase (EG) catalytic domain, has been introduced and expressed in a filamentous fungi host cell to increase the yield and effectiveness of cellulase enzymes.

SUMMARY OF THE INVENTION

In a first aspect, the invention includes a heterologous exo-endo cellulase fusion construct comprising in operable linkage from the 5' end of said construct, (a) a DNA molecule encoding a signal sequence, (b) a DNA molecule encoding a catalytic domain of an exo-cellobiohydrolase, and (c) a DNA molecule encoding an endoglucanase catalytic domain.

In a first embodiment of this aspect, the heterologous exo-endo cellulase fusion construct further comprises a linker sequence located 3' of the catalytic domain of the exo-cellobiohydrolase and 5' of the catalytic domain of the endoglucanase. In a second embodiment, the heterologous exo-endo cellulase fusion construct lacks the cellulose binding domain (CBD) of the exo-cellobiohydrolase. In a third embodiment, the heterologous exo-endo cellulase fusion construct further comprises a kexin site located after the linker sequence and before the coding region of the endoglucanase catalytic domain. In a fourth embodiment, the heterologous exo-endo fusion construct will comprise a promoter of a filamentous fungus secretable protein, said promoter located in operable linkage 5' of the coding region of the exo-cellobiohydrolase catalytic domain. In a fifth embodiment, the promoter is a cbh promoter and preferably a cbh1 promoter derived from T. reesei. In a sixth embodiment, the exo-cellobiohydrolase is a CBH1 and particularly a CBH1 having an amino acid sequence of at least 90% sequence identity with the sequence set forth in SEQ ID NO.: 6. In a seventh embodiment, the endoglucanase catalytic domain is derived from a bacterial endoglucanase. In an eighth embodiment, the bacterial endoglucanase catalytic domain is selected from the group consisting of an Acidothermus cellulolyticus GH5A endoglucanase I (E1) catalytic domain; an *Acidothermus cellulolyticus* GH74 endoglucanase (GH74-EG) catalytic domain: and a *Thermobifida fusca* E5 endoglucanase (Tf-E5) catalytic domain. In a ninth embodiment, the heterologous exo-endo cellulase fusion construct lacks the cellulose binding domain of the endoglucanase. In a tenth embodiment, the endoglucanase is an *Acidothermus cellulolyticus* GH5A E1 and particularly the *Acidothermus cellulolyticus* GH5A E1 having an amino acid sequence of at least 90% sequence identity with the sequence set forth in SEQ ID NO. 8. In an eleventh embodiment, the heterologous exo-endo cellulase fusion construct comprises a terminator sequence located 3' to the endoglucanase catalytic domain. In a twelfth embodiment, the heterologous fusion construct comprises a selectable marker.

In a second aspect, the invention includes a vector comprising in operable linkage a promoter of a filamentous fungus secretable protein, a DNA molecule encoding a signal sequence, a DNA molecule encoding a catalytic domain of a fungal exo-cellobiohydrolase, a DNA molecule encoding a catalytic domain of an endoglucanase, and a terminator. In one embodiment, the vector will further include a selectable marker. In a second embodiment, the vector will comprise a linker located 3' of the exo-cellobiohydrolase (CBH) catalytic domain and 5' of the EG catalytic domain. In a third embodiment, the vector will lack the CBH cellulose binding domain. In a fourth embodiment, the vector will comprise a kexin site. In a fifth embodiment, the catalytic domain of the endoglucanase is derived from a bacterial endoglucanase. In a sixth embodiment, the vector lacks the cellulose binding domain of the endoglucanase.

In a third aspect, the invention includes a fungal host cell transformed with a heterologous exo-endo cellulase fusion construct or a fungal host cell transformed with a vector comprising a heterologous exo-endo cellulase fusion construct.

In a fourth aspect, the invention includes a recombinant fungal cell comprising the heterologous exo-end cellulase fusion construct or a vector comprising the same.

In a particularly preferred embodiment of the third and fourth aspects, the fungal host cell is a *Trichoderma* host cell and more particularly a strain of *T. reesei*. In another embodiment of these aspects, native cellulase genes, such as cbh1, cbh2, egl1 and egl2 have been deleted from the fungal cells. In a third embodiment, the native cellulose binding domain has been deleted from the fungal cells.

In a fifth aspect, the invention includes an isolated cellulase fusion protein having cellulolytic activity which comprises an exo-cellobiohydrolase catalytic domain and an endoglucanase catalytic domain, wherein the exo-cellobiohydrolase lacks a cellulose binding domain. In one embodiment of this aspect, the exo-cellobiohydrolase is a CBH1. In a second embodiment, the catalytic domain of the endoglucanase is derived from a bacterial cell. In a third embodiment, the bacterial cell is a strain of *Acidothermus cellulolyticus*. In a fourth embodiment, the invention concerns a cellulolytic composition comprising the isolated cellulase fusion protein.

In a sixth aspect, the invention includes a method of producing an enzyme having cellulolytic activity comprising, a) stably transforming a filamentous fungal host cell with a heterologous exo-endo cellulase fusion construct or vector as defined above in the first aspect and second aspect; b) cultivating the transformed fungal host cell under conditions suitable for said fungal host cell to produce an enzyme having cellulolytic activity; and c) recovering said enzyme.

In one embodiment of this aspect, the filamentous fungal host cell is a *Trichoderma* cell, and particularly a *T. reesei* host cell. In a second embodiment, the exo-cellobiohydrolase is a CBH1 and the endoglucanase is an *Acidothermus cellulolyticus* endoglucanase or a *Thermobifida fusca* endoglucanase. In a third embodiment, the recovered enzyme is a cellulase fusion protein, components of the cellulase fusion protein, or a combination of the cellulase fusion protein and the components thereof. In a fourth embodiment, the recovered enzyme(s) is purified.

In an seventh aspect, the invention includes a *Trichoderma* host cell which expresses a cellulase fusion protein, wherein said fusion protein comprises a catalytic domain of an exo-cellobiohydrolase and a catalytic domain of an endoglucanase, wherein the exo-cellobiohydrolase lacks a cellulose binding domain. In one embodiment, the *Trichoderma* host cell is a *T. reesei* cell. In a second embodiment, the exo-cellobiohydrolase is a CBH1 and the endoglucanase is an *Acidothermus cellulolyticus* endoglucanase and particularly an *Acidothermus cellulolyticus* E1 or GH74 endoglucanase. In a third embodiment, the endoglucanase lacks a cellulose binding domain. In a fourth embodiment, the *T. reesei* host cell includes deleted native cellulase genes.

In an eighth aspect, the invention includes a fungal cellulase composition comprising a cellulase fusion protein or components thereof, wherein the fusion protein or components thereof is the product of a recombinant *Trichoderma* spp. In one embodiment, the cellulase fusion protein is a CBH1-*Acidothermus cellulolyticus* E1 fusion protein and the components are the cleaved products, CBH1 and *Acidothermus cellulolyticus* E1, wherein each component has cellulolytic activity.

BRIEF DESCRIPTION OF THE FIGURES

FIG. 2 is a DNA sequence (SEQ ID NO: 1) of the *T. reesei* cbh1 signal sequence (SEQ ID NO: 2); the *T. reesei* cbh1 catalytic domain (SEQ ID NO: 3), and the *T. reesei* cbh1 linker (SEQ ID NO: 4). The signal sequence is underlined, the catalytic domain is in bold, and the linker sequence is in italics.

FIG. 3 shows the predicted amino acid sequence (SEQ ID NO: 5) based on the nucleotide sequence provided in FIG. 2, wherein the signal peptide is underlined, the catalytic domain, represented by (SEQ ID NO: 6), is in bold, and the linker is in italics.

FIG. 4 is an illustration of a nucleotide sequence (SEQ ID NO: 7) encoding an *Acidothermus cellulolyticus* GH5A endoglucanase I (E1) catalytic domain.

FIG. 5 is the predicted amino acid sequence (SEQ ID NO: 8) of the *Acidothermus cellulolyticus* GH5A E1 catalytic domain based on the nucleotide sequence provided in FIG. 4.

FIGS. 6A and 6B are an illustration of a nucleotide sequence (SEQ ID NO: 9) encoding an *Acidothermus cellulolyticus* GH74-EG catalytic domain.

FIG. 7 is the predicted amino acid sequence (SEQ ID NO: 10) of the *Acidothermus cellulolyticus* GH74-EG based on the nucleotide sequence provided in FIGS. 6A and 6B.

FIG. 8 is an illustration of a nucleotide sequence (SEQ ID NO: 11) encoding the CBD, linker and catalytic domain of endoglucanase 5 (E5) of *Thermobifida fusca*.

FIG. 9 is the predicted amino acid sequence (SEQ ID NO: 12) of the CBD, linker and E5 based on the nucleotide sequence provided in FIG. 8.

FIG. 10 is the nucleotide sequence (2656 bases) (SEQ ID NO: 13) of a heterologous cellulase fusion construct described in example 1 comprising, the *T. reesei* CBH1 signal sequence; the catalytic domain of the *T. reesei* CBH1; the *T. reesei* CBH1 linker sequence; a kexin cleavage site which includes codons for the amino acids SKR and the sequence coding for the *Acidothermus cellulolyticus* GH5A-E1 catalytic domain.

FIG. 11 is the predicted amino acid sequence (SEQ ID NO: 14) of the cellulase fusion protein based on the nucleic acid sequence in FIG. 10.

FIGS. 13A-E provide the nucleotide sequence (SEQ ID NO:15) (10239 bp) of the pTrex4 plasmid of FIG. 12 without the catalytic domain of the EG gene of interest.

DETAILED DESCRIPTION OF THE INVENTION

Figure 1:
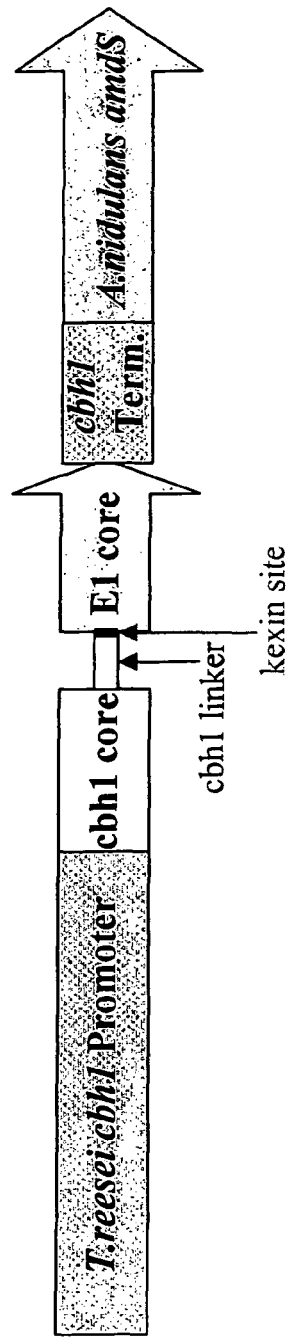
FIG. 1 is a representation of a heterologous exo-endo cellulase fusion construct encompassed by the invention, which includes a *Trichoderma reesei* cbh1 promoter, a cbh1 core (cbh1 signal sequence and cbh1 catalytic domain), a cbh1 linker sequence, a kexin site, an E1 core (an *Acidothermus cellulolyticus* E1 endoglucanase catalytic domain), a cbh1 terminator and an *A. nidulans* amdS selectable marker.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Practitioners are particularly directed to Sambrook et al., MOLECULAR CLONING: A LABORATORY MANUAL (Second and Third Editions (1989 and 2001), Cold Spring Harbor Press, Plainview, N.Y., and Ausubel F M et al., Current Protocols in Molecular Biology, John Wiley & Sons, New York, N.Y., 1993, for definitions and terms of the art.

It is to be understood that this invention is not limited to the particular methodology, protocols, and reagents described, as these may vary. Although any methods and materials similar or equivalent to those described herein can be used in the practice or testing of the present invention, the preferred methods and materials are described.

Numeric ranges are inclusive of the numbers defining the range. Unless otherwise indicated, nucleic acids are written left to right in 5' to 3' orientation; amino acid sequences are written left to right in amino to carboxy orientation, respectively.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

1. DEFINITIONS

The term "heterologous exo-endo cellulase fusion construct" refers to a nucleic acid construct that is composed of parts of different genes in operable linkage. The components include, from the 5' end, a DNA molecule encoding an exo-cellobiohydrolase catalytic domain and a DNA molecule encoding an endoglucanase catalytic domain.

The term "cellulase fusion protein" or "fusion protein having cellulolytic activity" refers to an enzyme, which has an exo-cellobiohydrolase catalytic domain and an endoglucanase catalytic domain and exhibits cellulolytic activity.

The term "components of a cellulase fusion protein" refers to individual (cleaved) fragments of the cellulase fusion protein, wherein each fragment has cellulolytic activity and includes one of the catalytic domains of the fusion protein.

The term "cellulase" refers to a category of enzymes capable of hydrolyzing cellulose (beta-1,4-glucan or beta D-glucosidic linkages) polymers to shorter cellooligosaccharide oligomers, cellobiose and/or glucose.

The term "exo-cellobiohydrolase" (CBH) refers to a group of cellulase enzymes classified as EC 3.2.1.91. These enzymes are also known as exoglucanases or cellobiohydrolases. CBH enzymes hydrolyze cellobiose from the reducing or non-reducing end of cellulose. In general, a CBH1 type enzyme preferentially hydrolyzes cellobiose from the reducing end of cellulose and a CBH2 type enzyme preferentially hydrolyzes the non-reducing end of cellulose.

The term "endoglucanase" (EG) refers to a group of cellulase enzymes classified as EC 3.2.1.4. An EG enzyme hydrolyzes internal beta-1,4 glucosidic bonds of the cellulose.

The term "beta-glucosidases" refers to a group of cellulase enzymes classified as EC 3.2.1.21.

"Cellulolytic activity" encompasses exoglucanase activity, endoglucanase activity or both types of enzymatic activity.

The term "catalytic domain" refers to a structural portion or region of the amino acid sequence of a cellulase which possess the catalytic activity of the cellulase. The catalytic domain is a structural element of the cellulase tertiary structure that is distinct from the cellulose binding domain or site, which is a structural element which binds the cellulase to a substrate, such as cellulose.

The term "cellulose binding domain (CBD)" as used herein refers to a portion of the amino acid sequence of a cellulase or a region of the enzyme that is involved in the cellulose binding activity of a cellulase. Cellulose binding domains generally function by non-covalently binding the cellulase to cellulose, a cellulose derivative or other polysaccharide equivalent thereof. CBDs typically function independent of the catalytic domain.

A nucleic acid is "operably linked" when it is placed into a functional relationship with another nucleic acid sequence. For example, DNA encoding a signal peptide is operably linked to DNA encoding a polypeptide if it is expressed as a preprotein that participates in the secretion of the polypeptide; a promoter is operably linked to a coding sequence if it affects the transcription of the sequence. Generally, "operably linked" means that the DNA sequences being linked are contiguous, and, in the case of the heterologous exo-endo cellulase fusion construct contiguous and in reading frame.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "nucleic acid molecule", "nucleic acid" or "polynucleotide" includes RNA, DNA and cDNA molecules. It will be understood that, as a result of the degeneracy of the genetic code, a multitude of nucleotide sequences encoding a given protein such as a cellulase fusion protein of the invention may be produced.

A "heterologous" nucleic acid sequence has a portion of the sequence, which is not native to the cell in which it is expressed. For example, heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid sequence may contain a control sequence/DNA coding sequence combination that is the same as, or different from a control sequence/DNA coding sequence combination found in the native cell. The term heterologous nucleic acid sequence encompasses a heterologous exo-endo cellulase fusion construct according to the invention.

As used herein, the term "vector" refers to a nucleic acid sequence or construct designed for transfer between different host cells. An "expression vector" refers to a vector that has the ability to incorporate and express heterologous DNA sequences in a foreign cell. An expression vector may be generated recombinantly or synthetically, with a series of specified nucleic acid elements that permit transcription of a particular nucleic acid in a target cell. The recombinant expression cassette can be incorporated into a plasmid, chromosome, mitochondrial DNA, virus, or nucleic acid fragment.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The term "signal sequence" or "signal peptide" refers to a sequence of amino acids at the N-terminal portion of a protein, which facilitates the secretion of the mature form of the protein outside the cell. The mature form of the extracellular protein lacks the signal sequence which is cleaved off during the secretion process.

By the term "host cell" is meant a cell that contains a heterologous exo-endo cellulase fusion construct encompassed by the invention or a vector including the same and supports the replication, and/or transcription or transcription and translation (expression) of the heterologous exo-endo cellulase construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" includes all filamentous fungi recognized by those of skill in the art. A preferred fungus is selected from the subdivision Eumycota and Oomycota and particularly from the group consisting of *Aspergillus, Trichoderma, Fusarium, Chrysosporium, Penicillium, Humicola, Neurospora*, or alternative sexual forms thereof such as *Emericella* and *Hypocrea* (See, Kuhls et al., 1996).

The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

The term "derived" encompasses the terms originated from, obtained or obtainable from and isolated from.

An "equivalent" amino acid sequence is an amino acid sequence that is not identical to an original reference amino acid sequence but includes some amino acid changes, which may be substitutions, deletions, additions or the like, wherein the protein exhibits essentially the same qualitative biological activity of the reference protein. An equivalent amino acid sequence will have between 80%-99% amino acid identity to the original reference sequence. Preferably the equivalent amino acid sequence will have at least 85%, 90%, 93%, 95%, 96%, 98% and 99% identity to the reference sequence.

A "substitution" results from the replacement of one or more nucleotides or amino acid by different nucleotides or amino acids, respectively. Substitutions are usually made in accordance with known conservative substitutions, wherein one class of amino acid is substituted with an amino acid in the same class. A "non-conservative substitution" refers to the substitution of an amino acid in one class with an amino acid from another class.

A "deletion" is a change in a nucleotide or amino acid sequence in which one or more nucleotides or amino acids are absent.

An "addition" is a change in a nucleotide or amino acid sequence that has resulted from the insertion of one or more nucleotides or amino acid as compared to an original reference sequence.

As used herein, "recombinant" includes reference to a cell or vector, that has been modified by the introduction of heterologous nucleic acid sequences or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a heterologous nucleic acid sequence according to the invention integrated into its genome or as an episomal plasmid that is maintained through multiple generations.

The term "introduced" in the context of inserting a heterologous exo-endo cellulase fusion construct or heterologous nucleic acid sequence into a cell, means "transfection", "transformation" or "transduction" and includes reference to the incorporation of a heterologous nucleic acid sequence or heterologous exo-endo cellulase fusion construct into a eukaryotic or prokaryotic cell where the heterologous nucleic acid sequence or heterologous exo-endo cellulase nucleic acid construct may be incorporated into the genome of the cell (for example, chromosome, plasmid, plastid, or mitochondrial DNA), converted into an autonomous replicon, or transiently expressed (for example, transfected mRNA).

As used herein, the term "expression" refers to the process by which a polypeptide is produced based on the nucleic acid sequence of a gene. The process includes both transcription and translation.

It follows that the term "cellulase fusion protein expression" or "fusion expression" refers to transcription and translation of a "heterologous exo-endo cellulase fusion construct" comprising the catalytic domain of an exo-cellobiohydrolase and the catalytic domain of an endoglucanase, the products of which include precursor RNA, mRNA, polypeptide, post-translationally processed polypeptides, and derivatives thereof.

As used herein, the term "purifying" generally refers to subjecting recombinant nucleic acid or protein containing cells to biochemical purification and/or column chromatography.

As used herein, the terms "active" and "biologically active" refer to a biological activity associated with a particular protein, such as the enzymatic activity associated with a cellulase. It follows that the biological activity of a given protein refers to any biological activity typically attributed to that protein by those of skill in the art.

As used herein, the term "enriched" means that the concentration of a cellulase enzyme found in a fungal cellulase composition is greater relative to the concentration found in a wild type or naturally occurring fungal cellulase composition. The terms enriched, elevated and enhanced may be used interchangeably herein.

A "wild type fungal cellulase composition" is one produced by a naturally occurring fungal source and which comprises one or more BG, CBH and EG components wherein each of these components is found at the ratio produced by the fungal source.

Thus, to illustrate, a naturally occurring cellulase system may be purified into substantially pure components by recognized separation techniques well published in the literature, including ion exchange chromatography at a suitable pH, affinity chromatography, size exclusion and the like. A purified cellulase fusion protein or components thereof may then be added to the enzymatic solution resulting in an enriched cellulase solution. It is also possible to elevate the amount of EG or CBH produced by a microbe by expressing a cellulase fusion protein encompassed by the invention.

"A", "an" and "the" include plural references unless the context clearly dictates otherwise.

As used herein the term "comprising" and its cognates are used in their inclusive sense: that is equivalent to the term "including" and its corresponding cognates.

"ATCC" refers to American Type Culture Collection located in Manassas Va. 20108 (ATCC www/atcc.org).

"NRRL" refers to the Agricultural Research Service Culture Collection, National Center for Agricultural utilization Research (and previously known as USDA Northern Regional Research Laboratory), Peoria, Ill.

2. PREFERRED EMBODIMENTS

A. Components and Construction of Heterologous Exo-Endo Cellulase Fusion Constructs and Expression Vectors A heterologous exo-endo cellulase fusion construct or a vector comprising a heterologous exo-endo cellulase fusion construct may be introduced into and replicated in a filamentous fungal host cell for protein expression and secretion.

In some embodiments, the heterologous exo-endo cellulase fusion construct comprises in operable linkage from the 5' end of said construct, optionally a signal peptide, a DNA molecule encoding a catalytic domain of an exo-cellobiohydrolase, and a DNA molecule encoding a catalytic domain of an endoglucanase. In other embodiments, the components of the heterologous exo-endo cellulase fusion construct comprise in operable linkage from the 5' end of said construct, optionally a signal peptide, a DNA molecule encoding a catalytic domain of an exo-cellobiohydrolase, optionally a DNA molecule encoding the CBD of an endoglucanase, and a DNA molecule encoding a catalytic domain of the endoglucanase.

In other embodiments the construct will comprise in operable linkage from the 5' end of said construct optionally a signal peptide, a DNA molecule encoding a catalytic domain of an exo-cellobiohydrolase, optionally a DNA molecule encoding the CBD of the exo-cellobiohydrolase, a linker, optionally a DNA molecule encoding the CBD of an endoglucanase, and a DNA molecule encoding a catalytic domain of the endoglucanase.

In a further embodiment the heterologous exo-endo cellulase fusion construct or vector comprising a heterologous exo-endo cellulase fusion construct includes in operable linkage from the 5' end, a promoter of a filamentous fungus secretable protein; a DNA molecule encoding a signal sequence; a DNA molecule encoding a catalytic domain of an exo-cellobiohydrolase, optionally a DNA molecule encoding the exo-cellobiohydrolase CBD; a DNA molecule encoding a catalytic domain of an endoglucanase; and a terminator. Further the vector may include a DNA molecule encoding the CBD of the endoglucanase said CBD located 5' to the DNA molecule encoding the endoglucanase catalytic domain.

Figure 12:
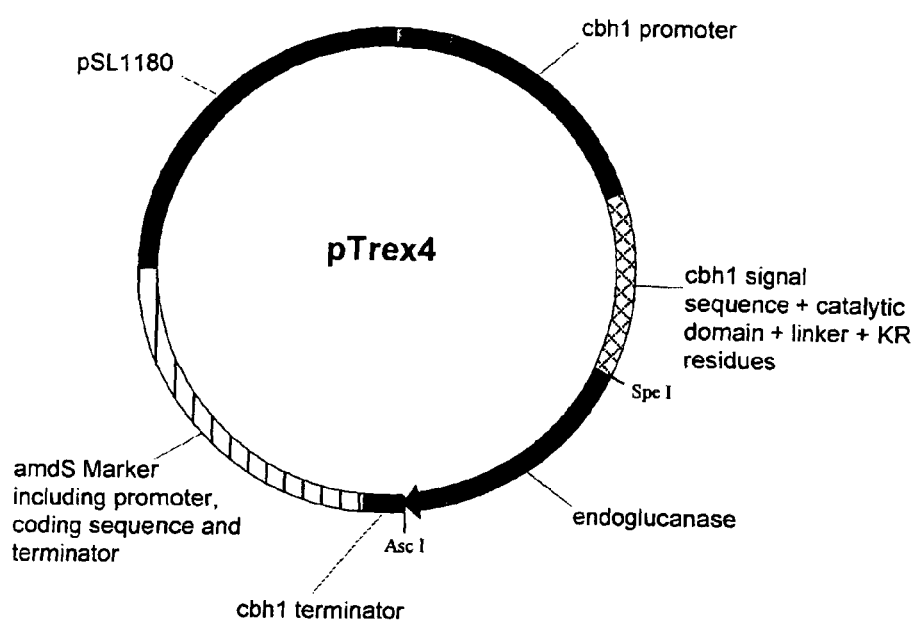
FIG. 12 provides a schematic diagram of the pTrex4 plasmid, which was used for expression of a heterologous exo-endo cellulase fusion construct (CBH1-endoglucanase) as described in the examples and includes the *Trichoderma reesei* cbh1 promoter, the *T. reesei* CBH1 signal sequence, catalytic domain, and linker sequences, a kexin cleavage site and an endoglucanase gene of interest inserted between a SpeI and AscI site, a CBH1 *Trichoderma reesei* terminator and the amdS *Aspergillus nidulans* acetamidase marker gene.

In one embodiment a preferred heterologous exo-endo cellulase fusion construct or expression vector will not include the exo-cellobiohydrolase CBD. In another embodiment, a preferred expression vector will include a promoter of a filamentous fungus secretable protein, a DNA molecule encoding an exo-cellobiohydrolase signal sequence, a DNA molecule encoding a catalytic domain of an exo-cellobiohydrolase, a linker, a DNA molecule encoding a catalytic domain of an endoglucanase, and a terminator, wherein the vector lacks the CBD of the exo-cellobiohydrolase and optionally lacks the CBD of the endoglucanase. In a preferred embodiment, the coding sequence for the endoglucanase catalytic domain (either including the endoglucanase CBD or lacking the endoglucanase CBD) will not include an endoglucanase signal sequence. Reference is made to FIGS. 1, 10 and 12 as examples of embodiments including an expression vector and heterologous exo-endo cellulase fusion construct of the invention.

Exemplary promoters include both constitutive promoters and inducible promoters. Examples include the promoters from the *Aspergillus niger*, *A. awamori* or *A. oryzae* glucoamylase, alpha-amylase, or alpha-glucosidase encoding genes; the *A. nidulans* gpdA or trpC genes; the *Neurospora crassa* cbh1 or trp1 genes; the *A. niger* or *Rhizomucor miehei* aspartic proteinase encoding genes; the *T. reesei* cbh1, cbh2, egl1, egl2, or other cellulase encoding genes; a CMV promoter, an SV40 early promoter, an RSV promoter, an EF-1α promoter, a promoter containing the tet responsive element (TRE) in the tet-on or tet-off system as described (ClonTech and BASF), the beta actin promoter. In some embodiments the promoter is one that is native to the fungal host cell to be transformed.

In one preferred embodiment, the promoter is an exo-cellobiohydrolase cbh1 or cbh2 promoter and particularly a cbh1 promoter, such as a *T. reesei* cbh1 promoter. The *T. reesei* cbh1 promoter is an inducible promoter, and reference is made to GenBank Accession No. D86235.

The DNA sequence encoding an exo-cellobiohydrolase catalytic domain is operably linked to a DNA sequence encoding a signal sequence. The signal sequence is preferably that which is naturally associated with the exo-cellobiohydrolase to be expressed. Preferably the signal sequence is encoded by a *Trichoderma* or *Aspergillus* gene which encodes a CBH. More preferably the signal sequence is encoded by a *Trichoderma* gene which encodes a CBH1. In further embodiments, the promoter and signal sequence of the heterologous exo-endo cellulase fusion construct are derived from the same source. In some embodiments, the signal sequence is a *Trichoderma* cbh1 signal sequence that is operably linked to a *Trichoderma* cbh1 promoter. In further embodiments the signal sequence has the amino acid sequence of SEQ ID NO: 2 or an equivalent sequence or a sequence having at least 95% identity thereto.

Most exo-cellobiohydrolases (CBHs) and endoglucanases (EGs) have a multidomain structure consisting of a catalytic domain separated from a cellulose binding domain (CBD) by a linker peptide (Suurnakki et al., 2000). The catalytic domain contains the active site whereas the CBD interacts with cellulose by binding the enzyme to it (van Tilbeurgh et al., 1986 and Tomme et al., 1988).

Numerous cellulases have been described in the scientific literature, examples of which include: from *Trichoderma reesei*: Shoemaker, S. et al., Bio/Technology, 1:691-696, 1983, which discloses CBH1; Teeri, T. et al., Gene, 51:43-52, 1987, which discloses CBH2; Penttila, M. et al., Gene, 45:253-263,1986, which discloses EG1; Saloheimo, M. et al., Gene, 63:11-22,1988, which discloses EG2; Okada, M. et al., Appl. Environ. Microbiol., 64:555-563,1988, which discloses EG3; Saloheimo, M. et al., Eur. J. Biochem., 249:584-591, 1997, which discloses EG4; and Saloheimo, A. et al., Molecular Microbiology, 13:219-228, 1994, which discloses EG5. Exo-cellobiohydrolases and endoglucanases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; and Saarilahti et al., 1990 which discloses an endoglucanase from *Erwinia carotovara*. The sequences encoding these enzymes may be used in the heterologous exo-endo cellulase fusion construct or vector of the invention.

In some embodiments, the catalytic domain is derived from a CBH1 type exo-cellobiohydrolase and in other embodiments the catalytic domain is derived from a CBH2 type exo-cellobiohydrolase. In some embodiments, the CBH1 or CBH2 catalytic domain is derived from a *Trichoderma* spp.

In one embodiment, the catalytic domain of an exo-cellobiohydrolase is encoded by a nucleic acid sequence of a *Trichoderma reesei* cbh1. In some embodiments the nucleic acid is the sequence of SEQ ID NO:3 and nucleotide sequences homologous thereto.

In other embodiments, the catalytic domain will have the amino acid sequence of SEQ ID NO: 6 and equivalent amino acid sequences thereto. Further DNA sequences encoding any equivalents of said amino acid sequences of SEQ ID NO: 6, wherein said equivalents have a similar qualitative biological activity to SEQ ID NO: 6 may be incorporated into the heterologous exo-endo cellulase fusion construct.

In some embodiments, heterologous exo-endo cellulase fusion constructs encompassed by the invention will include a linker located 3' to the sequence encoding the exo-cellobiohydrolase catalytic domain and 5' to the sequence encoding the endoglucanase catalytic domain. In some preferred embodiments, the linker is derived from the same source as the catalytic domain of the exo-cellobiohydrolase. Preferably the linker will be derived from a *Trichoderma* cbh1 gene. One preferred linker sequence is illustrated in FIG. 3. In other embodiments, the heterologous exo-endo cellulase fusion construct will include two or more linkers. For example a linker may be located not only between the coding sequence of the CBH catalytic domain and the coding sequence of the EG catalytic domain but also between the coding region of the CBH CBD and the coding region of the EG CBD. Further linkers may be located between the CBD of the endoglucanase and the catalytic domain of the endoglucanase. In general, a linker may be between about 5 to 60 amino acid residues, between about 15 to 50 amino acid residues, and between about 25 to 45 amino acid residues. Reference is made to Srisodsuk M. et al., 1993 for a discussion of the linker peptide of *T. reesei* CBH1.

In addition to the linker sequence, a heterologous exo-endo cellulase fusion construct or expression vector of the invention may include a cleavage site, such as a protease cleavage site. In one preferred embodiment, the cleavage site is a kexin site which encodes the dipeptide Lys-Arg.

In a preferred embodiment, the heterologous exo-endo cellulase fusion construct and an expression vector including the same will lack the CBD of the CBH. In other embodiments the CBD will be included in the construct or vector.

The heterologous exo-endo cellulase fusion constructs include a coding sequence for the catalytic domain of an endoglucanase. Endoglucanases are found in more than 13 of the Glycosyl Hydrolase families using the classification of Coutinho, P. M. et al. (1999) Carbohydrate-Active Enzymes (CAZy) server at (afmb.cnrs-mrs.fr/~cazy/CAZY/index). Preferably the catalytic domain is derived from a bacterial endoglucanase. As described above numerous bacterial endoglucanases are known.

Particularly preferred DNA sequences encoding a catalytic domain of a bacterial endoglucanase include:

a) the DNA of SEQ ID NO: 7 encoding an *Acidothermus cellulolyticus* GH5A endoglucanase I (E1) catalytic domain having amino acid sequence SEQ ID NO: 8;

b) the DNA of SEQ ID NO: 9 encoding an *Acidothermus cellulolyticus* GH74 endoglucanase catalytic domain having amino acid sequence SEQ ID NO: 10;

c) the DNA of SEQ ID NO: 11 encoding a *Thermobifida fusca* E5 endoglucanase having amino acid sequence SEQ ID NO: 12 and d) DNA sequences or homologous DNA sequences encoding any equivalents of said amino acid sequences of SEQ ID NOs: 8, 10 and 12 wherein said equivalents have a similar qualitative biological activity to said sequences.

In some preferred embodiments, the endoglucanase is an *Acidothermus cellulolyticus* E1 and reference is made to the an *Acidothermus cellulolyticus* endoglucanases disclosed in WO 9105039; WO 9315186; U.S. Pat. No. 5,275,944; WO 9602551; U.S. Pat. No. 5,536,655 and WO 0070031. Also reference is made to GenBank U33212. In some embodiments, the *Acidothermus cellulolyticus* E1 has an amino acid sequence of a least 90%, 93%, 95% and 98% sequence identity with the sequence set forth in SEQ ID NO: 6.

As stated above homologous nucleic acid sequences to the nucleic acid sequences illustrated in SEQ ID NOs: 1, 3, 7, 9 and 11 may be used in a heterologous cellulase fusion construct or vector according to the invention. Homologous sequences include sequences found in other species, naturally occurring allelic variants and biologically active functional derivatives. A homologous sequence will have at least 80%, 85%, 88%, 90%, 93%, 95%, 97%, 98% and 99% identity to one of the sequences of SEQ ID NOs: 1, 3, 7, 9 and 11 when aligned using a sequence alignment program. For example, a homologue of a given sequence has greater than 80% sequence identity over a length of the given sequence e.g., the coding sequence for the Tf-E5 catalytic domain as described herein.

For a given heterologous exo-endo cellulase fusion construct or components of the construct it is appreciated that as a result of the degeneracy of the genetic code, a number of coding sequences can be produced that encode a protein having the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the nucleic acid sequences covered by the present invention. Any and all of these sequences can be utilized in the same way as described herein for a CBH catalytic domain or a bacterial EG catalytic domain.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST/. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In one exemplary approach, sequence extension of a nucleic acid encoding a CBH or EG catalytic domain may be carried out using conventional primer extension procedures as described in Sambrook et al., supra, to detect CBH or bacterial EG precursors and processing intermediates of mRNA that may not have been reverse-transcribed into cDNA and/or to identify ORFs that encode the catalytic domain or full length protein.

In yet another aspect, the entire or partial nucleotide sequence of the nucleic acid sequence of the *T. reesei* chb1 or GH5a-E1 may be used as a probe. Such a probe may be used to identify and clone out homologous nucleic acid sequences from related organisms.

Screening of a cDNA or genomic library with the selected probe may be conducted using standard procedures, such as described in Sambrook et al., (1989). Hybridization conditions, including moderate stringency and high stringency, are provided in Sambrook et al., supra.

In addition, alignment of amino acid sequences to determine homology or identity between sequences is also preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada.

An example of an algorithm that is suitable for determining sequence similarity is the BLAST algorithm, which is described in Altschul, et al., *J. Mol. Biol.* 215:403-410 (1990) and reference is also made to Henikoff & Henikoff, *Proc. Natl. Acad. Sci. USA* 89:10915 (1989)). Software for performing BLAST analyses is publicly available through the National Center for Biotechnology Information (<www.ncbi.nlm.nih.gov>).

The heterologous exo-endo cellulase fusion construct according to the invention may also include a terminator sequence. In some embodiments the terminator and the promoter are derived from the same source, for example a *Trichoderma* exo-cellobiohydrolase gene. In other embodiments the terminator and promoter are derived from different sources. In preferred embodiments the terminator is derived from a filamentous fungal source and particular a *Trichoderma*. Particularly suitable terminators include cbh1 derived from a strain of *Trichoderma* specifically *T. reesei* and the glucoamylase terminator derived from *Aspergillus niger* or *A. awamori* (Nunberg et al., 1984 and Boel et al., 1984).

The heterologous exo-endo cellulase fusion construct or a vector comprising a fusion construct may also include a selectable marker. The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Markers useful in vector systems for transformation of *Trichoderma* are described in Finkelstein, Chap. 6, in BIOTECHNOLOGY OF FILAMENTOUS FUNGI, Finkelstein et al eds. Butterworth-Heinemann, Boston, Mass. 1992. The amdS gene from *Aspergillus nidulans* encodes the enzyme acetamidase that allows transformant cells to grow on acetamide as a nitrogen source (Kelley et al., EMBO J. 4:475-479 (1985) and Penttila et al., Gene 61:155-164 (1987)). The selectable marker (e.g. pyrG) may restore the ability of an auxotrophic mutant strain to grow on a selective minimal medium and the selectable marker (e.g. olic31) may confer to transformants the ability to grow in the presence of an inhibitory drug or antibiotic A typical heterologous exo-endo cellulase fusion construct is depicted in FIGS. 1 and 10. Methods used to ligate a heterologous exo-endo cellulase fusion construct encompassed by the invention and other heterologous nucleic acid sequences and to insert them into suitable vectors are well known in the art. Linking is generally accomplished by ligation at convenient restriction sites, and if such sites do not exist, synthetic oligonucleotide linkers are used in accordance with conventional practice. Additionally vectors can be constructed using known recombination techniques.

Any vector may be used as long as it is replicable and viable in the cells into which it is introduced. Large numbers of suitable cloning and expression vectors are described in Sambrook et al., 1989, Ausubel F M et al., 1993, and Strathern et al., 1981, each of which is expressly incorporated by reference herein. Further appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a vector by a variety of procedures. In general, the DNA sequence is inserted into an appropriate restriction endonuclease site(s) by standard procedures. Such procedures and related sub-cloning procedures are deemed to be within the scope of knowledge of those skilled in the art. Exemplary useful plasmids include pUC18, pBR322, pUC100, pSL1180 (Pharmacia Inc., Piscataway, N.J.) and pFB6. Other general purpose vectors such as in *Aspergillus*, pRAX and in *Trichoderma*, pTEX maybe also be used (FIGS. 12 and 13).

In one embodiment, a preferred vector is the vector disclosed in FIGS. 12 and 13, wherein the vector includes the nucleic acid sequence encoding the CBD, linker and catalytic domain of the *Thermobifida fusca* endoglucanase 5 (SEQ ID NO: 12). In another embodiment, a preferred vector is the vector disclosed in FIGS. 12 and 13, wherein the vector includes the nucleotide sequence encoding an *Acidothermus cellulolyticus* GH5A endoglucanase catalytic domain (SEQ ID NO: 8).

B. Target Host Cells

In one embodiment of the present invention, the filamentous fungal parent or host cell may be a cell of a species of, but not limited to, *Trichoderma* sp., *Penicillium* sp., *Humicola* sp., *Chrysosporium* sp., *Gliocladium* sp., *Aspergillus* sp., *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*. Some preferred species for *Trichoderma* fungal parent cells include *Trichoderma longibrachiatum* (*reesei*), *Trichoderma viride*, *Trichoderma koningii*, and *Trichoderma harzianum* cells. Particularly preferred host cells include cells from strains of *T. reesei*, such as RL-P37 (Sheir-Neiss, et al., *Appl. Microbiol. Biotechnol.* 20:46-53 (1984) and functionally equivalent and derivative strains, such as *Trichoderma reesei* strain RUT-C30 (ATCC No. 56765) and strain QM9414 (ATCC No. 26921). Also reference is made to ATCC No. 13631, ATCC No. 26921, ATCC No. 56764, ATCC No. 56767 and NRRL 1509.

Some preferred species for *Aspergillus* fungal parent cells include *Aspergillus niger*, *Aspergillus awamori*, *Aspergillus aculeatus*, and *Aspergillus nidulans* cells. In one embodiment, the strain comprises *Aspergillus niger*, for example *A. niger* var. *awamori* dgr246 (Goedegebuur et al, (2002) *Curr. Genet* 41: 89-98) and GCDAP3, GCDAP4 and GAP3-4 (Ward, M, et al., (1993), *Appl. Microbiol. Biotechnol.* 39:738-743).

In some instances it is desired to obtain a filamentous host cell strain such as a *Trichoderma* host cell strain which has had one or more cellulase genes deleted prior to introduction of a heterologous exo-endo cellulase fusion construct encompassed by the invention. Such strains may be prepared by the method disclosed in U.S. Pat. No. 5,246,853, U.S. Pat. No. 5,861,271 and WO 92/06209, which disclosures are hereby incorporated by reference. By expressing a cellulase fusion protein or components thereof having cellulolytic activity in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EG3 and/or EG5 protein (see e.g., U.S. Pat. No. 5,475,101 and WO 94/28117, respectively). Gene deletion may be accomplished by inserting a form of the desired gene to be deleted or disrupted into a plasmid by methods known in the art.

Parental fungal cell lines are generally cultured under standard conditions with media containing physiological salts and nutrients, such as described by Pourquie, J. et al., BIOCHEMISTRY AND GENETICS OF CELLULOSE DEGRADATION, eds. Aubert J. P. et al., Academic Press pp. 71-86 (1988) and Ilmen, M. et al., *Appl. Environ. Microbiol.* 63:1298-1306 (1997). Also reference is made to common commercially prepared media such as yeast Malt Extract (YM) broth, Luria Bertani (LB) broth and Sabouraud Dextrose (SD) broth.

C. Introduction of a Heterologous Exo-Endo Cellulase Fusion Construct or Vector into Fungal Host Cells and Culture Conditions A host fungal cell may be genetically modified (i.e., transduced, transformed or transfected) with a heterologous exo-endo cellulase fusion construct according to the invention, a cloning vector or an expression vector comprising a heterologous exo-endo cellulase fusion construct. The methods of transformation of the present invention may result in the stable integration of all or part of the construct or vector into the genome of the filamentous fungus. However, transformation resulting in the maintenance of a self-replicating extra-chromosomal transformation vector is also contemplated.

Many standard transformation methods can be used to produce a filamentous fungal cell line such as a *Trichoderma* or *Aspergillus* cell line that express large quantities of a heterologous protein. Some of the published methods for the introduction of DNA constructs into cellulase-producing strains of *Trichoderma* include Lorito, Hayes, DiPietro and Harman (1993) *Curr. Genet.* 24: 349-356; Goldman, Van-Montagu and Herrera-Estrella (1990) *Curr. Genet.* 17:169-174; Penttila, Nevalainen, Ratto, Salminen and Knowles (1987) *Gene* 61: 155-164, EP-A-0 244 234 and also Hazell B. et al., 2000; for *Aspergillus* include Yelton, Hamer and Timberlake (1984) *Proc. Natl. Acad. Sci.* USA 81: 1470-1474; for *Fusarium* include Bajar, Podila and Kolattukudy, (1991) *Proc. Natl. Acad. Sci.* USA 88: 8202-8212; for *Streptomyces* include Hopwood et al., (1985) Genetic Manipulation of *Streptomyces*: A Laboratory Manual, The John Innes Foundation, Norwich, UK; and for *Bacillus* include Brigidi, DeRossi, Bertarini, Riccardi and Matteuzzi, (1990), FEMS Microbiol. Lett. 55:135-138.

Other methods for introducing a heterologous exo-endo cellulase fusion construct or vector into filamentous fungi (e.g., *H. jecorina*) include, but are not limited to the use of a particle or gene gun (biolistics), permeabilization of filamentous fungi cells walls prior to the transformation process (e.g., by use of high concentrations of alkali, e.g., 0.05 M to 0.4 M $CaCl_2$ or lithium acetate), protoplast fusion, electroporation, or agrobacterium mediated transformation (U.S. Pat. No. 6,255,115).

An exemplary method for transformation of filamentous fungi by treatment of protoplasts or spheroplasts with polyethylene glycol and $CaCl_2$ is described in Campbell, et al., (1989) *Curr. Genet* 16:53-56, 1989 and Penttila, M. et al., (1988) *Gene,* 63:11-22 and Penttila, M. et al., (1987) *Gene* 61:155-164.

Any of the well-known procedures for introducing foreign nucleotide sequences into host cells may be used. It is only necessary that the particular genetic engineering procedure used be capable of successfully introducing at least one gene into the host cell capable of expressing the heterologous gene.

The invention includes the transformants of filamentous fungi especially *Trichoderma* cells comprising the coding sequences for the cellulase fusion protein. The invention further includes the filamentous fungi transformants for use in producing fungal cellulase compositions, which include the cellulase fusion protein or components thereof.

Following introduction of a heterologous exo-endo cellulase fusion construct comprising the exoglucanase catalytic domain coding sequence and the endoglucanase catalytic domain coding sequence, the genetically modified cells can be cultured in conventional nutrient media as described above for growth of target host cells and modified as appropriate for activating promoters and selecting transformants. The culture conditions, such as temperature, pH and the like, are those previously used for the host cell selected for expression, and will be apparent to those skilled in the art. Also preferred culture conditions for a given filamentous fungus may be found in the scientific literature and/or from the source of the fungi such as the American Type Culture Collection (ATCC; www.atcc.org/).

Stable transformants of filamentous fungi can generally be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

The progeny of cells into which such heterologous exo-endo cellulase fusion constructs, or vectors including the same, have been introduced are generally considered to comprise the fusion protein encoded by the nucleic acid sequence found in the heterologous cellulase fusion construct.

In one exemplary application of the invention encompassed herein a recombinant strain of filamentous fungi, e.g., *Trichoderma reesei*, comprising a heterologous exo-endo cellulase fusion construct will produce not only a cellulase fusion protein but also will produce components of the cellulase fusion protein. In some embodiments the recombinant cells including the cellulase fusion construct will produce an increased amount of cellulolytic activity compared to a corresponding recombinant filamentous fungi strain grown under essentially the same conditions but genetically modified to include separate heterologous nucleic acid constructs encoding an exo-cellobiohydrolase catalytic domain and/or an endoglucanase catalytic domain.

D. Analysis of Protein Expression

In order to evaluate the expression of a cellulase fusion protein of the invention by a cell line that has been transformed with a heterologous exo-endo cellulase fusion construct, assays can be carried out at the protein level, the RNA level or by use of functional bioassays particular to exo-cellobiohydrolase activity or endoglucanase activity and/or production.

In general, the following assays can be used to determine integration of cellulase fusion protein expression constructs and vector sequences, Northern blotting, dot blotting (DNA or RNA analysis), RT-PCR (reverse transcriptase polymerase chain reaction), in situ hybridization, using an appropriately labeled probe (based on the nucleic acid coding sequence), conventional Southern blotting and autoradiography.

In addition, the production and/or expression of a cellulase enzyme may be measured in a sample directly, for example, by assays for cellobiohydrolase or endoglucanase activity, expression and/or production. Such assays are described, for example, in Becker et al., Biochem J. (2001) 356:19-30; Mitsuishi et al., FEBS (1990) 275:135-138. Shoemaker et al. 1978; and Schulein 1988) each of which is expressly incorporated by reference herein. The ability of CBH1 to hydrolyze isolated soluble and insoluble substrates can be measured using assays described in Srisodsuk et al., J. Biotech. (1997) 57:49-57 and Nidetzky and Claeyssens Biotech. Bioeng. (1994) 44:961-966. Substrates useful for assaying exo-cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a cellulase, for example CBH. The details of such methods are known to those of skill in the art and many reagents for practicing such methods are commercially available.

In an embodiment of the invention, the cellulase fusion protein which is expressed by the recombinant host cell will be about 0.1 to 80% of the total expressed cellulase. In other embodiments, the amount of expressed fusion protein will be in the range of about 0.1 mg to 100 g; about 0.1 mg to 50 g and 0.1 mg to 10 g protein per liter of culture media.

E. Recovery and Purification of Cellulase Fusion Proteins and Components Thereof In general, a cellulase fusion protein or components of the cellulase fusion protein produced in cell culture are secreted into the medium and may be recovered and optionally purified, e.g., by removing unwanted components from the cell culture medium. However, in some cases, a cellulase fusion protein or components thereof may be produced in a cellular form necessitating recovery from a cell lysate. In such cases the protein is purified from the cells in which it was produced using techniques routinely employed by those of skill in the art. Examples include, but are not limited to, affinity chromatography (van Tilbeurgh et al., FEBS Lett. 16:215,1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165,1998), hydrophobic interaction chromatography (Tomaz and Queiroz, J. Chromatography A 865:123-128, 1999), and two-phase partitioning (Brumbauer, et al., Bioseparation 7:287-295, 1999).

Once expression of a given cellulase fusion protein is achieved, the proteins thereby produced may be purified from the cells or cell culture by methods known in the art and reference is made to Deutscher, Methods in Enzymology, vol. 182, no. 57, pp. 779,1990; and Scopes, Methods Enzymol. 90: 479-91,1982. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75.

A purified form of a cellulase fusion protein or components thereof may be used to produce either monoclonal or polyclonal antibodies specific to the expressed protein for use in various immunoassays. (See, e.g., Hu et al., Mol Cell Biol. vol. 11, no. 11, pp. 5792-5799, 1991). Exemplary assays include ELISA, competitive immunoassays, radioimmunoassays, Western blot, indirect immunofluorescent assays and the like.

F. Utility of Enzymatic Compositions Comprising the Cellulase Fusion Proteins or Components Thereof.

The cellulase fusion protein and components comprising the catalytic domains of the cellulase fusion protein find utility in a wide variety applications, including use in detergent compositions, stonewashing compositions, in compositions for degrading wood pulp into sugars (e.g., for bioethanol production), and/or in feed compositions. In some embodiments, the cellulase fusion protein or components thereof may be used as cell free extracts. In other embodiments, the fungal cells expressing a heterologous exo-endo cellulase fusion construct are grown under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the production of products and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate an all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

In some applications, the cellulase fusion protein and components thereof find utility in detergent compositions, stonewashing compositions or in the treatment of fabrics to improve their feel and appearance. A detergent composition refers to a mixture which is intended for use in a wash medium for the laundering of soiled cellulose containing fabrics. A stonewashing composition refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

In the context of the present invention, such compositions may also include, in addition to cellulases, surfactants, additional hydrolytic enzymes, builders, bleaching agents, bleach activators, bluing agents and fluorescent dyes, caking inhibitors, masking agents, cellulase activators, antioxidants, and solubilizers.

Surfactants may comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

Cellulose containing fabric may be any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Cotton-containing fabrics are sewn or unsewn fabrics, yarns or fibers made of pure cotton or cotton blends including cotton woven fabrics, cotton knits, cotton denims, cotton yarns, raw cotton and the like.

Preferably the cellulase compositions comprising the cellulase fusion protein or components thereof are employed from about 0.00005 weight percent to about 5 weight percent relative to the total detergent composition. More preferably, the cellulase compositions are employed from about 0.0002 weight percent to about 2 weight percent relative to the total detergent composition.

Since the rate of hydrolysis of cellulosic products may be increased by using a transformant having a heterologous cellulase fusion construct inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol. A composition containing an enhanced amount of cellulolytic activity due to the inclusion of a cellulase fusion protein or components thereof may find utility in ethanol production Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized endoglucanase activity from a cellulase fusion protein or components thereof may greatly enhance the production of ethanol and sugar which can be converted by fermentation to other chemicals.

Thus, the inventive cellulase fusion protein and components thereof find use in the hydrolysis of cellulose to its sugar components. In one embodiment, the cellulase fusion protein or components thereof are added to the biomass prior to the addition of a fermentative organism. In another embodiment, the cellulase fusion protein or components thereof are added to the biomass at the same time as a fermentative organism. Optionally, there may be other cellulase components present in either embodiment.

EXPERIMENTAL

The present invention is described in further detail in the following examples which are not in any way intended to limit the scope of the invention.

In the disclosure and experimental section, which follows, the following abbreviations apply:

CBH1-E1 (*T. reesei* CBH1 catalytic domain and linker fused to an *Acidothermus cellulolyticus* GH5A endoglucanase I catalytic domain);

CBH1-74E (*T. reesei* CBH1 catalytic domain and linker fused to an *Acidothermus cellulolyticus* GH74 endoglucanase catalytic domain);

CBH1-TfE5 (*T. reesei* CBH1 catalytic domain and linker fused to a *Thermobifida fusca* E5 endoglucanase cellulose binding domain, linker and *Thermobifida fusca* E5 endoglucanase catalytic domain;

wt % (weight percent); ° C. (degrees Centigrade); rpm (revolutions per minute); $H_2O$ (water); $dH_2O$ (deionized water); aa (amino acid); bp (base pair); kb (kilobase pair); kD (kilodaltons); g (grams); μg (micrograms); mg (milligrams); μL (microliters); ml and mL (milliliters); mm (millimeters); μm (micrometer); M (molar); mM (millimolar); μM (micromolar); U (units); MW (molecular weight); sec (seconds); min(s) (minute/minutes); hr(s) (hour/hours); PAGE (polyacrylamide gel electrophoresis); phthalate buffer, (sodium phthalate in water, 20 mN, pH 5.0); PBS (phosphate buffered saline [150 mM NaCl, 10 mM sodium phosphate buffer, pH 7.2]); SDS (sodium dodecyl sulfate); Tris (tris(hydroxymethyl)aminomethane); w/v (weight to volume); w/w (weight to weight); v/v (volume to volume); and Genencor (Genencor International, Inc., Palo Alto, Calif.).

Example 1

Construction of a CBH1-E1 Fusion Vector

The CBH 1-E1 fusion construct included the *T. reesei* cbh1 promoter; the *T. reesei* cbh1 gene sequence from the start codon to the end of the cbh1 linker and an additional 12 bases of DNA 5' to the start of the endoglucanase coding sequence, a stop codon and the *T. reesei* cbh1 terminator (see FIGS. 10 and 11). The additional 12 DNA bases (ACTAGTAAGCGG)) (SEQ ID NO. 16) code for the restriction endonuclease SpeI and the amino acids Ser, Lys, and Arg.

The plasmid E1-pUC19 which contained the open reading frame for the E1 gene locus was used as the DNA template in a PCR reaction. (Equivalent plasmids are described in U.S. Pat. No. 5,536,655, which describes cloning the E1 gene from the actinomycete *Acidothermus cellulolyticus* ATCC 43068, Mohagheghi A. et al., 1986).

Standard procedures for working with plasmid DNA and amplification of DNA using the polymerase chain reaction (PCR) are found in Sambrook, et al., 2001.

The following two primers were used to amplify the coding region of the catalytic domain of the E1 endoglucanase.
Forward Primer 1=EL-316 (containing a SpeI site): GCTTAT ACTAGTAAGCGCGCGGGCGGCGGCTATTGGCACAC (SEQ ID NO: 17)

Reverse Primer 2=EL-317 (containing an AscI site and stop codon-reverse compliment):
GCTTAT GGCGCGCCTTAGACAGGATCGAAAATCGACGAC (SEQ ID NO: 18).

The reaction conditions were as follows using materials from the PLATINUM Pfx DNA Polymerase kit (Invitrogen, Carlsbad, Calif.): 1 µl dNTP Master Mix (final concentration 0.2 mM); 1 µl primer 1 (final conc 0.5 µM); 1 µl primer 2 (final conc 0.5 µM); 2 µl DNA template (final conc 50-200 ng); 1 µl 50 mM MgSO4 (final conc 1 mM); 5 µl 10× Pfx Amplification Buffer; 5 µl 10×PCRx Enhancer Solution; 1 µl Platinum Pfx DNA Polymerase (2.5 U total); 33 µl water for 50 µl total reaction volume.

Amplification parameters were: step 1—94° C. for 2 min (1st cycle only to denature antibody bound polymerase); step 2—94° C. for 45 sec; step 3—60° C. for 30 sec; step 4—68° C. for 2 min; step 5—repeated step 2 for 24 cycles and step 6—68° C. for 4 min.

The appropriately sized PCR product was cloned into the Zero Blunt TOPO vector and transformed into chemically competent Top10 $E.\ coli$ cells (Invitrogen Corp., Carlsbad, Calif.)—plated onto to appropriate selection media (LA with 50 ppm with kanamycin and grown overnight at 37° C. Several colonies were picked from the plate media and grown overnight in 5 ml cultures at 37° C. in selection media (LB with 50 ppm kanamycin) from which plasmid mini-preps were made. Plasmid DNA from several clones was restriction digested to confirm the correct size insert. The correct sequence was confirmed by DNA sequencing. Following sequence verification, the E1 catalytic domain was excised from the TOPO vector by digesting with the restriction enzymes SpeI and AscI. This fragment was ligated into the pTrex4 vector which had been digested with the restriction enzymes SpeI and AscI (see, FIGS. 12 and 13).

The ligation mixture was transformed into MM294 competent $E.\ coli$ cells, plated onto appropriate selection media (LA with 50 ppm carbenicillin) and grown overnight at 37° C. Several colonies were picked from the plate media and grown overnight in 5 ml cultures at 37° C. in selection media (LA with 50 ppm carbenicillin) from which plasmid mini-preps were made. Correctly ligated CBH1-E1 fusion protein vectors were confirmed by restriction digestion.

Example 2

Transformation and Expression the CBH1-E1 Fusion Construct into a *T. reesei* Host Strain Various *T. reesei* strains were transformed with the CBH1-E1 fusion construct. The host strains included a derivative of *T. reesei* RL-P37 and a derivative of *T. reesei* wherein the native cellulase genes (cbh1, cbh2, egl1 and egl2) were deleted.

Approximately one-half swab (or 1-2 cm$^2$) of a plate of a sporulated *T. reesei* derivative of strain RL-P37 (Sheir-Neiss, et al., 1984) mycelia (grown on a PDA plate for 7 days at 28° C.) was inoculated into 50 ml of YEG (5 g/L yeast extract plus 20 g/L glucose) broth in a 250 ml, 4-baffled shake flask and incubated at 30° C. for 16-20 hours at 200 rpm. The mycelia was recovered by transferring the liquid volume into 50 ml conical tubes and spinning at 2500 rpm for 10 minutes. The supernatant was aspirated off. The mycelial pellet was transferred into a 250 ml, CA Corning bottle containing 40 ml of B glucanase solution and incubated at 30° C., 200 rpm for 2 hrs to generate protoplasts for transformation. Protoplasts were harvested by filtration through sterile miracloth into a 50 ml conical tube. They were pelleted by spinning at 2000 rpm for 5 minutes, the supernate was aspirated off. The protoplast pellet was washed once with 50 ml of 1.2 M sorbitol, spun down, aspirated, and washed with 25 ml of sorbitol CaCl$_2$. Protoplasts were counted and then pelleted again at 2000 rpm for 5 min, the supernate was aspirated off, and the protoplast pellet was resuspended in a sufficient volume of sorbitol/CaCl$_2$ to generate a protoplast concentration of 1.25×10$^8$ protoplasts per ml. This constitutes the protoplast solution.

Aliquots of up to 20 µg of expression vector DNA (in a volume no greater than 20 µl) were placed into 15 ml conical tubes and the tubes were put on ice. Then 200 µl of the is protoplast solution was added, followed by 50 µl PEG solution to each transformation aliquot. The tubes were mixed gently and incubated on ice for 20 min. Next, an additional 2 ml of PEG solution was added to the transformation aliquot tubes, followed by gentle inversion and incubation at room temperature for 5 minutes. Next 4 ml of Sorbitol/CaCl$_2$ solution was added to the tubes (generating a total volume of 6.2 ml). This transformation mixture was divided into 3 aliquots each containing about 2 ml. An overlay mixture was created by adding each of these three aliquots to three tubes containing 10 ml of melted acetamide/sorbitol top agar (kept molten by holding at 50° C.) and this overlay mixture was poured onto a selection plate of acetamide/sorbitol agar. The transformation plates were then incubated at 30° C. for four to seven days.

The transformation was performed with amdS selection. Acetamide/sorbitol plates and overlays were used for the transformation. For the selection plates, the same plates were used, but without sorbitol. Transformants were purified by transfer of isolated colonies to fresh selective media containing acetamide.

With reference to the examples the following solutions were made as follows.

1) 40 ml β-D-glucanase solution was made up in 1.2M sorbitol and included 600 mg β-D-glucanase and 400 mg MgSO$_4$.7H$_2$O (Catalog No. 0439-1, InterSpex Products Inc., San Mateo, Calif.).
2) 200 ml PEG solution contained 50 g polyethylene glycol 4000 (BDH Laboratory Supplies Poole, England) and 1.47 g CaCl$_2$.2H$_2$O made up in dH$_2$O.
3) Sorbitol/CaCl$_2$ contained 1.2M sorbitol and 50 mM CaCl$_2$.
4) Acetamide/sorbitol agar:
   Part 1—0.6 g acetamide (Aldrich, 99% sublime.), 1.68 g CsCl, 20 g glucose, 20 g KH$_2$PO$_4$, 0.6 g MgSO$_4$.7H$_2$O, 0.6 g CaCl$_2$.2H$_2$O, 1 ml 1000× salts (see below), adjusted to pH 5.5, brought to volume (300 mls) with dH$_2$O, filtered and sterilized.
   Part II—20 g Noble agar and 218 g sorbitol brought to volume (700 mls) with dH$_2$O and autoclaved.
   Part II was added to part I for a final volume of 1 L.
5) 1000× Salts—5 g FeSO$_4$.7H$_2$O, 1.6 g MnSO$_4$.H$_2$O, 1.4 g ZnSO$_4$.7H$_2$O, 1 g CoCl$_2$.6H$_2$O were combined and the volume was brought to 1 L with dH$_2$O. The solution was filtered and sterilized.
6) Acetamide/sorbitol top agar is prepared as is acetamide/sorbitol agar except that top agar is substituted for noble agar.

The transformation procedure used was similar to that decribed in Penttila et al., Gene 61: 155-164, 1987.

Individual fungal transformants were grown up in shake flask culture to determine the level of fusion protein expression. The experiments were conducted essentially as described in example 1 of U.S. Pat. No. 5,874,276 with the following modification: 16 g/L of alpha-lactose was substituted for cellulose in TSF medium. The highest level of cleaved E1 protein expression from a transformant in shake flasks was estimated to be greater than 3 g/L.

In general, the fermentation protocol as described in Foreman et al. (Foreman et al. (2003) *J. Biol. Chem* 278:31988-31997) was followed. Vogels minimal medium (Davis et al., (1970) Methods in Enzymology 17A, pg 79-143 and Davis, Rowland, NEUROSPORA, CONTRIBUTIONS OF A MODEL ORGANISM, Oxford University Press, (2000)) containing 5% glucose was inoculated with 1.5 ml frozen spore suspension. After 48 hours, each culture was transferred to 6.2 L of the same medium in a 14 L Biolafitte fermenter. The fermenter was run at 25° C., 750 RPM and 8 standard liters per minute airflow. One hour after the initial glucose was exhausted, a 25% (w/w) lactose feed was started and fed in a carbon limiting fashion to prevent lactose accumulation. The concentrations of glucose and lactose were monitored using a glucose oxidase assay kit or a glucose hexokinase assay kit with beta-galactosidase added to cleave lactose, respectively (Instrumentation Laboratory Co., Lexington, Mass.). Samples were obtained at regular intervals to monitor the progress of the fermentation. Collected samples were spun in a 50 ml centrifuge tube at ¾ speed in an International Equipment Company (Needham Heights, Mass.) clinical centrifuge.

Figure 14:
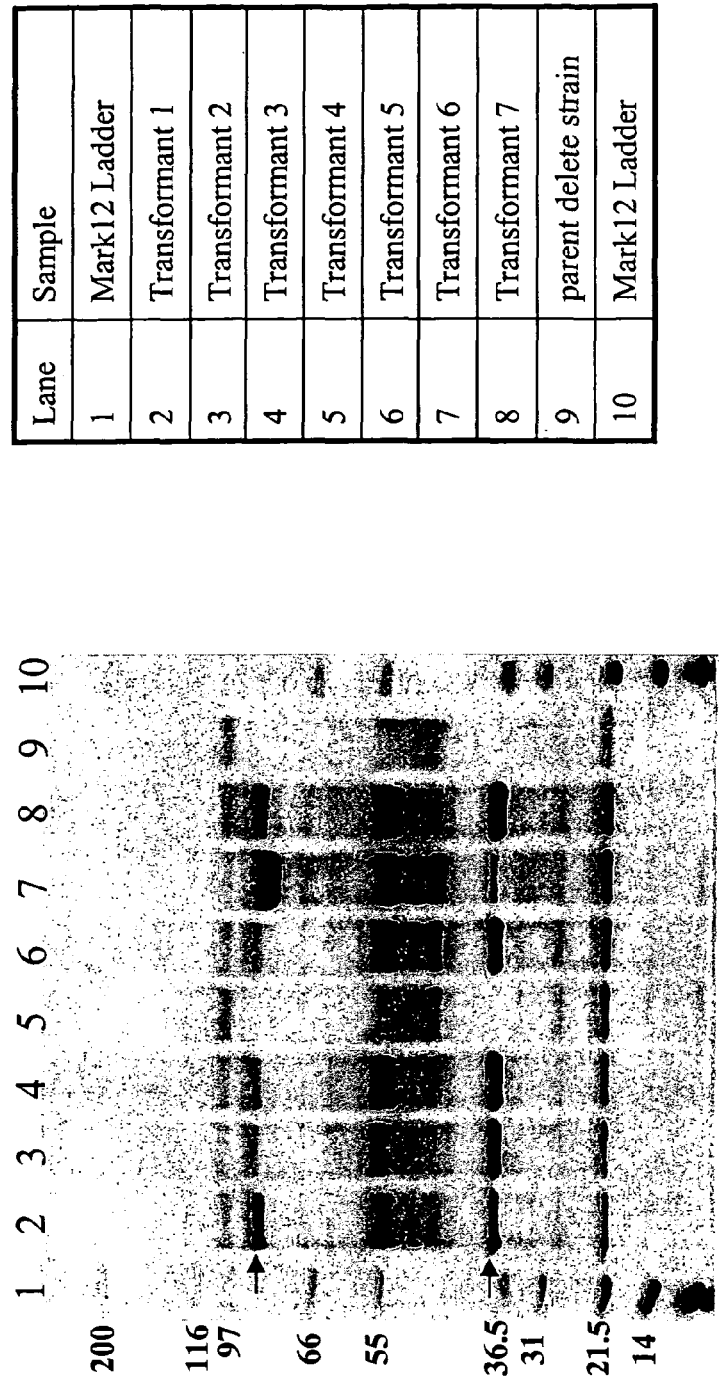
FIG. 14 illustrates a SDS-PAGE gel of supernate samples of shake flask growth of clones of a *T. reesei* strain deleted for the cellulases, cbh1, cbh2, egl1 and egl2 and transformed with the CBH1-E1 fusion construct. Lanes 1 and 10 represent MARK 12 Protein Standard (Invitrogen, Carlsbad, Calif.). Lanes 2-8 represent various transformants and lane 9 represents the untransformed *T. reesei* strain. The upper arrow indicates the cellulase fusion protein and the lower arrow indicates the cleaved E1 catalytic domain.

Shake flask grown supernatant samples were run on BIS-TRIS SDS-PAGE gels (Invitrogen), under reducing conditions with MOPS (morpholinepropanesulfonic acid) SDS running buffer and LDS sample buffer. The results are provided in FIG. 14.

Example 3

Assay of Cellulolytic Activity from Transformed *Trichoderma reesei* Clones

The following assays and substrates were used to determine the cellulolytic activity of the CBHL1-E1 fusion protein.

Pretreated corn stover (PCS)—Corn stover was pretreated with 2% w/w $H_2SO_4$ as described in Schell, D. et al., J. Appl. Biochem. Biotechnol. 105:69-86 (2003) and followed by multiple washes with deionized water to obtain a pH of 4.5. Sodium acetate was added to make a final concentration of 50 mM and this was titrated to pH 5.0.

Measurement of Total Protein—Protein concentration was measured using the bicinchoninic acid method with bovine serum albumin as a standard. (Smith P. K. et al., Biochem 150:76-85, 1985).

Cellulose conversion (Soluble sugar determinations) was evaluated by HPLC according to the methods described in Baker et al., Appl. Biochem. Biotechnol. 70-72:395-403 (1998).

A standard cellulosic conversion assay was used in the experiments. In this assay enzyme and buffered substrate were placed in containers and incubated at a temperature over time. The reaction was quenched with enough 100 mM Glycine, pH 11.0 to bring the pH of the reaction mixture to at least pH10. Once the reaction was quenched, an aliquot of the reaction mixture was filtered through a 0.2 micron membrane to remove solids. The filtered solution was then assayed for soluble sugars by HPLC as described above. The cellulose concentration in the reaction mixture was approximately 7%. The enzyme or enzyme mixtures were dosed anywhere from 1 to 60 mg of total protein per gram of cellulose.

In one set of experiments the percent conversion of 13.8% PCS (7.06% cellulose) at 55° C. for 1 day was evaluated using 10 mg enzyme/g cellulose in 50 mM acetate buffer at 55° C. Samples were agitated at 700 rpm. Comparisons were made between supernatants from growth of 1) a *T. reesei* parent strain which included the native cellulase genes and 2) a corresponding *T. reesei* CBH1-E1 fusion strain transformed according to the examples herein. The amount of E1 protein expressed by this strain was 10% w/w (estimated by PAGE as a percent of total protein). Samples were quenched at various times up to 24 hours.

Figure 17:
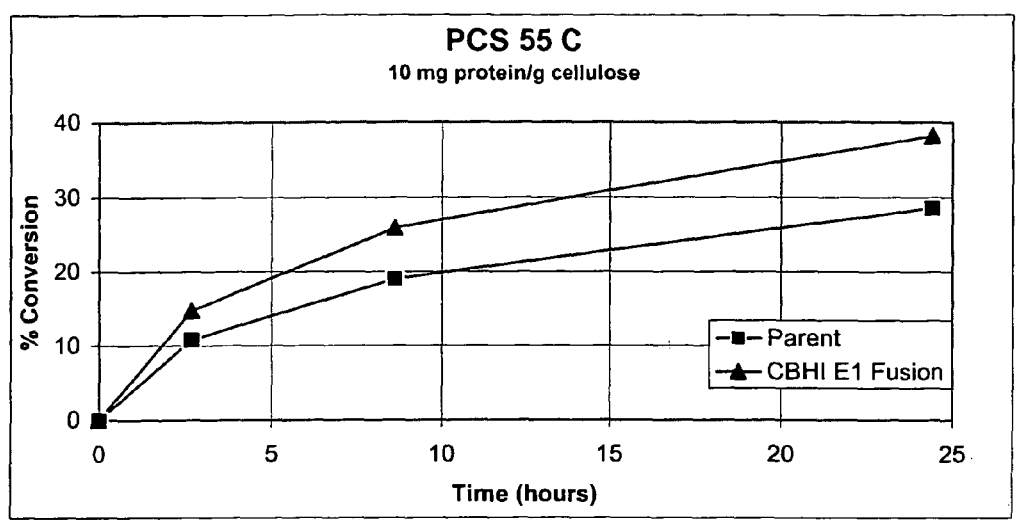
FIG. 17 illustrates the % cellulose conversion to soluble sugars over time for a *T. reesei* parent strain comprising native cellulase genes with a corresponding *T. reesei* strain which expresses the CBH1-E1 fusion protein and reference is made to example 3.

The results are presented in FIG. 17, and it is observed that the CBH1-E1 fusion protein outperforms the parent. It took about 6 hours for the CBH1-E1 fusion protein to yield 20% cellulose conversion, while it requires 10 hours for the parent cellulase to reach 20% hydrolysis.

Example 4

Transformation and Expression the CBH1-74E Fusion Construct into *T. reesei*

The CBH1-74E fusion construct was designed according to the procedures described above in example 1 with the following differences. The forward primer was designed to maintain the reading frame translation and included a Lys-Arg kexin cleavage site (underlined). The reverse primer encodes a stop codon (the reverse compliment) at the end of the catalytic domain.

Primers were ordered with 5 prime phosphates to enable subsequent blunt cloning. The GH74 catalytic domain was amplified with the following forward and reverse primers:

```
                                       (SEQ ID NO: 19)
GH74 forward primer bluntF4-
CTAAGAGAGCGACGACTCAGCCGTACACCTGGAGCAACGTGGC
and (SEQ ID NO: 20)
GH74 reverse primer bluntR4-
TTACGATCCGGACGGCGCACCACCAATGTCCCCGTATA.
```

Amplification was performed using Stratagene's Herculase High Fidelity Polymerase (Stratagene, La Jolla, Calif.). The amplification conditions for the GH74 catalytic domain were:

An isolated fragment of DNA encompassing the GH74 catalytic domain was used as the template for PCR (approximately 0.2 ug of DNA). U.S. pat. appln. No. 20030108988 describes the cloning of GH74. (GH74 is referred to as AviIII in the published patent application).

Reaction set up (in ul):

| COMPONENT | |
|---|---|
| 10× Herculase Buffer | 5 |
| 10 mM dNTPs | 1.5 |
| $H_2O$ | 39.5 |
| Fwd primer (10 µM) | 1 |
| Rev primer (10 µM) | 1 |
| Template | 1 |
| Herculase Polymerase (5U) | 1 |
| Total reaction volume | 50 |

Cycling:

| Segment | No. of cycles | Temp ° C. | hr:min:sec |
|---|---|---|---|
| 1 | 1 | 95 | 00:03:00 |
| 2 | 10 | 95 | 00:00:40 |
|   |   | 60 | 00:00:30 |
|   |   | 72 | 150 sec |
| 3 | 20 | 95 | 00:00:40 |
|   |   | 60 | 00:00:30 |
|   |   | 72 | 150 sec + 10 sec/cycle |
| 4 | 1 | 4 | hold |

All PCR products were gel purified and treated with Mung Bean Nuclease to produce blunt ends prior to ligation. The amplified, blunted fragment was ligated into pTrex4 vector that had been digested with the restriction enzymes SpeI and AscI followed by nuclease digestion to remove the 3' overhangs thereby creating blunt ends. The newly created vector was then transformed into E. coli. Plasmid DNA was isolated from colonies of transformed E. coli. Since the amplified GH74 fragment could insert into pTrex4 in two different orientations, restriction digests were performed to discern clones with correctly oriented insert. Putative clones were confirmed by DNA sequencing. Transformation of the fusion vector into T. reesei was performed using biolistic transformation according to the teaching of Hazell, B. W. et al., Lett. Appl. Microbiol. 30:282-286 (2000).

Expression of the CBH1-74E fusion protein was determined as described above for expression of the CBH1-E1 fusion protein in Example 2. The highest level of cleaved GH74 protein expression from a transformant in shake flasks was estimated to be greater then 3 g/L.

Figure 15:
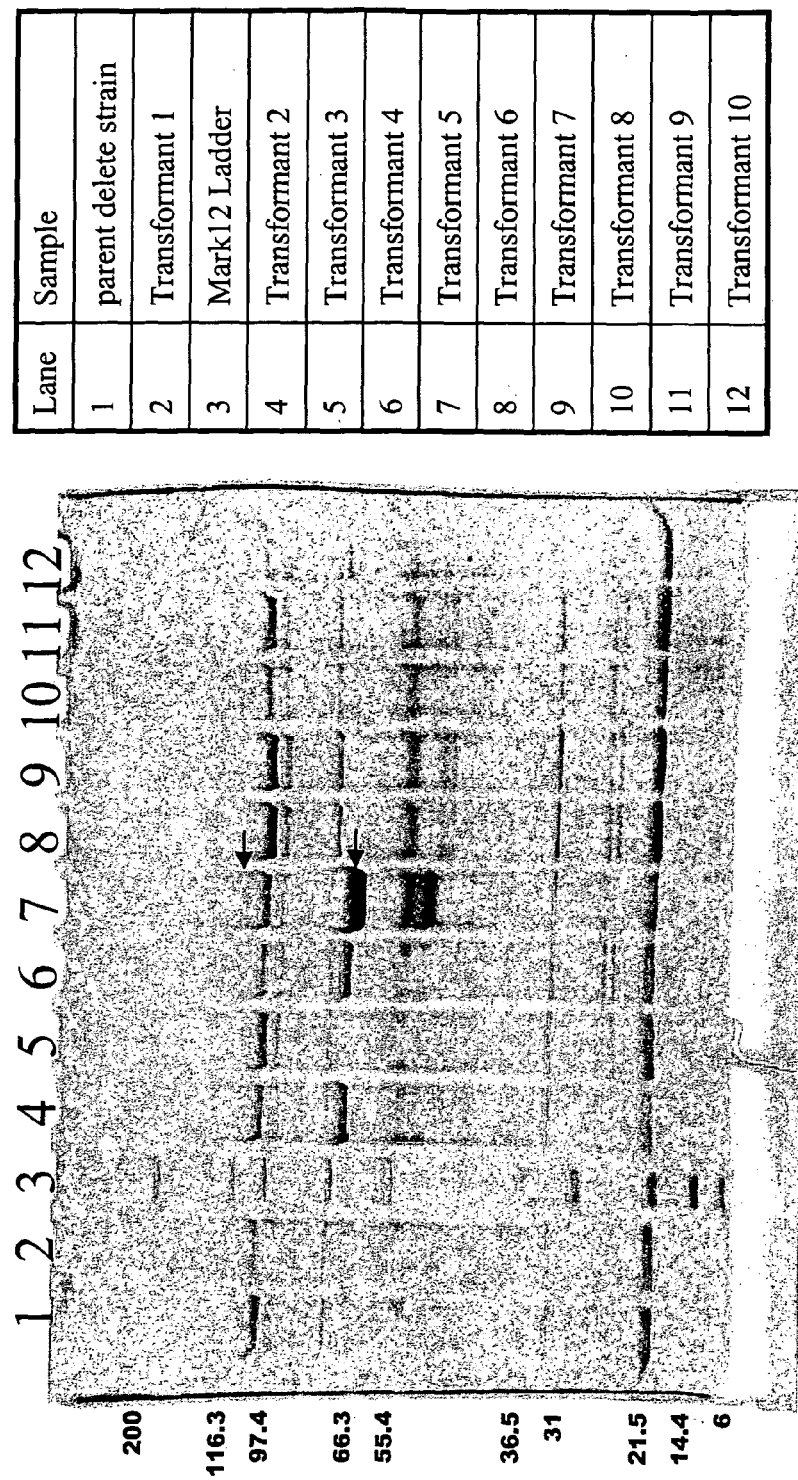
FIG. 15 illustrates a SDS-PAGE gel of supernate samples of shake flask growth of clones of a *T. reesei* strain deleted for the cellulases, cbh1, cbh2, egl1 and egl2 and transformed with the CBH1-GH74 fusion construct. Lane 1 represents the untransformed control. Lane 3 represents MARK 12 Protein Standard (Invitrogen, Carlsbad, Calif.). Lanes 2 and 4-12 represent various transformants. The upper arrow indicates the CBH1-GH74 fusion protein and the lower arrow indicates the cleaved GH74 catalytic domain.

Shake flask grown supernatant samples were run on BIS-TRIS SDS-PAGE gels (Invitrogen), under reducing conditions with MOPS (morpholinepropanesulfonic acid) SDS running buffer and LDS sample buffer. The results are provided in FIG. 15.

Example 5

Transformation and Expression the CBH1-TfE5 Fusion Construct into T. reesei

The CBH1-TfE5 fusion construct was designed according to the procedures described above in example 1 with the following differences. A plasmid equivalent to that described in Collmer & Wilson, Bio/technol. 1: 594-601(1983) carrying the TfE5 gene was used as the DNA template to amplify the TfE5. The following primers were used to amplify the TfE5 endoglucanase
EL-308 (which contains a SpeI site)—forward primer—GCTTAT ACTAGTMGCGCGCCGGTCTCACCGCCACAGTCACC (SEQ ID NO: 21) and
EL-309 (which contains a AscI site) reverse primer—GCTTATGGCGCGCCTCAGGACTGGAGCTTGCTCCGC (SEQ ID NO: 22).

Transformation was as described in example 2 above. The highest level of cleaved TfE5 protein expression from a transformant in shake flasks was estimated to be greater than 2 g/L.

Figure 16:
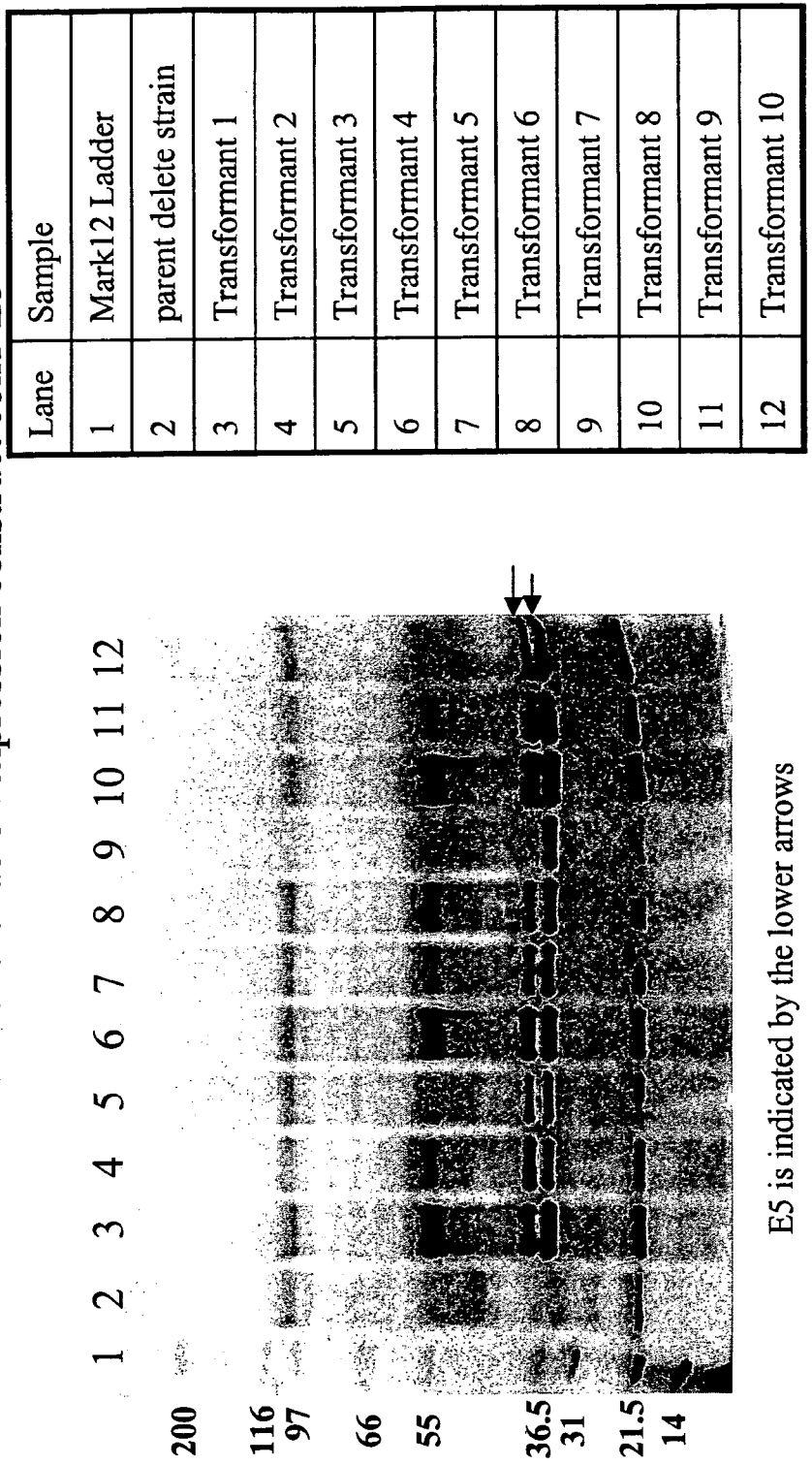
FIG. 16 illustrates a SDS-PAGE gel of supernate samples of shake flask growth of clones of a *T. reesei* strain deleted for the cellulases, cbh1, cbh2, egl1 and egl2 and transformed with the CBH1-TfE5 fusion construct. Lane1 represents MARK 12 Protein Standard (Invitrogen, Carlsbad, Calif.). Lane 2 represents the untransformed strain and lanes 3-12 represent various transformants. Arrows indicate new bands observed in the CBH1-TfE5 expressing transformants.

Shake flask grown supernatant samples were run on BIS-TRIS SDS-PAGE gels (Invitrogen), under reducing conditions with MOPS (morpholinepropanesulfonic acid) SDS running buffer and LDS sample buffer. The results are provided in FIG. 16.

REFERENCES

Altschul, S. F., et al., J. Mol. Biol. 215:403-410,1990.
Altschul, S. F., et al., Nucleic Acids Res. 25:3389-3402, 1997.
Aro N, Saloheimo A, Ilmen M, Penttila M. ACEII, a novel transcriptional activator involved in regulation of cellulase and xylanase genes of Trichoderma reesei. J Biol Chem. 2001 Jun. 29; 276(26):24309-14. (Epub 2001 Apr. 13.)
Aubert J. P. et al, p11 et seq., Biochemistry and Genetics of Cellulose Degradation, eds. Aubert, J. P., Beguin, P., Millet, J., Federation of European Microbiological Societies, Academic Press, 1988
Ausubel G. M., et al. CURRENT PROTOCOLS IN MOLECULAR BIOLOGY, John Wiley & Sons, New York, N.Y., 1993.
Baker et al., Appl. Biochem. and Biotechnol. 45/46:245-256, 1994.
Bhikhabhai, R. et al., J. Appl. Biochem. 6:336, 1984.
Boel et al. EMBO J 3:1581-1585 1984.
Brumbauer, A. et al., Bioseparation 7:287-295,1999.
Collmer, A. and D. B. Wilson Bio/Technol/1:594-601, 1983.
Deutscher, M. P., Methods Enzymol. 182:779-80,1990.
Ellouz, S. et al., J. Chromatography 396:307, 1987.
Filho, et al. Can. J. Microbiol. 42:1-5, 1996.
Fliess, A., et al., Eur. J. Appl. Microbiol. Biotechnol. 17:314, 1983.
Goedegebuur et al., Curr. Genet. 41:89-98, 2002.
Goyal, A. et al. Bioresource Technol. 36:37, 1991.
Hazell, B. W. et al., Lett. Appl. Microbiol. 30:282-286, 2000.
Herr et al., Appl. Biochem. Biotechnol. 5:29-36, 1978.
Hu et al., Mol. Cell. Biol. 11:5792-9, 1991.
Jeeves et al., Biotechnol. Genet. Eng. Rev. 9:327-369,1991.
Kawaguchi, T et al., Gene 173(2):287-8, 1996.
Kelley et al. EMBO J. 4:475-479,1985.
Knowles, J. et al., TIBTECH 5, 255-261, 1987.
Krishna, S. et al., Bioresource Tech. 77:193-196, 2001.
Kuhls K. et al., Proc. Natl. Acad. Sci. USA 93(15): 7755-7760, 1996.
Kumar, A., et al., Textile Chemist and Colorist 29:37-42, 1997.
Medve, J. et al., J. Chromatography A 808:153, 1998.
Mohagheghi, A. et al., Int. J. Syst. Bacteriol. 36:435-443, 1986.
Nieves et al., Appl. Biochem. and Biotechnol. 51/52 211-223, 1995.
Nunberg et al. Mol. Cell Biol. 4:2306-2315 1984.
Ohmiya et al., Biotechnol. Gen. Engineer. Rev. 14:365-414, 1997.
Okada, M. et al., Appl. Environ. Microbiol., 64:555-563, 1988.
Ooi et al., Nucleic Acid Res. 18:5884, 1990
Penttila et al., Gene 45:253-263, 1986.
Penttila et al., Gene 61: 155-164, 1987.
Penttila et al., Gene 63: 103-112, 1988.
Pere, J., et al., In Proc. Tappi Pulping Conf., Nashville, Tenn., 27-31, pp. 693-696, 1996.
Saarilahti et al., Gene 90:9-14, 1990.
Sakamoto et al., Curr. Genet. 27:435-439,1995.
Saloheimo M, et al., Gene 63:11-22,1988.
Saloheimo, A. et al., Molecular Microbiology, 13:219-228, 1994.
Saloheimo, M. et al., Eur. J. Biochem., 249:584-591, 1997.
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.

Shoemaker et al., Biochem. Biophys. Acat. 523:133-146 1978.
Shoemaker, S. et al., Bio/Technology, 1:691-696, 1983
Srisodsuk, M. et al. J. Biol. Chem. 268(28): 20756-20761, 1993.
Strathern et al., eds. (1981) The Molecular Biology of the Yeast *Saccharomyces*, Cold Spring Harbor Press, Plainview. N.Y.
Suurnakki, A. et al., Cellulose 7:189-209, 2000.
Teeri, T. et al., Gene, 51:43-52, 1987

Van Tilbeurgh, H. et al., FEBS Lett. 16:215, 1984.
Tomaz, C. and Queiroz, J., J. Chromatography A 865:123-128, 1999.
Tomme, P. et al., Eur. J. Biochem. 170:575-581, 1988.
Van Tilbeurgh, H. et al., FEBS Lett. 204:223-227, 1986.
Ward, M. et al., Appl. Microbiol. Biotechnol. 39:738-743, 1993.
Wood, Biochem. Soc. Trans., 13, pp. 407-410, 1985.
Wood et al., METHODS IN ENZYMOLOGY, 160, 25, p. 87 et seq., Academic Press, New York, 1988.

What is claimed is:

1. A cellulase fusion protein (1) comprising the amino acid sequence of SEQ ID NO:14; (2) encoded by a nucleotide sequence that comprises SEQ ID NO:13; or (3) encoded by a nucleotide sequence that differs from SEQ ID NO:13 but encodes the same enzyme as SEQ ID NO:13 due to degeneracy of genetic code.

2. The cellulase fusion protein of claim 1, produced by a recombinant fungal host cell.

3. The cellulase fusion protein of claim 2, wherein the recombinant fungal host cell is a *Trichoderma* host cell.

4. The cellulase fusion protein of claim 3, wherein the *Trichoderma* host cell is a strain of *T. reesei*.

5. The cellulase fusion protein of claim 4, wherein at least one of cbh1, cbh2, egl1, and egl2 genes of the *T. reesei* host cell has been deleted.

6. A composition comprising the cellulase fusion protein of claim 1.

7. A method of using the composition of claim 6 to achieve cellulose conversion.

* * * * *